US012805872B2

(12) United States Patent
Tinkham et al.

(10) Patent No.: US 12,805,872 B2
(45) Date of Patent: Nov. 24, 2026

(54) MECHANISM TO CREATE ENTEROTOMY BETWEEN ONE OR MORE COMPRESSION DEVICES

(71) Applicant: G.I. Windows, Inc., Westwood, MA (US)

(72) Inventors: Brian P. Tinkham, Scituate, MA (US); Jeffrey M. Wallace, Pittsford, NY (US); Dane T. Seddon, Boston, MA (US); Jonathan P. Boduch, Quincy, MA (US); Shani Mann, Needham, MA (US)

(73) Assignee: G.I. Windows, Inc., Canton, MA (US)

( * ) Notice: Subject to any disclaimer, the term of this patent is extended or adjusted under 35 U.S.C. 154(b) by 431 days.

(21) Appl. No.: 18/378,829

(22) Filed: Oct. 11, 2023

(65) Prior Publication Data

US 2024/0041461 A1 Feb. 8, 2024

Related U.S. Application Data

(63) Continuation of application No. PCT/US2022/025353, filed on Apr. 19, 2022.

(60) Provisional application No. 63/257,933, filed on Oct. 20, 2021, provisional application No. 63/177,192, filed on Apr. 20, 2021.

(51) Int. Cl.
*A61B 17/11* (2006.01)
*A61B 17/00* (2006.01)
*A61B 17/34* (2006.01)

(52) U.S. Cl.
CPC .......... *A61B 17/1114* (2013.01); *A61B 17/34* (2013.01); *A61B 2017/00876* (2013.01)

(58) Field of Classification Search
CPC . A61B 17/1114; A61B 17/34; A61B 17/3478; A61B 2017/00349; A61B 2017/00557; A61B 2017/00876; A61B 2017/00986; A61B 2017/1139; A61B 2017/22044
USPC .......................................................... 606/153
See application file for complete search history.

(56) References Cited

U.S. PATENT DOCUMENTS

| | | | |
|---|---|---|---|
| 4,197,840 | A | 4/1980 | Beck et al. |
| 4,538,130 | A | 8/1985 | Gluckstern et al. |
| 5,300,910 | A | 4/1994 | Unkelbach et al. |
| 5,320,629 | A | 6/1994 | Noda et al. |

(Continued)

FOREIGN PATENT DOCUMENTS

| | | | |
|---|---|---|---|
| CN | 105011985 | A | 11/2015 |
| CN | 205379345 | U | 7/2016 |

(Continued)

OTHER PUBLICATIONS

Author Unknown, "An Innovative Implant for the Creation of Anastomosis," PLIO, retrieved from the internet at: https://pliosurgical.com/, Jan. 19, 2024 (13 pages).

(Continued)

*Primary Examiner* — Jocelin C Tanner
(74) *Attorney, Agent, or Firm* — Nutter McClennen & Fish LLP

(57) ABSTRACT

The invention provides systems, devices, and methods for the delivery, deployment, and positioning of magnetic compression devices at a desired site so as to improve the accuracy of anastomoses creation between tissues, organs, or the like.

18 Claims, 66 Drawing Sheets

(56) References Cited

U.S. PATENT DOCUMENTS 5,381,784 A 1/1995 Adair
5,431,670 A 7/1995 Holmes
5,595,562 A 1/1997 Grier
5,690,656 A 11/1997 Cope et al.
6,129,668 A 10/2000 Haynor et al.
6,132,458 A 10/2000 Staehle et al.
6,190,303 B1 2/2001 Glenn et al.
6,273,895 B1 8/2001 Pinchuk et al.
6,352,543 B1 3/2002 Cole
6,371,964 B1 4/2002 Vargas et al.
6,478,210 B2 11/2002 Adams et al.
6,537,284 B1 3/2003 Inoue
6,632,229 B1 10/2003 Yamanouchi et al.
6,652,540 B1 11/2003 Cole et al.
6,699,263 B2 3/2004 Cope
6,719,768 B1 4/2004 Cole et al.
6,802,847 B1 10/2004 Carson et al.
6,827,718 B2 12/2004 Hutchins et al.
6,932,827 B2 8/2005 Cole
7,282,057 B2 10/2007 Surti et al.
7,618,427 B2 11/2009 Oritz et al.
7,641,638 B2 1/2010 Waxman et al.
7,760,059 B2 7/2010 Higuchi
7,909,837 B2 3/2011 Crews et al.
8,043,290 B2 10/2011 Harrison et al.
8,118,821 B2 2/2012 Mouw
8,142,454 B2 3/2012 Harrison et al.
8,262,680 B2 9/2012 Swain et al.
8,439,915 B2 5/2013 Harrison et al.
8,506,516 B2 8/2013 Kassab et al.
8,518,062 B2 8/2013 Cole et al.
8,556,919 B2 10/2013 Aguirre et al.
8,603,121 B2 12/2013 Surti et al.
8,623,036 B2 1/2014 Harrison et al.
8,679,139 B2 3/2014 Aguirre et al.
8,685,046 B2 4/2014 Viola
8,728,105 B2 5/2014 Aguirre
8,794,243 B2 8/2014 Deem et al.
8,828,031 B2 9/2014 Fox et al.
8,828,032 B2 9/2014 McWeeney et al.
8,845,663 B2 9/2014 Chmura
8,864,781 B2 10/2014 Surti et al.
8,870,899 B2 10/2014 Beisel et al.
8,915,915 B2 12/2014 Harrison et al.
9,168,041 B2 10/2015 Zaritsky et al.
9,226,753 B2 1/2016 Surti et al.
9,320,524 B2 4/2016 Gagner et al.
9,421,015 B2 8/2016 Gagner et al.
9,456,820 B2 10/2016 Gagner et al.
9,492,173 B2 11/2016 McWeeney et al.
9,539,010 B2 1/2017 Gagner et al.
9,763,664 B2 9/2017 Beisel et al.
9,801,635 B2 10/2017 Gagner et al.
9,877,724 B2 1/2018 Gagner et al.
9,943,335 B2 4/2018 Gittard et al.
10,039,550 B2 8/2018 Altman
10,159,487 B2 12/2018 Gagner et al.
10,182,821 B2 1/2019 Lukin et al.
10,285,703 B2 5/2019 Viola
10,342,544 B2 7/2019 Bakos et al.
10,376,400 B2 8/2019 McGuckin, Jr.
10,448,954 B2 10/2019 McWeeney et al.
10,517,600 B2 12/2019 Beisel et al.
10,555,735 B2 2/2020 Bakos et al.
10,568,630 B2 2/2020 Hernandez et al.
10,595,869 B2 3/2020 Beisel et al.
10,624,643 B2 4/2020 Hunt et al.
10,624,644 B2 4/2020 Bakos et al.
10,631,865 B2 4/2020 Bakos et al.
10,667,817 B2 6/2020 Gagner et al.
10,682,143 B2 6/2020 Hernandez et al.
10,779,831 B2 9/2020 Lukin et al.
10,813,642 B2 10/2020 Beisel et al.
10,952,732 B2 3/2021 Binmoeller et al.
11,039,838 B2 6/2021 Binmoeller et al.
11,311,298 B2 4/2022 Gagner et al.
11,432,873 B2 9/2022 Brown et al.
2002/0055674 A1 5/2002 Ben-Haim et al.
2002/0143347 A1 10/2002 Cole et al.
2003/0149422 A1 8/2003 Muller
2003/0176767 A1 9/2003 Long et al.
2004/0034377 A1 2/2004 Sharkawy et al.
2004/0059280 A1 3/2004 Makower et al.
2005/0020958 A1 1/2005 Paolini et al.
2005/0080439 A1 4/2005 Carson et al.
2005/0165427 A1* 7/2005 Jahns ................ A61B 17/0482 606/153
2005/0256503 A1 11/2005 Hall
2005/0277966 A1 12/2005 Ewers et al.
2005/0283235 A1 12/2005 Kugler et al.
2006/0036267 A1* 2/2006 Saadat ................ A61B 17/1114 606/153
2006/0271107 A1 11/2006 Harrison et al.
2006/0282106 A1 12/2006 Cole et al.
2007/0106312 A1 5/2007 Vargas et al.
2007/0276378 A1 11/2007 Harrison et al.
2008/0051626 A1 2/2008 Sato et al.
2008/0086192 A1 4/2008 WasDyke et al.
2008/0114384 A1 5/2008 Chang et al.
2008/0183272 A1 7/2008 Wood et al.
2008/0200933 A1* 8/2008 Bakos ................ A61B 17/1114 606/153
2008/0200934 A1* 8/2008 Fox .................... A61B 17/1114 606/153
2008/0208105 A1 8/2008 Zelickson et al.
2008/0208224 A1 8/2008 Surti et al.
2008/0243225 A1 10/2008 Satasiya et al.
2008/0262523 A1 10/2008 Makower et al.
2009/0048618 A1 2/2009 Harrison et al.
2009/0062824 A1 3/2009 Berg et al.
2009/0125042 A1 5/2009 Mouw
2009/0227828 A1 9/2009 Swain et al.
2010/0010508 A1 1/2010 Takahashi et al.
2010/0010610 A1 1/2010 Grevious
2010/0036399 A1 2/2010 Viola
2010/0056861 A1 3/2010 Spivey
2010/0099947 A1 4/2010 Sato et al.
2010/0179510 A1 7/2010 Fox et al.
2011/0009886 A1 1/2011 Gagner et al.
2011/0098731 A1 4/2011 Whitbrook et al.
2011/0118765 A1 5/2011 Aguirre
2011/0144560 A1 6/2011 Gagner et al.
2011/0160751 A1 6/2011 Granja Filho
2011/0160752 A1 6/2011 Aguirre
2011/0295055 A1 12/2011 Albrecht et al.
2011/0295285 A1 12/2011 Mcweeney et al.
2012/0022572 A1 1/2012 Braun et al.
2012/0109277 A1* 5/2012 Lepulu .............. A61M 25/0082 606/191
2012/0197062 A1 8/2012 Requarth
2012/0238796 A1 9/2012 Conlon
2012/0259350 A1 10/2012 Gagner et al.
2012/0330330 A1 12/2012 Gagner et al.
2013/0138126 A1 5/2013 Gagner et al.
2013/0150873 A1 6/2013 Gagner et al.
2013/0253548 A1 9/2013 Harrison et al.
2013/0253550 A1 9/2013 Beisel et al.
2013/0325042 A1 12/2013 Fabian et al.
2014/0018824 A1 1/2014 Julian et al.
2014/0019468 A1 1/2014 Federoff et al.
2014/0066709 A1 3/2014 Mirza et al.
2014/0188246 A1 7/2014 Aronson et al.
2014/0194689 A1 7/2014 Carrillo, Jr. et al.
2014/0236064 A1* 8/2014 Binmoeller ........... A61F 5/0076 604/8
2014/0243592 A1 8/2014 Kato et al.
2014/0277342 A1 9/2014 Roeder et al.
2014/0303657 A1 10/2014 Kim et al.
2014/0309669 A1 10/2014 Fabian et al.
2014/0309670 A1 10/2014 Bakos et al.
2014/0343583 A1 11/2014 McWeeney et al.
2014/0379065 A1 12/2014 Johnson et al.
2015/0057687 A1 2/2015 Gittard et al.
2015/0164508 A1 6/2015 Hernandez et al.

(56) References Cited

U.S. PATENT DOCUMENTS

| | | | |
|---|---|---|---|
| 2015/0182224 | A1 | 7/2015 | Altman |
| 2016/0022266 | A1 | 1/2016 | Lukin et al. |
| 2016/0100971 | A1* | 4/2016 | McGuckin, Jr. .......... A61F 2/04 604/8 |
| 2016/0235442 | A1 | 8/2016 | Palese et al. |
| 2016/0262761 | A1 | 9/2016 | Beisel et al. |
| 2016/0287257 | A1 | 10/2016 | Fabian et al. |
| 2016/0324523 | A1 | 11/2016 | Lukin et al. |
| 2016/0367236 | A1 | 12/2016 | Leeflang et al. |
| 2016/0374683 | A1 | 12/2016 | Gagner et al. |
| 2017/0035425 | A1 | 2/2017 | Fegelman et al. |
| 2017/0265866 | A1 | 9/2017 | Ryou et al. |
| 2018/0028186 | A1 | 2/2018 | Yamanouchi |
| 2018/0028187 | A1 | 2/2018 | Gagner et al. |
| 2018/0193061 | A1 | 7/2018 | Gittard et al. |
| 2018/0214149 | A1 | 8/2018 | Hunt et al. |
| 2018/0214150 | A1 | 8/2018 | Bakos et al. |
| 2018/0214152 | A1 | 8/2018 | Bakos et al. |
| 2018/0263625 | A1 | 9/2018 | Lukin et al. |
| 2018/0296218 | A1 | 10/2018 | Binmoeller et al. |
| 2018/0361127 | A1 | 12/2018 | Gray et al. |
| 2019/0133587 | A1 | 5/2019 | Gagner et al. |
| 2019/0133678 | A1 | 5/2019 | Pate et al. |
| 2019/0183507 | A1 | 6/2019 | Baillargeon |
| 2019/0216460 | A1 | 7/2019 | Kopelman |
| 2019/0261998 | A1 | 8/2019 | Altman et al. |
| 2019/0274687 | A1 | 9/2019 | Wang et al. |
| 2019/0328392 | A1 | 10/2019 | Sharma |
| 2019/0374254 | A1* | 12/2019 | Arevalos .......... A61B 17/32053 |
| 2020/0008834 | A1 | 1/2020 | Cauche et al. |
| 2020/0129283 | A1 | 4/2020 | Swensgard et al. |
| 2020/0138438 | A1 | 5/2020 | Harrison et al. |
| 2020/0170776 | A1 | 6/2020 | Folan |
| 2020/0187947 | A1 | 6/2020 | Hernandez et al. |
| 2020/0222049 | A1 | 7/2020 | McWeeney et al. |
| 2020/0229968 | A1 | 7/2020 | Galloway |
| 2020/0246009 | A1 | 8/2020 | Gagner et al. |
| 2020/0323530 | A1 | 10/2020 | Sharma |
| 2021/0100554 | A1* | 4/2021 | Seddon ............... A61B 17/1114 |
| 2021/0161532 | A1 | 6/2021 | Beisel et al. |
| 2021/0169485 | A1 | 6/2021 | Beisel et al. |
| 2021/0169486 | A1 | 6/2021 | Gagner et al. |
| 2021/0244414 | A1 | 8/2021 | Lukin et al. |
| 2022/0087678 | A1 | 3/2022 | Gagner et al. |
| 2022/0104956 | A1 | 4/2022 | Pham et al. |
| 2022/0257252 | A1 | 8/2022 | Todd et al. |
| 2023/0165585 | A1 | 6/2023 | McWeeney et al. |
| 2023/0172608 | A1 | 6/2023 | Lukin et al. |
| 2023/0190269 | A1 | 6/2023 | Tinkham et al. |
| 2023/0255624 | A1 | 8/2023 | Wallace et al. |
| 2023/0389923 | A1 | 12/2023 | Tinkham et al. |
| 2023/0389924 | A1 | 12/2023 | Seddon et al. |
| 2024/0041460 | A1 | 2/2024 | Seddon |
| 2024/0065694 | A1 | 2/2024 | Seddon |
| 2024/0074751 | A1 | 3/2024 | Tinkham et al. |
| 2024/0074755 | A1 | 3/2024 | Mann et al. |
| 2024/0074759 | A1 | 3/2024 | Sugar et al. |

FOREIGN PATENT DOCUMENTS

| | | | |
|---|---|---|---|
| DE | 3011742 | A1 | 10/1981 |
| EP | 1894514 | A2 | 3/2008 |
| EP | 1493391 | B1 | 12/2009 |
| EP | 2207488 | B1 | 9/2012 |
| EP | 2538852 | A1 | 1/2013 |
| EP | 3267905 | A1 | 1/2018 |
| EP | 2260752 | B1 | 3/2018 |
| EP | 3573542 | A1 | 12/2019 |
| EP | 3487418 | A4 | 4/2020 |
| EP | 4115949 | A1 | 1/2023 |
| JP | 2003530916 | A | 10/2003 |
| JP | 2006271832 | A | 10/2006 |
| JP | 2008508939 | A | 3/2008 |
| JP | 2011500159 | A | 1/2011 |
| JP | 2015139592 | A | 8/2015 |
| JP | 2017/521223 | A | 8/2017 |
| JP | 202198077 | A | 7/2021 |
| KR | 20150102567 | A | 9/2015 |
| RU | 2018266 | C1 | 8/1994 |
| SU | 1708313 | A1 | 1/1992 |
| SU | 1725851 | A1 | 4/1992 |
| WO | 01/087398 | A2 | 11/2001 |
| WO | 01/93920 | A2 | 12/2001 |
| WO | 2009048954 | A1 | 4/2009 |
| WO | 2011085006 | A2 | 7/2011 |
| WO | 2011/103400 | A1 | 8/2011 |
| WO | 2013009886 | A1 | 1/2013 |
| WO | 2013/176993 | A1 | 11/2013 |
| WO | 2014055193 | A1 | 4/2014 |
| WO | 2016082481 | A1 | 6/2016 |
| WO | 2016/145414 | A1 | 9/2016 |
| WO | 2018022180 | A1 | 2/2018 |
| WO | 2018/138632 | A1 | 8/2018 |
| WO | 2019077218 | A1 | 4/2019 |
| WO | 2019232526 | A1 | 12/2019 |
| WO | 2019232527 | A1 | 12/2019 |
| WO | 2020/196336 | A1 | 10/2020 |
| WO | 2021/203910 | A1 | 10/2021 |
| WO | 2021/207821 | A1 | 10/2021 |
| WO | 2022/061117 | A1 | 3/2022 |
| WO | 2022/132351 | A1 | 6/2022 |
| WO | 2022/171349 | A1 | 8/2022 |

OTHER PUBLICATIONS

European Patent Office, Communication pursuant to Article 94(3) EPC for Application No. 19810895.3, dated Feb. 13, 2023 (3 pages).

Extended European Search Report of the European Patent Office, Application No. 19810895.3, dated Feb. 7, 2022, 10 pages.

Gagner, M., "Duodeno-Ileal Anastomosis with Self-Assembling Magnets: Initial Concepts and Basis of This Operation", Obesity Surgery 32, 932-933 (2022).

International Search Report and Written Opinion issued for Application No. PCT/US2016/031547 dated Oct. 18, 2016, 18 pages.

International Search Report and Written Opinion of the International Searching Authority, Application No. PCT/US2019035202, mailed Aug. 8, 2019, 6 pages.

International Search Report and Written Opinion of the International Searching Authority, Application No. PCT/US2022/25343, mailed Jul. 18, 2022, 14 pages.

International Search Report and Written Opinion of the International Searching Authority, Application No. PCT/US2022/25353, mailed Jun. 30, 2022, 12 pages.

International Search Report and Written Opinion of the International Searching Authority, for Application No. PCT/US2011/020229, with a date of mailing of Jun. 21, 2013, 6 pages.

International Search Report and Written Opinion of the International Searching Authority, for Application No. PCT/US2013/041641, dated Oct. 18, 2013, 4 pages.

International Search Report and Written Opinion of the International Searching Authority, for Application No. PCT/US2015/041498 dated Nov. 17, 2015, 17 pages.

International Search Report and Written Opinion of the International Searching Authority, for Application PCT/US2016/022209, dated May 30, 2016.

International Search Report and Written Opinion of the International Searching Authority, for Application PCT/US22/25338, dated Aug. 19, 2022, 14 pages.

International Search Report and Written Opinion of the International Searching Authority, for Application PCT/US23/29416, dated Dec. 7, 2023, 9 pages.

International Search Report and Written Opinion of the International Searching Authority, for Application PCT/US23/29432, dated Nov. 14, 2023, 7 pages.

Invitation to Pay Additional Fees and, Where Applicable, Protest Fee, from the International Search Authority, Application No. PCT/US2022/025338, mailed Jun. 23, 2022, 2 pages.

(56) References Cited

OTHER PUBLICATIONS

Invitation to Pay Additional Fees and, Where Applicable, Protest Fee, from the International Search Authority, Application No. PCT/US2022/025370, mailed Jun. 24, 2022, 3 pages.
Japanese Office Action for Japanese Patent Application No. 2021-034336 dated Dec. 17, 2021, 3 pages.
Japanese Office Action, Notice of Reasons for Refusal, Japanese Patent Application No. 2020-567134 dated Feb. 21, 2023.
Japanese Penultimate Office Action for Japanese Patent Application No. 2021-034336 dated Aug. 1, 2022, 9 pages.
Japanese Search Report, Japanese Application No. 2020-567134, dated Feb. 13, 2023, 28 pages.
Supplementary Partial European Search Report for Application No. EP 13793804.9 dated Jan. 15, 2016, 9 pages.
International Search Report and Written Opinion of the International Searching Authority, for Application PCT/2023/031863, dated Jan. 22, 2024, 8 pages.
International Search Report and Written Opinion of the International Searching Authority, for Application PCT/US2023/031861, dated Feb. 2, 2024, 9 pages.
International Search Report and Written Opinion of the International Searching Authority, for Application PCT/US2023/035976, dated Feb. 2, 2024, 11 pages.
Jamshidi, et al., "Magnamosis: magnetic compression anastomosis with comparison to suture and staple techniques," Journal of Pediatric Surgery, vol. 4, Issue 1, pp. 222-228. Jan. 20, 2009 (Jan. 20, 2009). [Retrieved on May 12, 2023]. Retrieved from the Internet: <URL: https://dotorg/10.1016/j.jpedsurg.2008.10.044>. entire document.

* cited by examiner

FIG. 45

Flexible Endoscopes General Diameter Guide for Endoscopy Brushes

| SCOPE TYPE | INSERTION TUBE OUTER DIAMETER | WORKING LENGTH | INSTRUMENT CHANNEL INTERNAL DIAMETER | HEALTHMARK ENDO BRUSHES | ENDOBRUSH DIAMETER RANGE | OLYMPUS COLOR GUIDE |
|---|---|---|---|---|---|---|
| **ADULTS** | | | | | | |
| GASTROSCOPE | 9.0 mm - 11.4 mm | 1030 mm - 1050 mm | 2.8mm - 3.8mm | CC-250, CC-374 | 2.6 - 3.2 mm<br>3.7 - 4.3 mm | |
| DUODENSCOPE | 10.8 mm - 12.5 mm | 1235 mm - 1250 mm | 3.2mm - 4.2mm | CC-250, CC374 | 2.6 - 3.2 mm<br>3.7 - 4.3 mm | |
| COLONOSCOPE | 12.9 mm - 13.7 mm | 1330 mm - 1680 mm | 3.7mm - 4.2mm | CC-374 | 3.7 - 4.3 mm | |
| SIGMOIDOSCOPE | 12.8 mm - 13.2 mm | 700 mm - 730 mm | 3.7mm - 4.2mm | CC-374 | 3.7 - 4.3 mm | |
| ENTEROSCOPE | 10.5 mm - 11.7 mm | 2200 mm - 2500 mm | 2.8mm - 3.8mm | CC-250, CC-374 | 2.6 - 3.2 mm<br>3.7 - 4.3 mm | |
| BRONCHOSCOPE | 5.7 mm - 6.0 mm | 550 mm - 600 mm | 2.0mm - 2.8mm | CC-172, CC-250 | 1.7 - 2.2 mm,<br>2.6 - 3.2 mm | |
| URETEROSCOPE | 2.8 mm - 3.3 mm | 670 mm - 700 mm | 1.2mm | CC-172 | 1,7 - 2.2 mm | |
| CYSTOSCOPE | 5.4 mm - 5.5 mm | 380 mm | 2.2mm - 2.4mm | CC-172, CC-250 | 1.7 - 2.2 mm,<br>2.6 - 3.2 mm | |
| RHINO-LARYNGOSCOPE | 2.6 mm - 4.9 mm | 300 mm - 365 mm | N/A - 2.0 | CC-172 | 1.7 - 2.2 mm | |
| LAPARO-THORACOSCOPE | 7.0 mm | 270 mm | 2.8 mm | CC-250 | 2.6 - 3.2 mm | |
| MOBILE AIRWAY SCOPE | 4.1 mm - 5.2 mm | 600 mm | 1.5 mm - 2.6 mm | CC-172, CC-250 | 1.7 - 2.2 mm,<br>2.6 - 3.2 mm | |
| CHOLEDOCHOSCOPE | 2.8 mm - 5.2 mm | 380 mm - 700 mm | 1.2 mm - 2.2 mm | CC-110, CC-172 | 1.2 mm,<br>1.7 - 2.2 mm | white |
| **PEDIATRICS** | | | | | | |
| GASTROSCOPE | 5.9 mm-6.0 mm | 1030 mm - 1050 mm | 2.0 mm | CC-172 | 1.7 - 2.2 mm | |
| COLONOSCOPE | 11.5 mm - 11. 6mm | 1680 mm - 1700 mm | 3.2 mm - 3.8 mm | CC-250, CC-374 | 2.6-3.2 mm<br>3.7 - 4.3 mm | |
| BRONCHOSCOPE | 4.4 mm - 5.1 mm | 600 mm | 2.0 mm | CC-172 | 1.7 - 2.2 mm | |

MECHANISM TO CREATE ENTEROTOMY BETWEEN ONE OR MORE COMPRESSION DEVICES

CROSS-REFERENCE TO RELATED APPLICATIONS

This patent application is a continuation of, and therefore claims priority from, International Patent Application No. PCT/US2022/025353 entitled MECHANISM TO CREATE LUMEN BETWEEN ONE OR MORE COMPRESSION DEVICES filed Apr. 19, 2022, which claims the benefit of U.S. Provisional Patent Application No. 63/177,192 entitled MECHANISM TO CREATE LUMEN BETWEEN ONE OR MORE COMPRESSION DEVICES filed Apr. 20, 2021 and U.S. Provisional Patent Application No. 63/257,933 entitled MECHANISM TO CREATE LUMEN BETWEEN ONE OR MORE COMPRESSION DEVICES filed Oct. 20, 2021, each of which is hereby incorporated herein by reference in its entirety.

The subject matter of this patent application may be related to the subject matter of U.S. patent application Ser. No. 17/108,840 entitled SYSTEMS, DEVICES, AND METHODS FOR FORMING ANASTOMOSES filed Dec. 1, 2020, which is a continuation-in-part of, and therefore claims priority from, International Patent Application No. PCT/US2019/035202 having an International Filing Date of Jun. 3, 2019, which claims the benefit of, and priority to, U.S. Provisional Application Ser. No. 62/679,810, filed Jun. 2, 2018, U.S. Provisional Application Ser. No. 62/798,809, filed Jan. 30, 2019, and U.S. Provisional Application Ser. No. 62/809,354, filed Feb. 22, 2019, the contents of each of which are hereby incorporated by reference herein in their entireties.

FIELD OF THE INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Thus, there still remains a clinical need for reliable devices and minimally-invasive procedures that facilitate compression anastomosis formation between tissues in the human body.

SUMMARY

Various embodiments of the invention provide improved devices and techniques for minimally-invasive formation of anastomoses within the body. Such devices and techniques facilitate faster and less-expensive treatments for chronic diseases such as obesity and diabetes. Such techniques also reduce the time and pain associated with palliative treatments for diseases such as cancers.

For example, in some embodiments, an apparatus for the placement of a compression anastomosis device comprises a delivery device from which one or more compression anastomosis devices may be deployed from and a control member which may be deployed from the distal end of the delivery device. The control member may be manipulable such that it aligns with the one or more compression anastomosis devices within a deployment channel of the delivery device.

In various other embodiments, the control member may be expandable such that it may expand to a diameter greater than that of the deployment channel of the delivery device in order to dilate a created enterotomy. The control member may also be contractable such that it may be contracted to a diameter less than or equal to that of the deployment channel in order to be removed from a patient.

In some embodiments, the control member may be a basket, balloon cuff, and/or wire jaw shape.

The control member may, in some embodiments, be deployed between distal and proximal lumens in order to capture a formed enterotomy. The control member may also be deployed into a distal side of a distal anastomosis device in order to act as a backstop control device.

In various embodiments, a piercing device may be deployable from the delivery device, and capable of piercing, dissecting, and/or dilating tissue to create a deployment channel between two lumens. In some embodiments, the piercing device may be a hot needle, a hot tip emitting monopolar energy, a coring needle, and/or a corkscrew.

Various embodiments may include a method for positioning a compression anastomosis device comprising deploying a first compression anastomosis device from a distal end of a delivery device into a proximal lumen. The first anastomosis device may then be positioned against a tissue wall, and the tissue may be pierced to create an enterotomy into a distal lumen. A control member may then be deployed into the enterotomy, and subsequently expand the enterotomy. The control member may then engage with a second anastomosis device, and the control member may be manipulated rotationally and/or laterally with respect to the distal anastomosis device so as to align the two anastomosis devices. The anastomosis devices may then be brought together so as to capture the enterotomy. In some embodiments, the control member may then be contracted to a diameter less than or equal to that of the delivery device, and retracted into the delivery device for removal from the patient.

In various embodiments, the control member may be deployed between anastomosis devices so as to capture the enterotomy.

In other embodiments, an apparatus for placing a compression anastomosis device comprises a delivery device having capabilities to cut, dissect, and/or dilate tissue to create an enterotomy between adjacent lumens. A control member may be deployable from the distal end of the delivery device into the enterotomy to capture the enterotomy. The control member may also be expandable to a diameter greater than that of the enterotomy in order to dilate the enterotomy. The control member may also be manipulable rotationally and/or laterally so as to engage with a distally deployed anastomosis device and align the distal anastomosis device with a proximal anastomosis device and pair them. The control member may then be retractable to a diameter less than or equal to that of the delivery device and retractable into the delivery device.

In some embodiments, the control member may be deployable to the distal side of a distal anastomosis device so as to act as a backstop.

In various embodiments, the control member may be a basket, balloon cuff, and/or wire jaw shape.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 9 illustrates the use of monopolar energy for piercing and accessing the gallbladder.

FIG. 10 illustrates the use of a fine aspiration needle (FNA) for piercing and accessing the gallbladder.

FIG. 11 illustrates the use of a corkscrew-type needle for piercing and accessing the gallbladder.

FIG. 12 illustrates the use of a guidewire passed through the bile duct into the gallbladder.

FIG. 14 illustrates a T-bar member. FIG. 15 illustrates a nitinol coil (e.g., "pig tail"). FIG. 16 illustrates a balloon member of a catheter. FIG. 17 illustrates a malecot catheter.

FIG. 45 provides a listing of some exemplary working channel sizes considered usable/feasible to deploy a magnetic array with a cage to produce an anastomosis.

Figure 1:
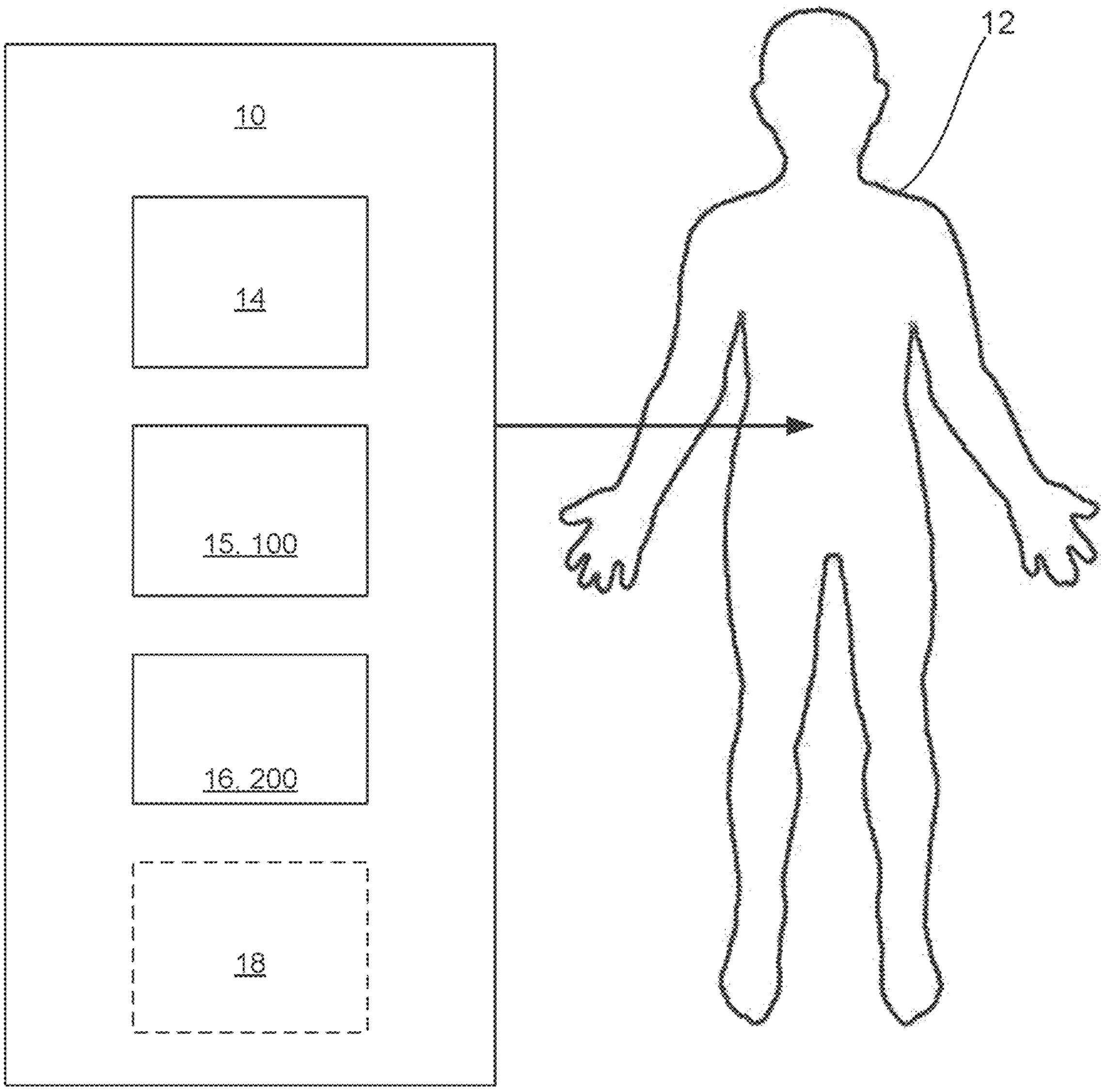
FIG. 1 is a schematic illustration of an anastomosis formation system consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

Exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

Illustrative embodiments significantly improve compression anastomosis device placement by deploying a control member to engage a distal anastomosis device, orient the magnetic poles of the device, and bring a pair of anastomosis devices together.

In an exemplary embodiment, a deployment device deploys an anastomosis device into a proximal lumen, and subsequently pierces through an adjacent wall to the lumen, into a distal lumen. The deployment device then deploys a distal anastomosis device into the distal lumen. The control member is deployed into the space between the lumens and, having been in a contracted position in the deployment device, expands to a size greater than the hole between the lumens, thus expanding the enterotomy. The control member then engages with the distal anastomosis device, orienting the poles to compliment those of the proximal anastomosis device, and exerts force to bring the devices together. The control member is then contracted to its original size and removed from the lumens into the deployment device.

The system generally includes an access device configured to be provided within a hollow body of a patient and assist in the formation of an anastomosis at a target site (a desired anatomical location) within the hollow body for formation of an anastomosis between a first portion of tissue of the hollow body at the target site and a second portion of tissue of the hollow body. The access device is configured to provide access to the first and second portions of tissue of the hollow body and further deliver and position first and second implantable magnetic anastomosis devices relative to the first and second portions of tissue or adjacent tissue for the formation of an anastomosis between tissues at the target site. The first and second implantable magnetic anastomosis devices are configured to be magnetically attracted to one another through a defined tissue area of the combined thickness of a wall of the tissues at the target site and exert compressive forces on the defined area to form the anastomosis.

The systems, devices, and methods described herein include, but are not limited to, various access devices for accessing a hollow body of the patient, such as a gallbladder, and a control member for securing positioning of the access device for the subsequent placement of one of a pair of magnetic anastomosis compression devices. The systems, devices, and methods described herein further include various delivery devices for delivering at least one of the pair of magnetic anastomosis compression devices to the target site, wherein, in some instances, a delivery device consistent with the present disclosure may assist in the deployment of at least one of the pair of magnetic anastomosis compression devices and subsequent securing to the target site and/or coupling the pair of magnetic anastomosis compression devices to one another. The systems, devices, and methods described herein include various embodiments of control members for securing placement of magnetic anastomosis compression devices and various designs for transitioning from a compact delivery configuration to a larger deployed configuration, generally by way of self-assembling design.

More specifically, exemplary embodiments provide a system including a delivery device for introducing and delivering, via a minimally-invasive technique, a pair of magnetic assemblies between adjacent organs to bridge walls of tissue of each organ together to thereby form a passage therebetween (i.e., an anastomosis). The delivery device is particularly useful in delivering the pair of magnetic assemblies to a target site within the gastrointestinal tract to thereby form anastomosis between gastric and gallbladder walls to provide adequate drainage from the gallbladder when blockage is occurring (due to disease or other health-related issues). The system also includes a control member for aligning and pairing a set of compression anastomosis devices at the desired target site.

Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as stomach or colon cancer.

FIG. 1 is a schematic illustration of an anastomosis formation system 10 for providing improved placement of magnetic anastomosis devices 16, 200 at a desired site so as to improve the accuracy of anastomoses creation between tissues within a patient 12. The system 10 generally includes an access device 14, a delivery device 15, 100, magnetic anastomosis devices 16, 200, and an imaging modality 18.

The access device 14 may generally include a scope, including, but not limited to, an endoscope, laparoscope, catheter, trocar, or other delivery device. For most applications described herein, the access device 14 is an endoscope, including a delivery needle configured to deliver the magnetic anastomosis devices 16, 200. Accordingly, the system 10 of the present disclosure relies on a single endoscope 14 for the delivery of the two magnetic devices 16, 200. As will be described in greater detail herein, a surgeon may advance the endoscope 14 within a hollow body of the patient 12 and position the endoscope 14 at the desired anatomical location for formation of the anastomosis based on a visual depiction of the location of the target site as provided by an imaging modality. For example, the imaging modality may include a display in which an image, or other visual depiction, is displayed to the surgeon illustrating a target site when performing a medical imaging procedure, including, but not limited to, ultrasound (US), wavelength detection, X-ray-based imaging, illumination, computed tomography (CT), radiography, and fluoroscopy, or a combination thereof. The surgeon may then rely on such a visual depiction when advancing the endoscope through the hollow body so as to position the access device 14 at a portion of tissue adjacent to the other portion of tissue at the target site, thereby ensuring the placement of the magnetic devices 16, 200 is accurate.

It should be noted that the hollow body through which the access device 14 may pass includes, but is not limited to, the stomach, gallbladder, pancreas, duodenum, small intestine, large intestine, bowel, vasculature, including veins and arteries, or the like.

Figure 2:
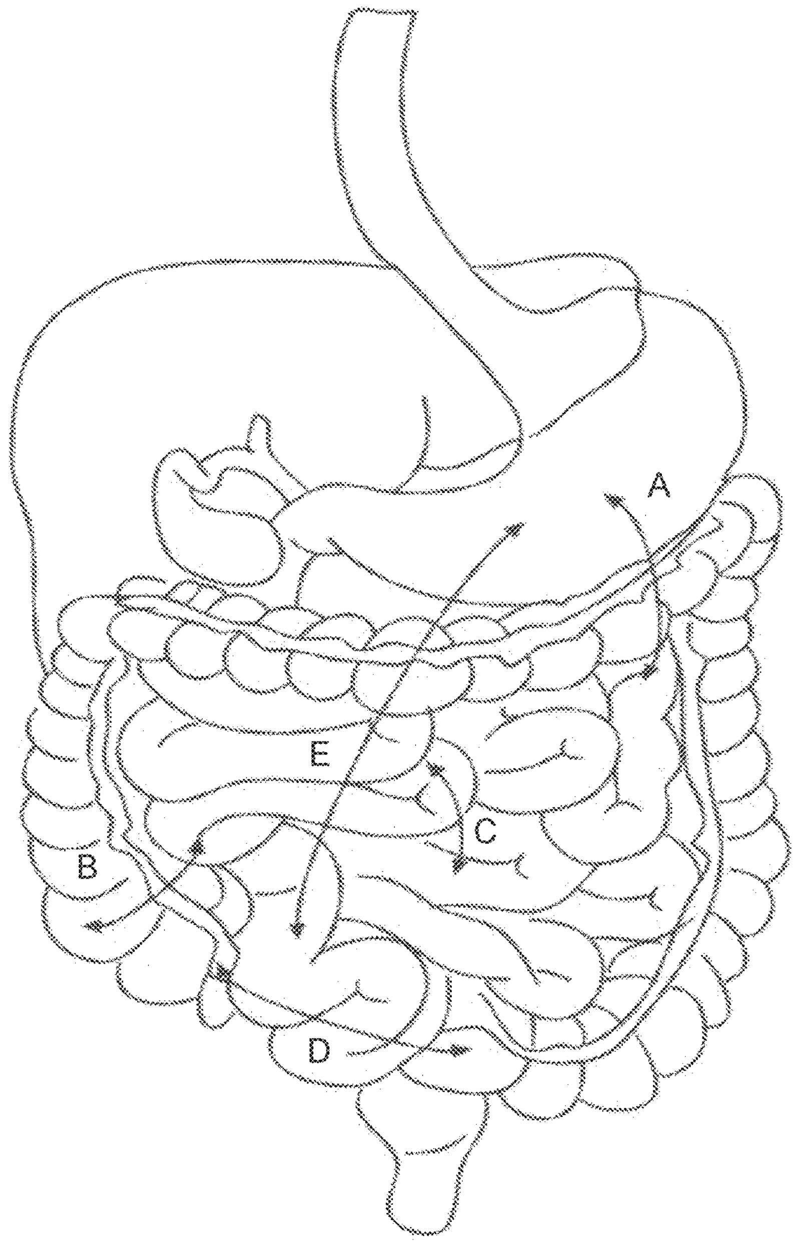
FIG. 2 shows several potential anatomical targets for anastomosis formation, where arrow A is stomach to small intestine, arrow B is small intestine to large intestine, arrow C is small intestine to small intestine, arrow D is large intestine to large intestine, and arrow E is stomach to large intestine.

In some embodiments, self-assembling magnetic devices are used to create a bypass in the gastrointestinal tract. Such bypasses can be used for the treatment of a cancerous obstruction, weight loss or bariatrics, or even treatment of diabetes and metabolic disease (i.e. metabolic surgery). FIG. 2 illustrates the variety of gastrointestinal anastomotic targets that may be addressed with the devices of certain exemplary embodiments, such targets include stomach to small intestine (A), stomach to large intestine (E), small intestine to small intestine (C), small intestine to large intestine (B), and large intestine to large intestine (D). Accordingly, exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as stomach or colon cancer.

For example, if the hollow body through which the access device 14 may pass is a bowel of the patient, the first portion may be a distal portion of the bowel and the second portion may be a proximal portion of the bowel. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculo-skeletal disease. It should be noted that the system may be used for the formation of an anastomosis between a first portion of tissue of the hollow body at the target site and an adjacent tissue of a second hollow body (e.g., portal between the stomach and the gallbladder, the duodenum and the gallbladder, stomach to small intestine, small intestine to large intestine, stomach to large intestine, etc.).

Figure 3:
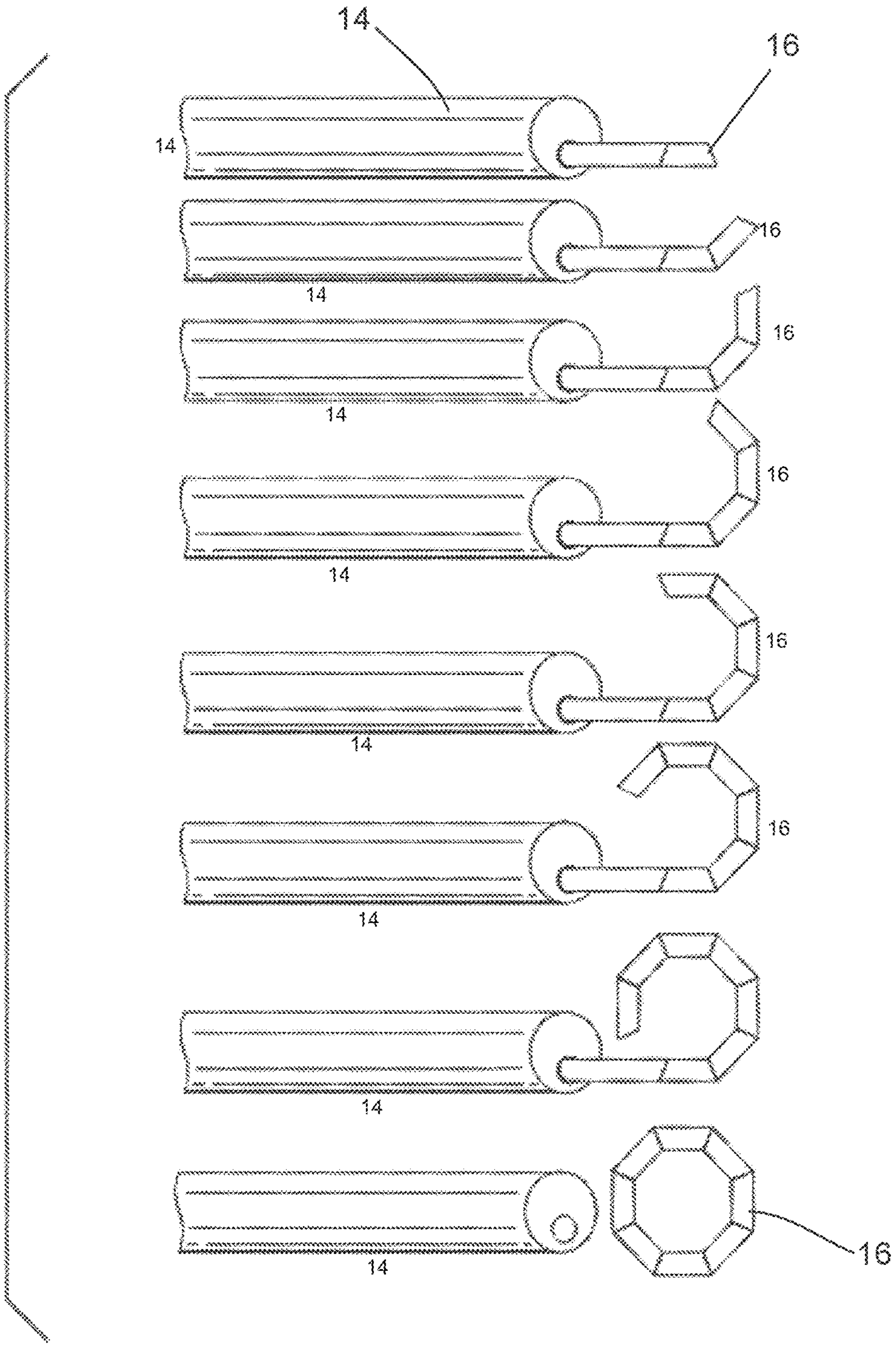
FIG. 3 shows an exemplary magnetic anastomosis device delivered through an endoscope instrument channel such that the individual magnet segments self-assemble into a larger magnetic structure—in this particular case, an octagon.

In an endoscopic procedure, the self-assembling magnetic devices can be delivered using a single endoscope 14. Deployment of a magnetic device 16 is generally illustrated in FIG. 3. As shown, exemplary magnetic anastomosis devices 16 may be delivered through an endoscope 14 such that individual magnet segments self-assemble into a larger magnetic structure—in this particular case, an octagon. When used with the techniques described herein, the devices 16 allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. For example, in some cases, resulting anastomosis may have a 1:1 aspect ratio relative to the final dimensions of the assembled magnetic devices. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. However, the magnetic assembly design of exemplary embodiments overcome such limitations. For example, the design of the magnetic assembly, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater. Such aspect ratios are described in greater detail with regard to FIGS. 44A, 44B, 44C, and 44D.

Because the magnetic devices are radiopaque and echogenic, the devices 16 can be positioned using fluoroscopy, direct visualization (trans-illumination or tissue indentation), and ultrasound, e.g., endoscopic ultrasound. The devices 16 can also be ornamented with radiopaque paint or other markers to help identify the polarity of the devices during placement.

The magnetic anastomosis devices 16 generally comprise magnetic segments that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope 14 or similar device. Additionally, the delivery conformation is typically somewhat flexible so that the device can be guided through various curves in the body. Once the device is delivered, the device will assume a deployed configuration of the desired shape and size by converting from the delivery configuration to the deployed configuration automatically. The self-conversion from the delivery configuration to the deployment configuration is directed by coupling structures that cause the magnetic segments to move in the desired way without intervention. Exemplary self-assembling magnetic anastomosis devices 16, such as self-closing, self-opening, and the like, are described in U.S. Pat. Nos. 8,870,898, 8,870,899, 9,763,664, and 10,182,821, the contents of each of which are incorporated by reference herein in their entirety.

Figure 4A:
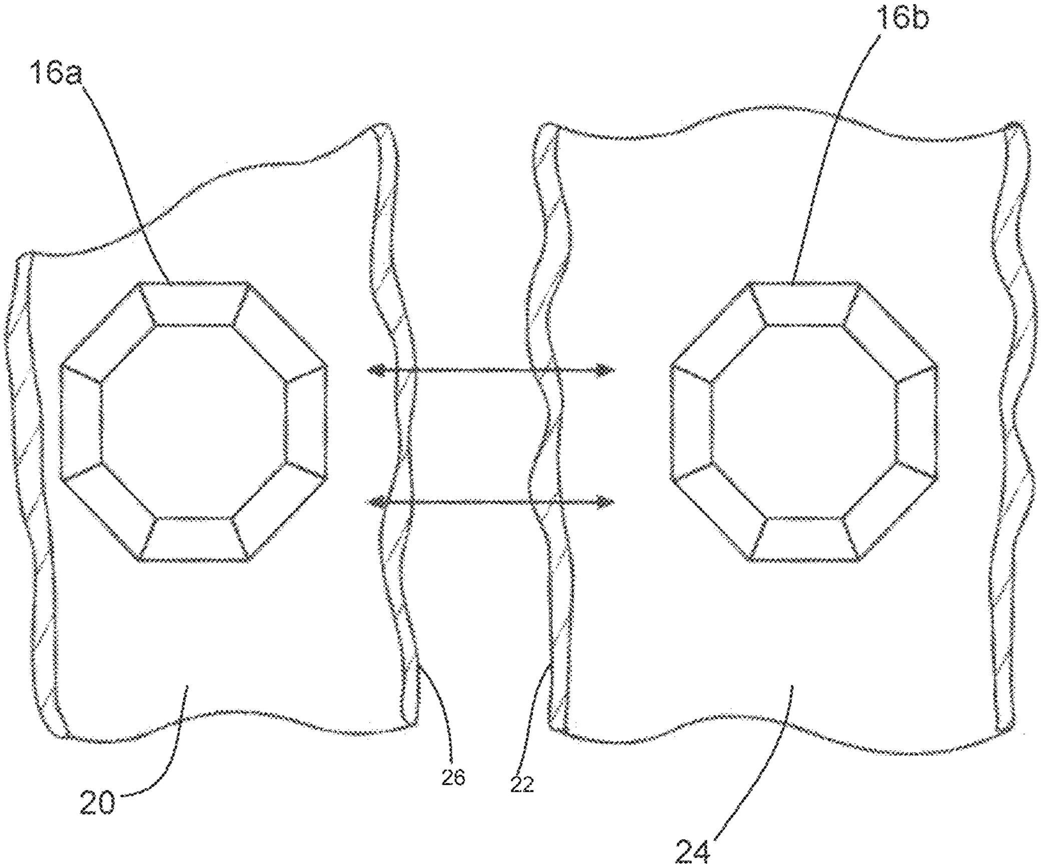
FIG. 4A depicts two magnetic anastomosis devices attracting each other through tissue. As shown, the devices each comprise eight magnetic segments, however alternate configurations are possible.

In general, as shown in FIG. 4A, a magnetic anastomosis procedure involves placing a first and a second magnetic structures 16*a*, 16*b* adjacent to first and second portions 20, 24 of tissues 26, 22, respectively, thus causing the tissues 22 and 26 to come together. Once the two devices 16*a*, 16*b* are brought into proximity, the magnetic structures 16*a*, 16*b* mate and bring the tissues 22, 26 together. Once the two devices 16*a*, 16*b* mate, the tissue that is trapped between the devices will necrose, causing an anastomosis to form. Alternatively, the tissue 22, 26 bound by the devices 16*a*, 16*b* may be perforated after the devices mate to create an immediate anastomosis. With time, an anastomosis of the size and shape of the devices 16*a*, 16*b* will form and the devices will fall away from the tissue 22, 26.

Figure 4B:
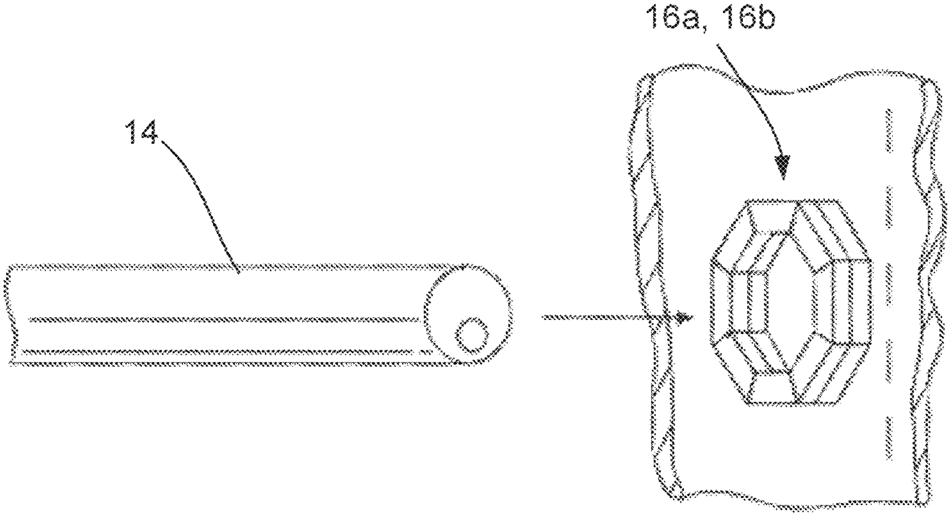
FIG. 4B shows the two magnetic anastomosis devices coupled together by magnetic attraction, capturing the intervening tissue.

Alternatively, because the mated devices 16*a*, 16*b* create enough compressive force to stop the blood flow to the tissues 22, 26 trapped between the devices, a surgeon may create an anastomosis by making an incision in the tissues 22, 26 circumscribed by the devices, as shown in FIG. 4B. In some instances, the endoscope can be used to cut through the circumscribed tissue.

In yet another embodiment, as will be described in greater detail herein, and shown in FIGS. 43A-43I, a surgeon may first cut into, or pierce, the tissues 22, 26, and then deliver a magnetic device 16*a*, 200*a* into a portion 20 of the hollow body so as to place device 16*a*, 200*a* around the incision on tissue 22. The surgeon may then place device 16*b*, 200*b* into portion 24 of the hollow body so as to deliver device 16*b*, 200*b* around the incision on tissue 26, and then allow the devices 16*a*, 200*a* and 16*b*, 200*b* to couple to one another, so that the devices 16*a*, 16*b* (200*a*, 200*b*) circumscribe the incision. As before, once the devices 16*a*, 16*b* (200*a*, 200*b*) mate, the blood flow to the incision is quickly cut off.

While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier. Yet still, in other embodiments, such as magnetic assembly 200 of FIG. 42, a magnetic assembly may comprise a pair of magnetic segments generally arranged in a linear alignment with one another (e.g., aligned in an end-to-end fashion) and coupled together via a flexible exoskeleton element. Such an embodiment will be described in greater detail herein.

Figure 5A:
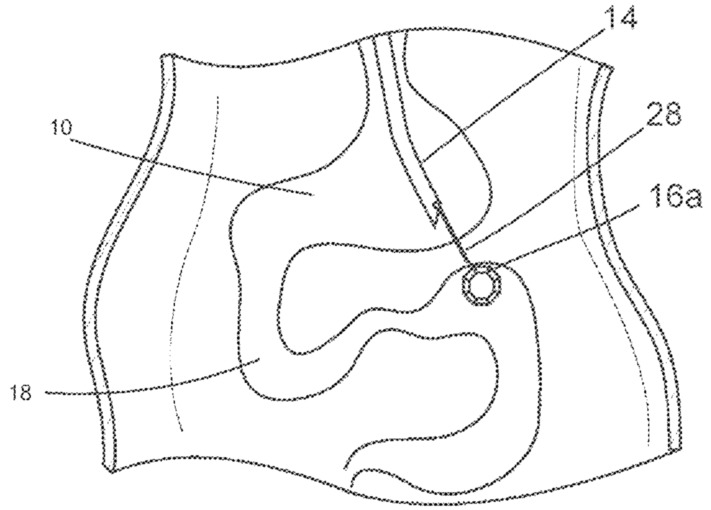
FIG. 5A shows the needle delivering a first magnetic device into a first portion of the hollow body at the target site.
Figure 5B:
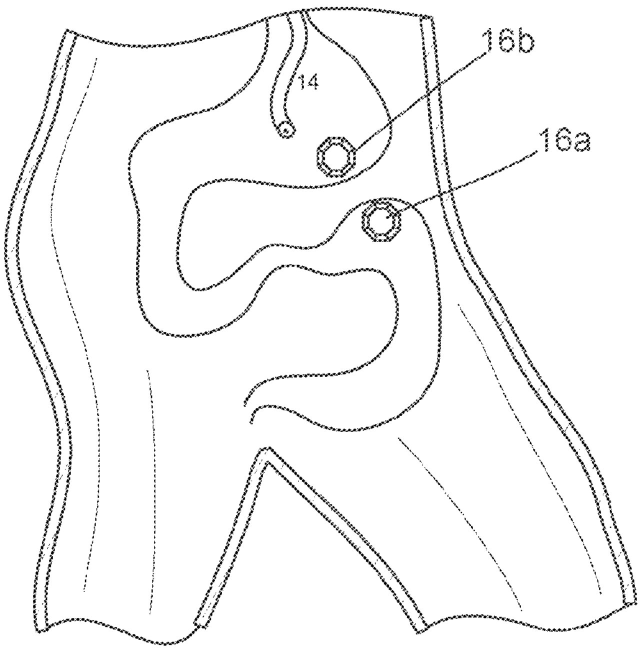
FIG. 5B shows subsequent deployment to of a second magnetic device into a second portion of the hollow body adjacent to the target site.

As previously described, the self-assembling magnetic anastomosis devices can be delivered to the target site via the access device 14. For example, as shown in FIG. 5A, the access device 14 may include a delivery needle 28 (e.g., an aspiration needle) used to deliver the first magnetic anastomosis device 16*a* into the lower small intestine (through the puncture), which is then followed by deployment to of a second magnetic device 16*b* into the upper small intestine at a location on the tissue adjacent to the target site (shown in FIG. 5B). It should be noted that the delivery can be guided with fluoroscopy or endoscopic ultrasound. Following self-assembly, these small intestine magnetic devices 16*a*, 16*b* couple to one another (e.g., magnetically attracted to one another) through a defined tissue area of the combined thickness of a wall of the tissues at the target site and exert compressive forces on the defined area to form the anastomosis.

Figure 6A:
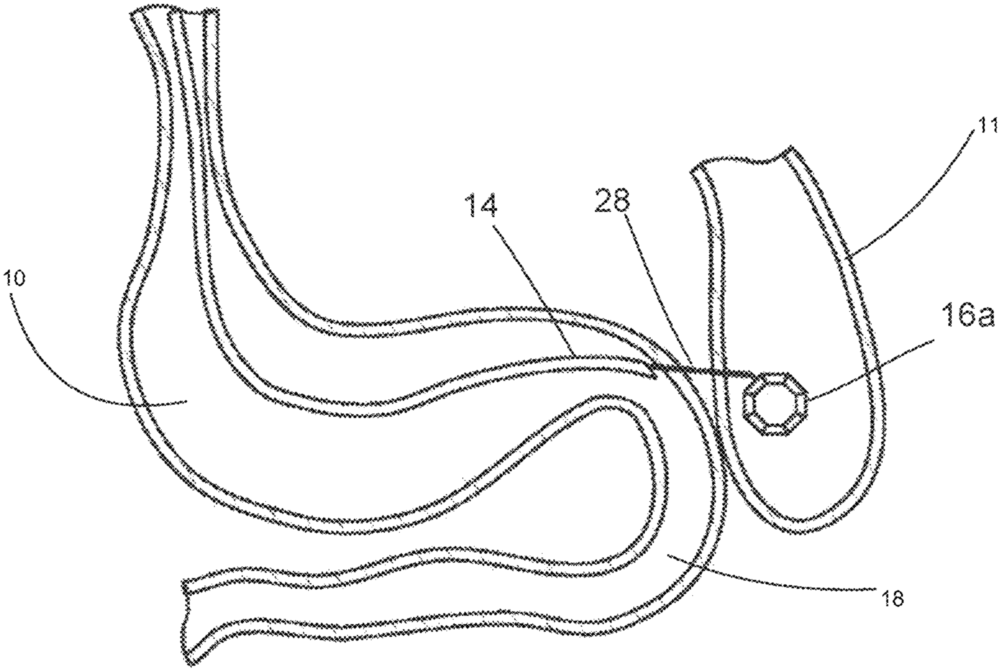
FIG. 6A shows endoscopic ultrasound guided needle delivery of a magnet assembly into the gallbladder which then couples with a second magnet assembly in the stomach or duodenum as shown in FIG. 6B.
Figure 6B:
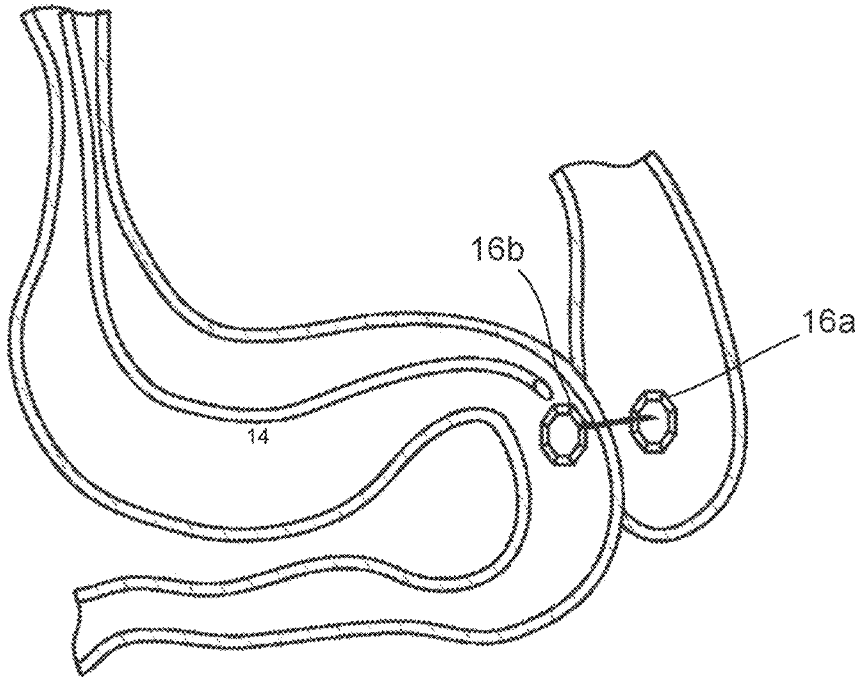

FIG. 6A shows endoscopic ultrasound guided needle delivery of a magnet assembly into the gallbladder which then couples with a second magnet assembly in the stomach or duodenum as shown in FIG. 6B. Accordingly, the described procedures may also be used with procedures that remove or block the bypassed tissues. For example, endoscopic ultrasound (EUS) can be used to facilitate guided transgastric or transduodenal access into the gallbladder for placement of a self-assembling magnetic anastomosis device. Once gallbladder access is obtained, various strategies can be employed to maintain a patent portal between the stomach 10 and the gallbladder 11 or the duodenum 76 and the gallbladder 11. In another embodiment, gallstones can be endoscopically retrieved and fluid drained. For example, using the described methods, an anastomosis can be created between the gallbladder and the stomach. Once the gallbladder is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g. ethanolamine or ethanol).

Figure 7:
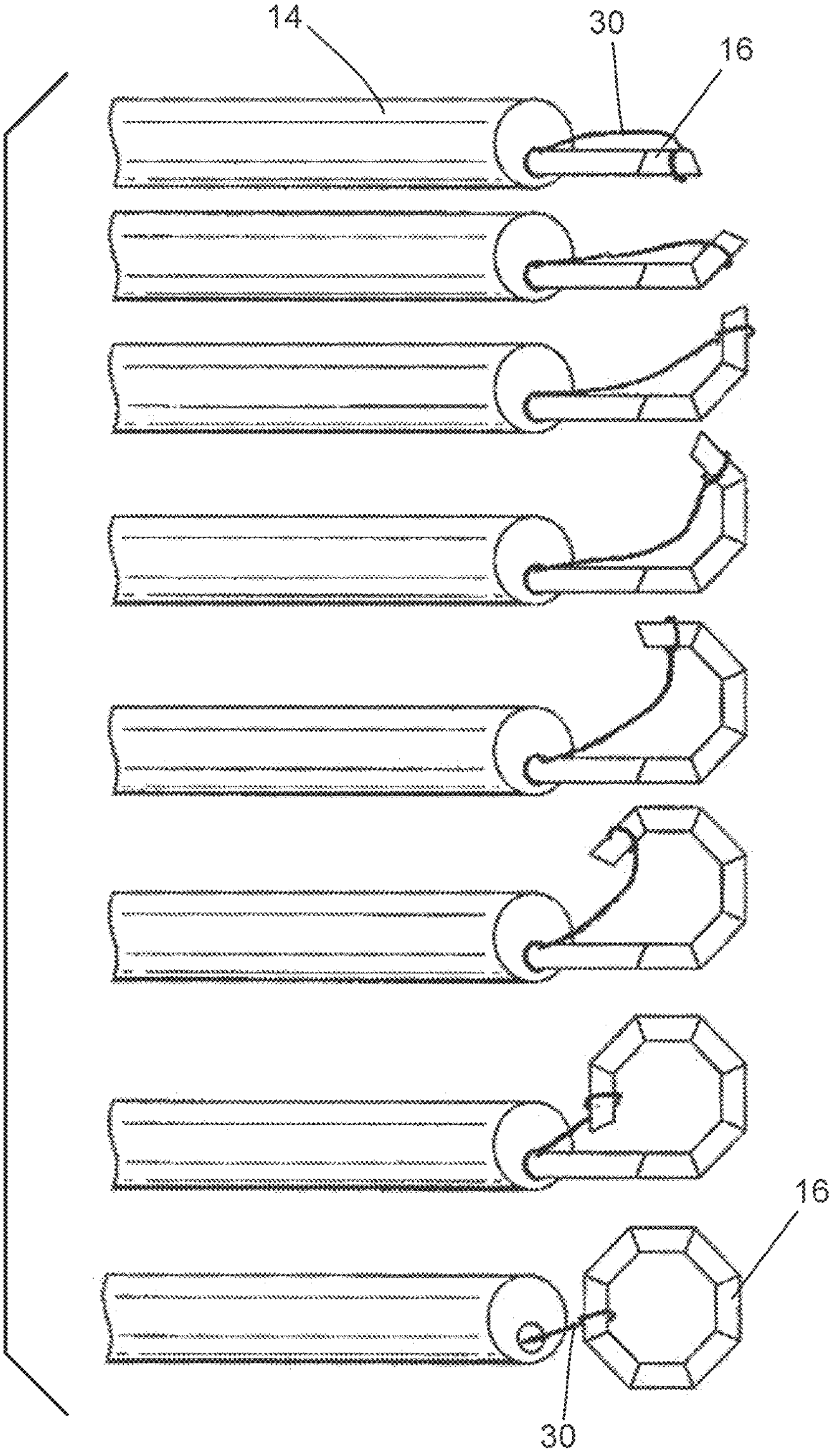
FIG. 7 illustrates a single guide element for deploying and manipulating a magnetic anastomosis device.
Figure 8A:
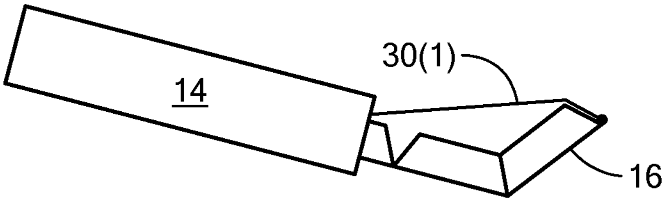
FIGS. 8A, 8B, 8C, 8D, 8E, and 8F each depict the deployment of the self-closing magnetic anastomosis device with a plurality of guide elements.
Figure 8B:
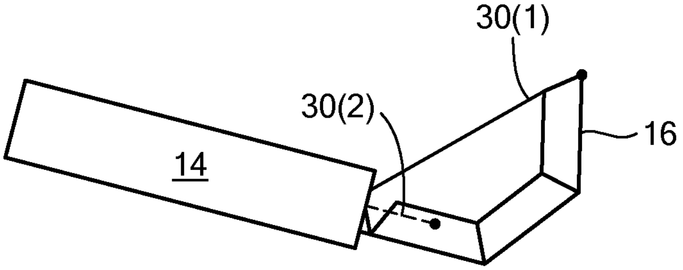
Figure 8C:
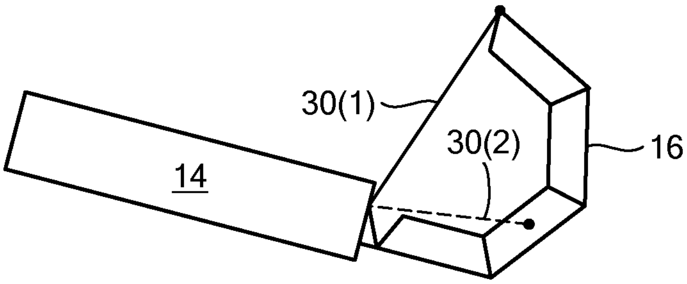
Figure 8D:
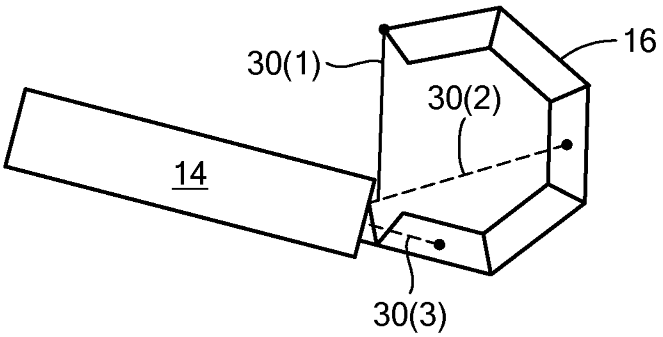
Figure 8E:
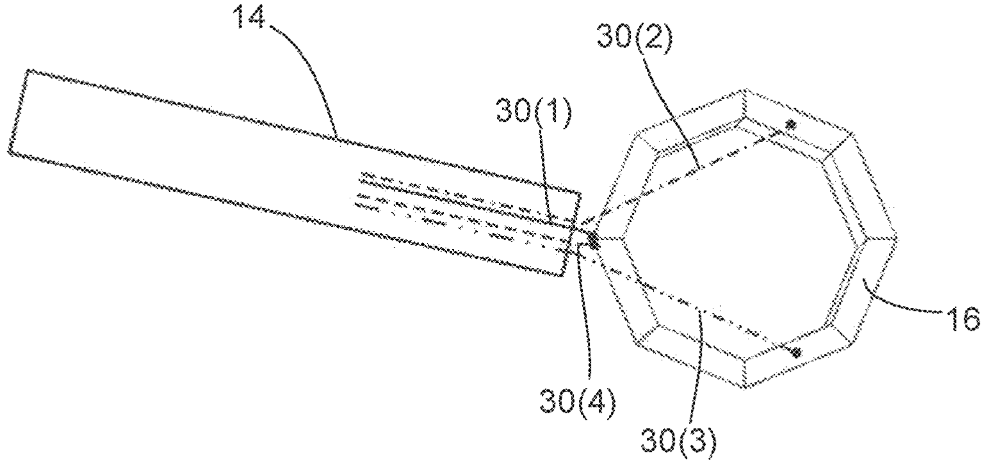
Figure 8F:
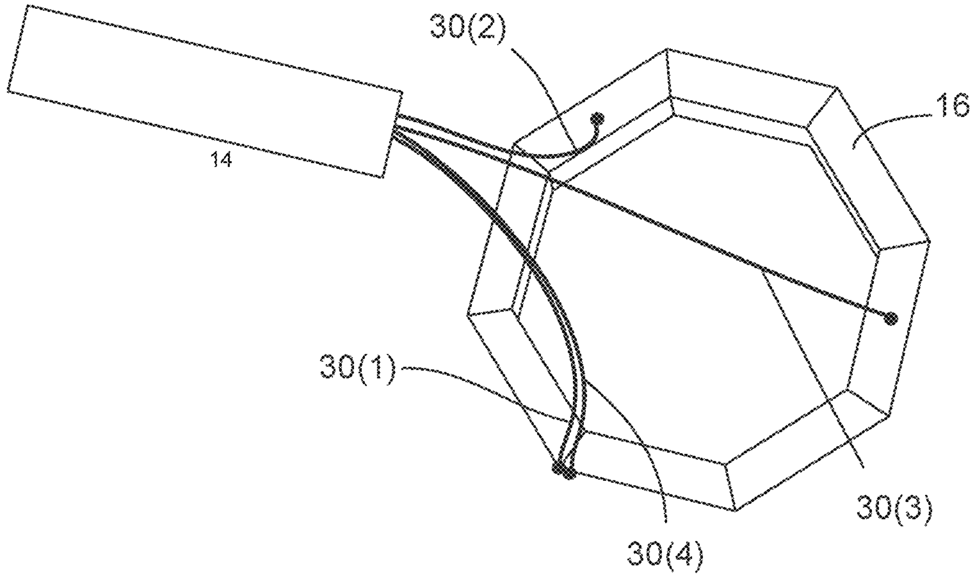

FIG. 7 illustrates a single guide element 30 for deploying and manipulating a magnetic anastomosis device 16. For example, once the self-assembling magnetic device has been delivered to a tissue, it is beneficial to be able to manipulate the location of the device 16. While the device 16 can be manipulated with conventional tools such as forceps, it is often simpler to manipulate the location of the deployed device 16 with a guide element 30, such as a suture or wire. As shown in FIGS. 7 and 8A-8F, a variety of attachment points can be used to provide control over the location and deployment of a self-assembling magnetic anastomosis device 16. For example, as shown in FIG. 7, the guide element 30 may be coupled to a single distal segment such that, upon self-assembly, the single distal segment results in an attachment point that provides translational freedom of movement. It is also notable that the configuration shown in FIG. 7 also allows a closing force to be applied to the distal-most segment. That is, in the event that one or more segments should become entangled with tissue, or otherwise prevented from self-assembling, a proximal pulling force with the guide element 30 can help the device 16 to complete self-assembly. Once self-assembly is completed, the device 16 can be positioned with the guide element 30 to be mated with another device (not shown) to form an anastomosis, as described above. While it is not shown in FIG. 7, it is envisioned that additional structures, such as a solid pusher or a guide tube can be used to deploy the device 16 in the desired location and a control member can be used to orient and mate the device 16.

The guide element 30 can be fabricated from a variety of materials to achieve the desired mechanical properties and bio-compatibility. The guide element 30 may be constructed from metal, e.g., wire, stainless steel wire or nickel alloy wire. The guide element may be constructed from natural fibers, such as cotton or an animal product. The guide element may be constructed from polymers, such as biodegradable polymers, or polymers including repeating lactic acid, lactone, or glycolic acid units, such as polylactic acid (PLA). The guide element may also be constructed from high-tensile strength polymers, such as Tyvek™ (high density polyethylene fibers) or Kevlar™ (para-aramid fibers). In an embodiment, guide element 30 is constructed from biodegradable suture, such as VICRYL™ (polyglactin 910) suture available from Ethicon Corp., Somerville, N.J.

In some embodiments, a magnetic anastomosis device 16 may include multiple guide elements 30. For example, as shown in FIGS. 8A, 8B, 8C, 8D, 8E, and 8F, a variety of attachment points can be used to provide control over the location and deployment of a self-assembling magnetic anastomosis device 16. As shown, four guide elements 30(1)-30(4) may be coupled to four separate segments of the device 16, respectively. Each guide element may include a distal end coupled to a respective portion of the anastomosis device, and a proximal end that can be manipulated (i.e., increased or decreased tension) to thereby manipulate the positioning and orientation of the anastomosis device once it has self-assembled into the predetermined shape (i.e., a polygon). For example, as shown, guide element 30(1) is coupled to the most distal end segment, guide elements 30(2) and 30(3) are coupled to middle segments (segments between the most distal end segment and most proximal end segment), and guide element 30(4) is coupled to the most proximal end segment.

Figure 9:
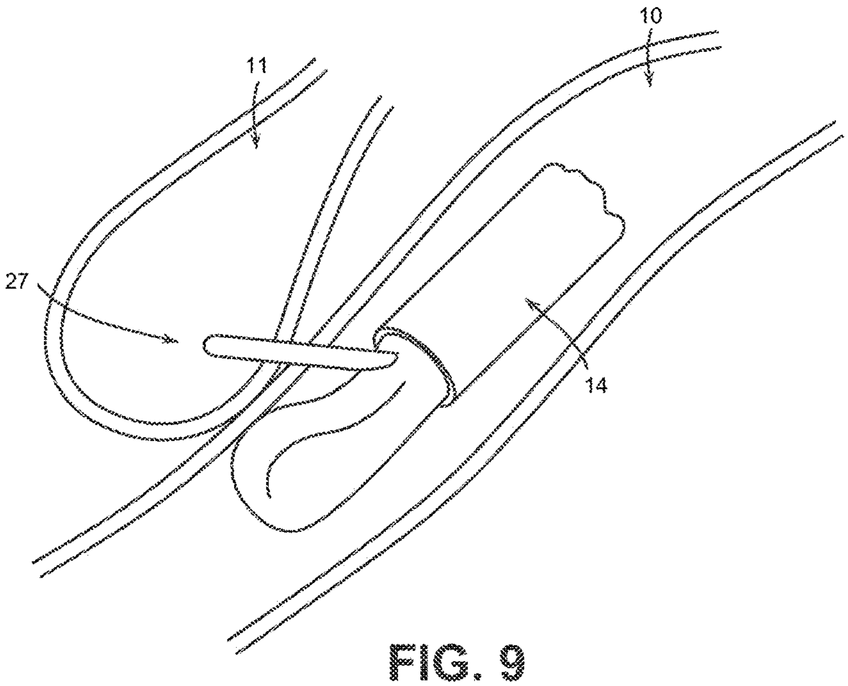
FIGS. 9, 10, 11, and 12 illustrate various methods of accessing the target site, specifically accessing a gallbladder via an endoscopic ultrasound guided procedure.

FIGS. 9-12 illustrate various methods of accessing the target site, specifically accessing a gallbladder via an endoscopic ultrasound guided procedure. FIG. 9 illustrates the use of monopolar energy for piercing and accessing the gallbladder 11. An endoscopic ultrasound scope (EUS scope) 14 accesses the stomach 10/duodenum 76. A hot probe or guide wire utilizing monopolar or bipolar energy pierces the tissue of the stomach 10/duodenum 76 and the gallbladder 11 in order to deliver an anastomosis device 16.

Figure 10:
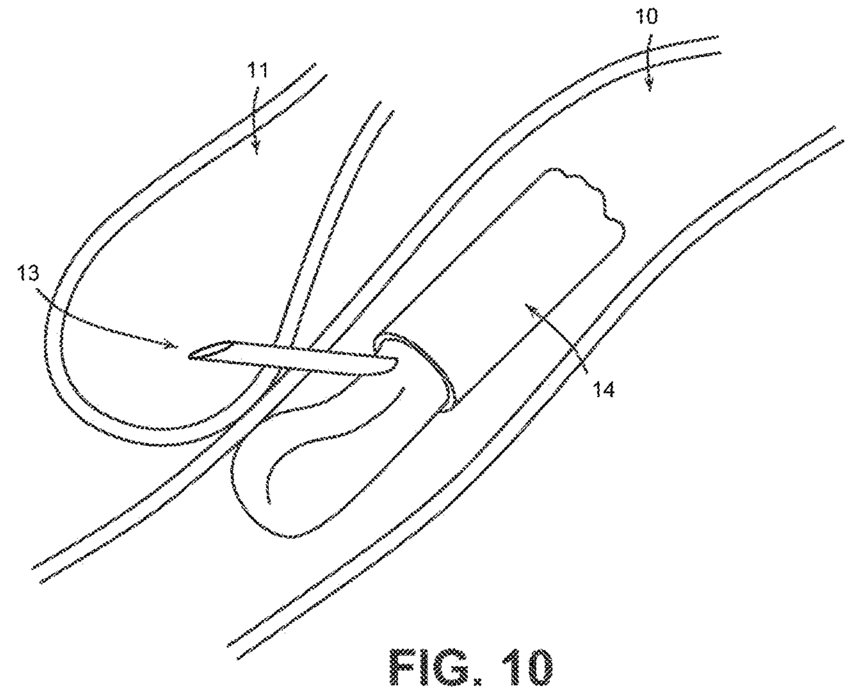

FIG. 10 illustrates the use of a fine aspiration needle (FNA) for piercing and accessing the gallbladder 11. An FNA 14 accesses the stomach 10/duodenum 76. A hypotube with a cutting edge pierces the tissue of the stomach 10/duodenum 76 and the gallbladder 11 in order to deliver an anastomosis device 16.

Figure 11:
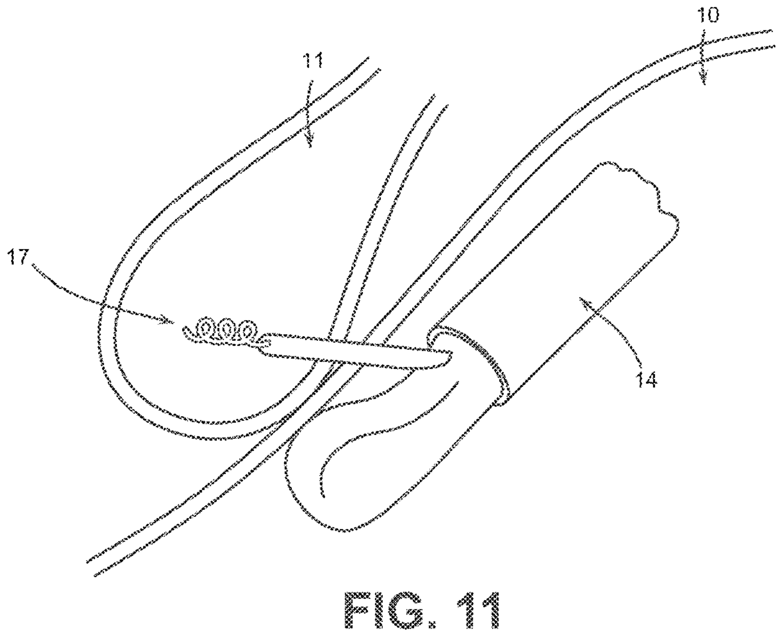

FIG. 11 illustrates the use of a corkscrew-type needle 17 for piercing and accessing the gallbladder 11. An EUS scope 14 accesses the stomach 10/duodenum 76. A cork screw needle 17 pierces the tissue of the stomach 10/duodenum 76 and the gallbladder 11 in order to deliver an anastomosis device 16.

Figure 12:
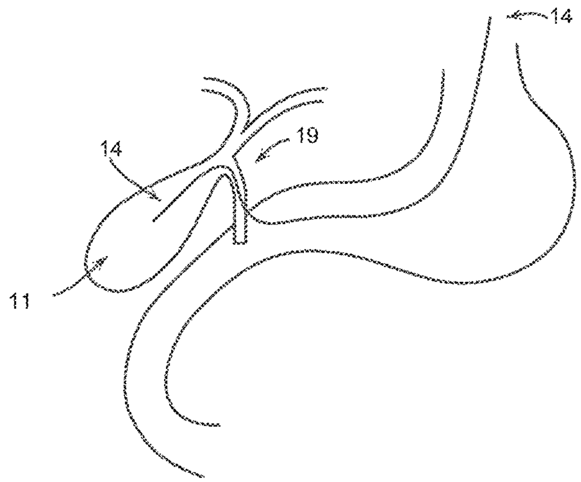

FIG. 12 illustrates the use of a guidewire 14 passed through the bile duct 19. Guide wire 14 accesses the stomach 10/duodenum 76. A guide wire 14 pierces the tissue of the stomach 10/duodenum 76 into the bile duct 19 in order to deliver an anastomosis device 16 in the gallbladder 11.

Figure 13:
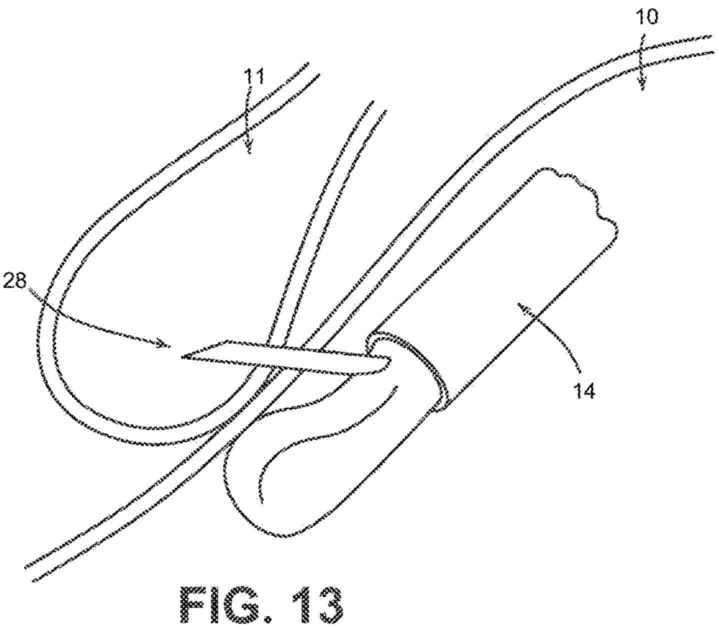
FIG. 13 shows endoscopic ultrasound guided needle piercing of the gallbladder to access the interior of the gallbladder for subsequent delivery of a magnet assembly therein.

FIG. 13 shows EUS scope 14 with an access needle 28 piercing the stomach 10/duodenum 76 and gallbladder 11 to access the interior of the gallbladder 11 for subsequent delivery of a magnet assembly 16 therein.

Figure 14:
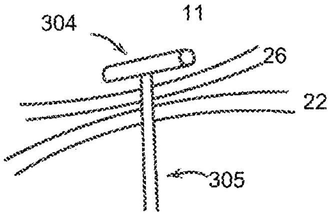
FIGS. 14, 15, 16 and 17 illustrate various devices for anchoring the access device and/or delivery device to the target site at the gallbladder.

FIGS. 14, 15, 16 and 17 illustrate various devices for anchoring the access device and/or delivery device to the target site at the gallbladder 11. FIG. 14 illustrates a T-bar member 304 tethered to the delivery device 14 by a tether 305 acting as an anchoring device to bring the tissues 22, 26 together.

Figure 15:
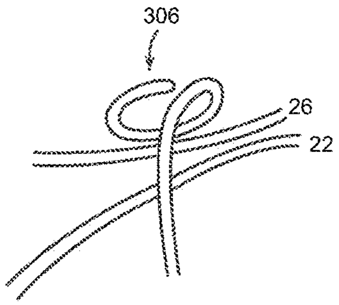

FIG. 15 illustrates a preformed nitinol coil (e.g., "pig tail") 306 acting as an anchoring device to bring the tissues 22, 26 together.

Figure 16:
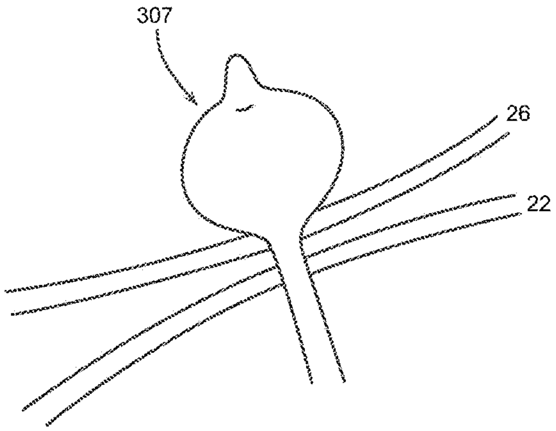

FIG. 16 illustrates a balloon member of a catheter 307 acting as an anchoring device to bring the tissues 22, 26 together.

Figure 17:
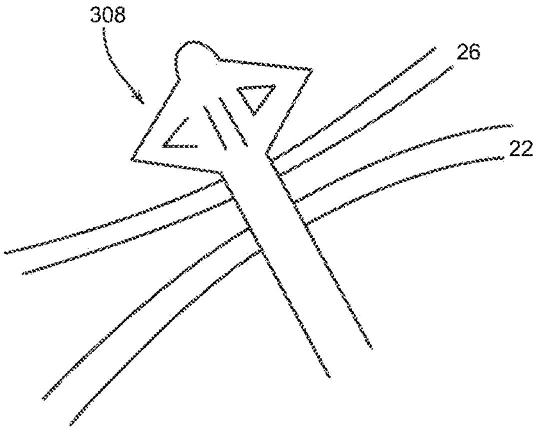

FIG. 17 illustrates a malecot catheter 308 acting as an anchoring device to bring the tissues 22, 26 together.

FIGS. 18A-18F illustrate a method of accessing the gallbladder, via endoscopic ultrasound guided access 14 and utilizing an access device emitting monopolar energy 27, anchoring a delivery device 14 via the use of a balloon catheter 307, and subsequently delivering a pair of magnetic anastomosis devices 16*a*, 16*b* within the balloon 307 while the balloon 307 is anchored within the formed enterotomy between the gallbladder tissue 26 and adjacent tissue 22 (i.e., stomach or duodenum tissue), thereby deploying the devices 16*a*, 16*b* on either side of the respective tissues 22, 26 (i.e., first device within the gallbladder 11 and second device within stomach 10 or duodenum 76) for the formation of an anastomosis there between.

Figure 18A:
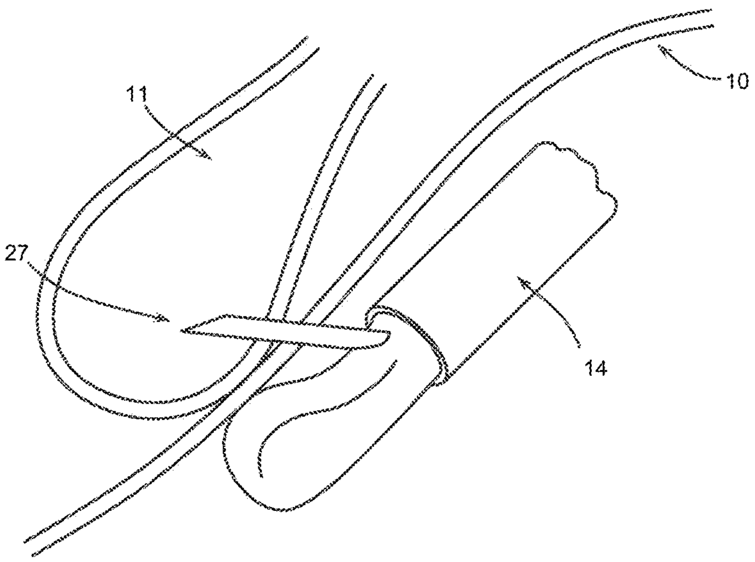
FIGS. 18A, 18B, 18C, 18D, 18E, and 18F illustrate a technique of accessing the gallbladder and delivering a pair of magnetic anastomosis devices for the formation of an anastomosis between the gallbladder tissue and adjacent tissue.

FIG. 18A illustrates an EUS scope 14 accessing the stomach 10/duodenum 76 and a monopolar energy tip 27 piercing the stomach/duodenum tissue 22 into the gallbladder tissue 26 in order to deliver an anastomosis device 16 therein.

Figure 18B:
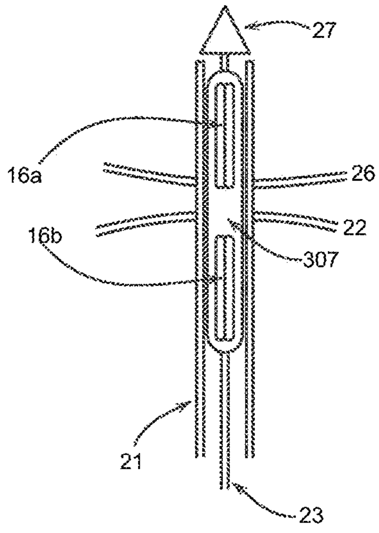

FIG. 18B illustrates a cutaway view of the delivery device 15. The monopolar energy tip 27 pierces the stomach/duodenum tissue 22 into the gallbladder tissue 26. The device 15 is positioned within the enterotomy between the tissues. Within the delivery device 15, the magnetic anastomosis devices 16*a*, 16*b* are collapsed within a balloon catheter 307 within a sheath 21 in the delivery device. A conductor 23 is utilized to later remove the sheath 21 and stabilize the balloon catheter 307 in place.

Figure 18C:
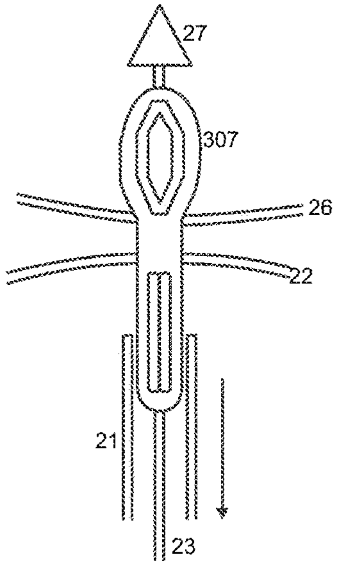

FIG. 18C illustrates the sheath 21 being removed from the balloon catheter 307 to position and inflate the catheter 307 within the enterotomy.

Figure 18D:
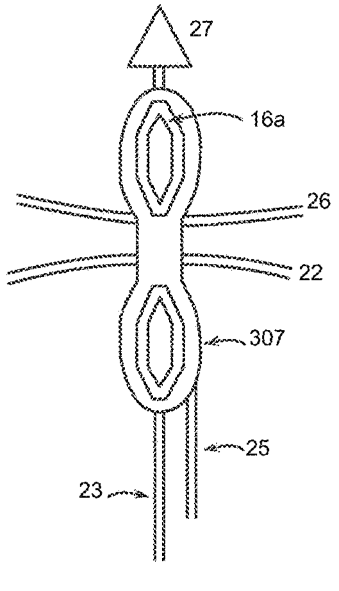

FIG. 18D illustrates the sheath 21 being fully removed and the balloon catheter 307 being inflated by an inflation line 25. The once compressed anastomosis device 16*a* expands within the lumen.

Figure 18E:
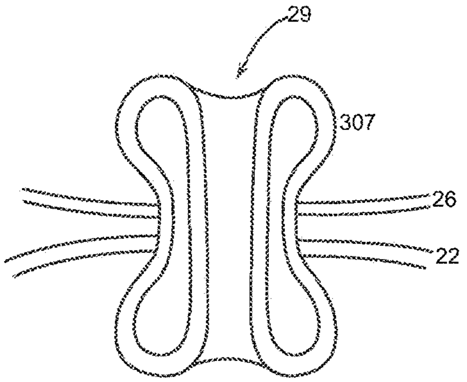

FIG. 18E illustrates a cross-section of the fully inflated balloon catheter. The "donut" shaped balloon has a thin inner hole or inner channel 29 for fluid and other material to flow through as an anastomosis.

Figure 18F:
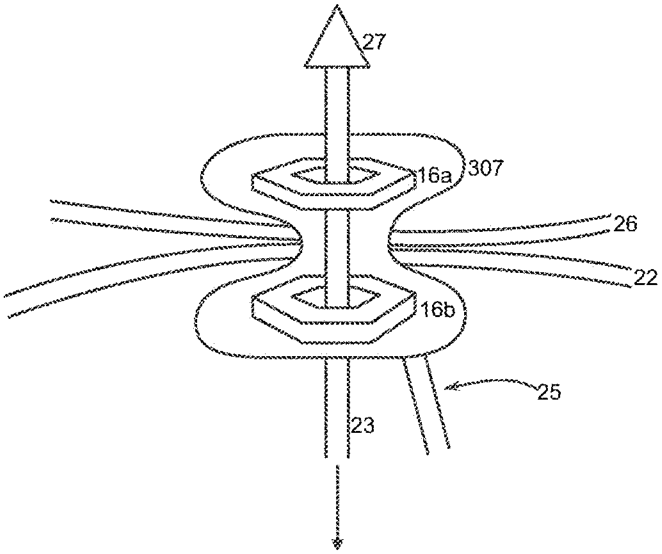

FIG. 18F illustrates the fully deployed balloon catheter 307 being inflated by the inflation line 25. When the balloon catheter 307 is fully inflated, the monopolar energy tip 27 is removed, leaving the catheter 307 and anastomosis devices 16.

Figure 19:
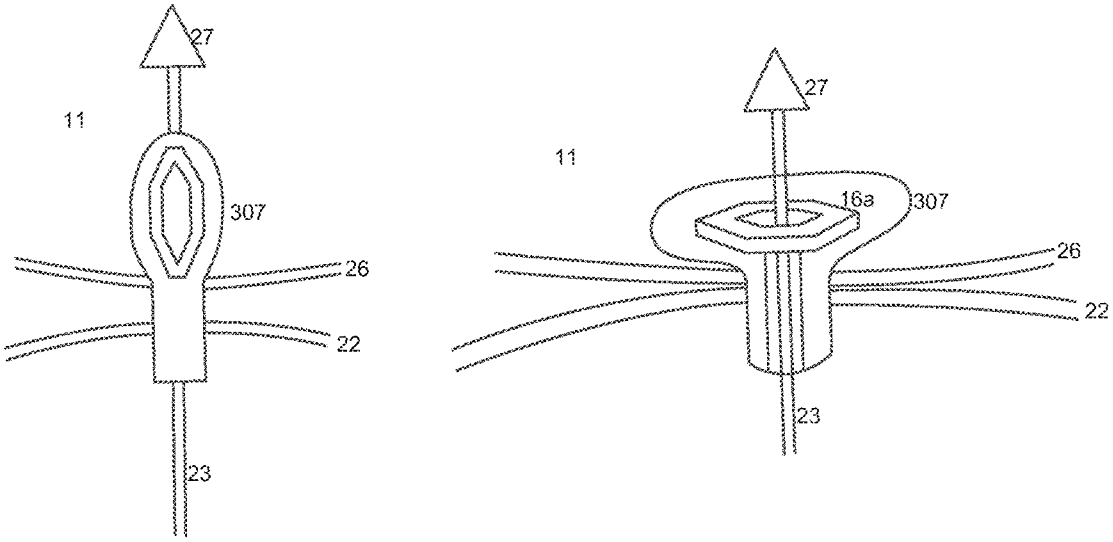
FIG. 19 illustrates a variation of the design of FIGS. 18A-18F, specifically utilizing a balloon to deliver a single magnetic anastomosis device within the gallbladder, rather than delivering the pair.

FIG. 19 illustrates a variation of design of FIGS. 18A-18F, specifically utilizing a balloon 307 to deliver a single magnetic anastomosis device 16*a* within the gallbladder 11, rather than delivering the pair.

Figure 20A:
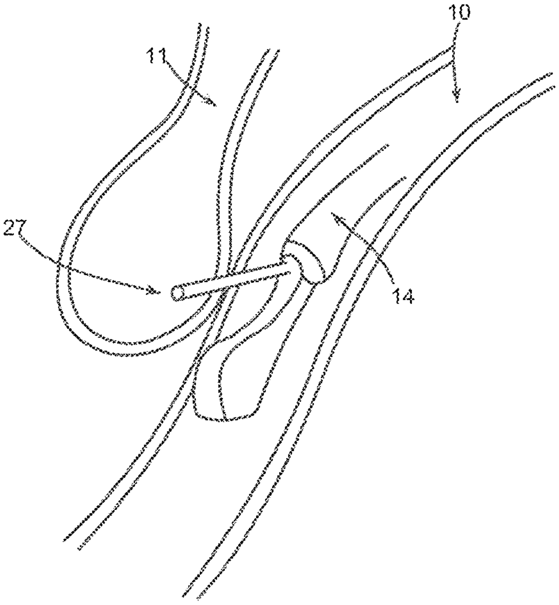
FIGS. 20A, 20B, and 20C illustrate a method of accessing the gallbladder, via endoscopic ultrasound guided access and utilizing a hot insertion tube emitting monopolar energy, and subsequently delivering a magnetic anastomosis device within the gallbladder via the hot tube.
Figure 20B:
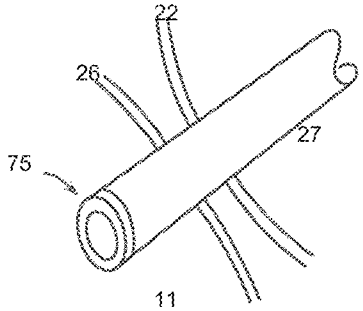
Figure 20C:
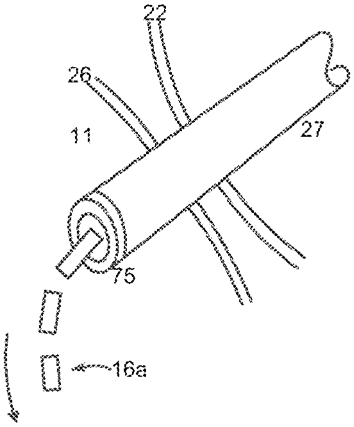

FIGS. 20A-20C illustrate a method of accessing the gallbladder 11, via endoscopic ultrasound guided access 14 and utilizing a hot insertion tube emitting monopolar energy 27, and subsequently delivering a magnetic anastomosis device 16 within the gallbladder 11 via the hot tube 27.

FIG. 20A illustrates an EUS scope 14 accessing the stomach 10/duodenum 76 and utilizing a hot insertion tube 27 to access the gallbladder 11 in order to deliver an anastomosis device 16 therein.

FIG. 20B illustrates the activation of a monopolar energy tip 75 to advance the insertion tube 27 into the gallbladder 11.

FIG. 20C illustrates the distal tip of the delivery device deploying the magnetic anastomosis device 16*a*.

Figure 21A:
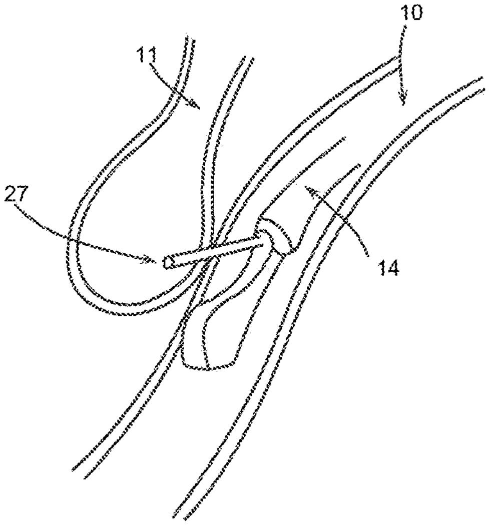
FIGS. 21A, 21B, 21C, 21D, and 21E illustrate a technique of accessing the gallbladder and delivering a pair of magnetic anastomosis devices for the formation of an anastomosis between the gallbladder tissue and adjacent tissue (i.e., stomach or duodenum tissue).

FIG. 21A illustrates an EUS scope 14 accessing the stomach 10/duodenum 76 and utilizing a hot insertion tube 27 to access the gallbladder 11 in order to deliver an anastomosis device 16*a* therein.

Figure 21B:
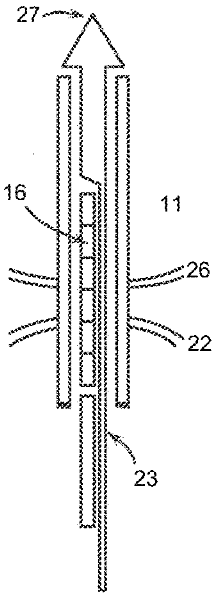
Figure 21C:
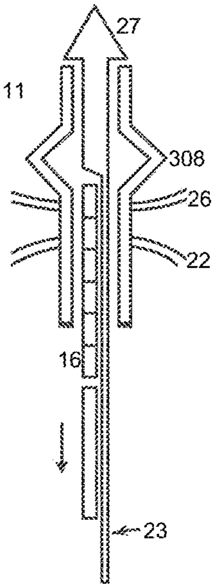
Figure 21D:
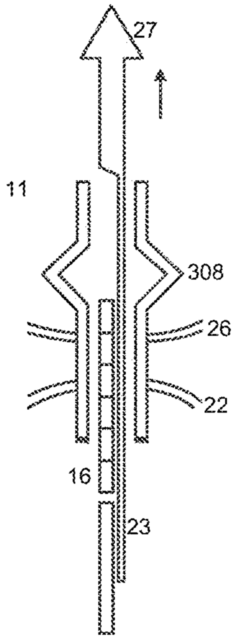

FIG. 21B illustrates a method of accessing the gallbladder, via endoscopic ultrasound guided access 14 and utilizing an access device 14 having a conductor 23 including a "hot" tip emitting monopolar energy 27, anchoring the delivery device via the use of a malecot catheter 308, and subsequently utilizing the malecot catheter 308 as a conduit for delivering a magnetic anastomosis device 16 therethrough and into the gallbladder 11 while the malecot catheter 308 is anchored within the formed enterotomy between the gallbladder tissue 26 and adjacent tissue 22 (i.e., stomach or duodenum tissue). The user pulls back on the access device 14 in order to open the magnets 16 (FIG. 21C) and advance the tip 27 (FIG. 21D).

Figure 21E:
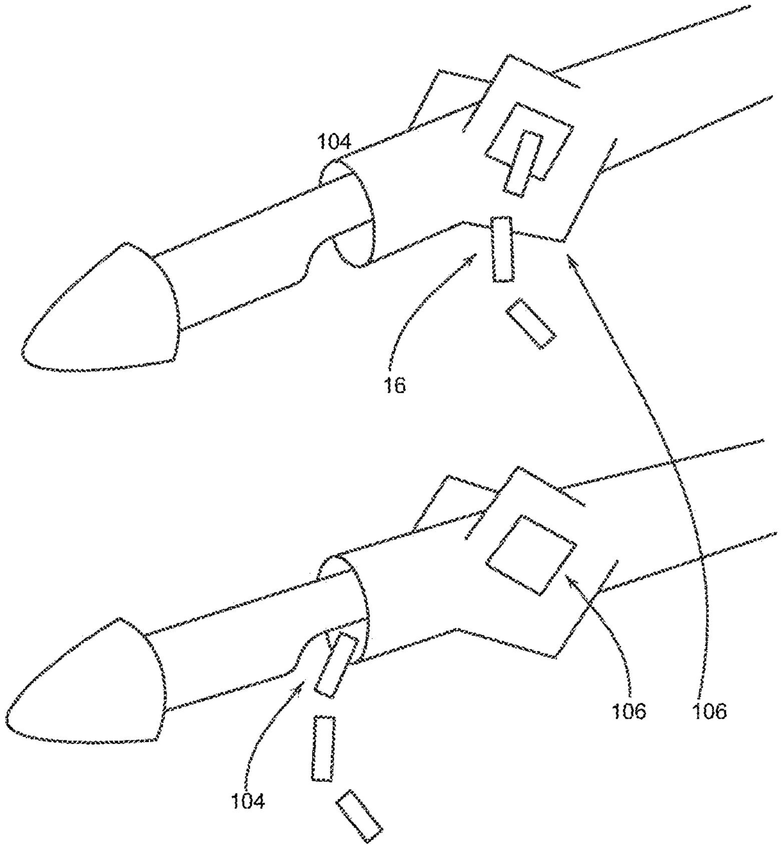

FIG. 21E illustrates that the magnetic anastomosis devices 16 could be deployed through the end of the access device 104, or through a window in the catheter 106. In some embodiments, the window in the catheter 106 can be radio opaque in order to keep oriented properly.

Figure 22C:
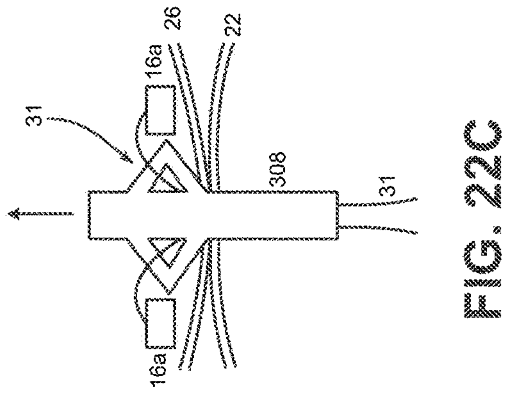
FIGS. 22A, 22B, and 22C illustrate a variation of the procedure and devices illustrated in FIGS. 21A-21E in that the magnetic anastomosis device is preloaded into a distal end of the malecot catheter of the delivery device resulting in delivery and deployment of the device upon transitioning of the malecot end into an anchored position.
Figure 22B:
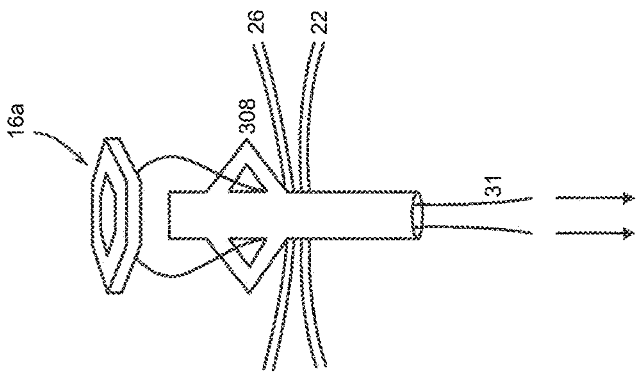
Figure 22A:
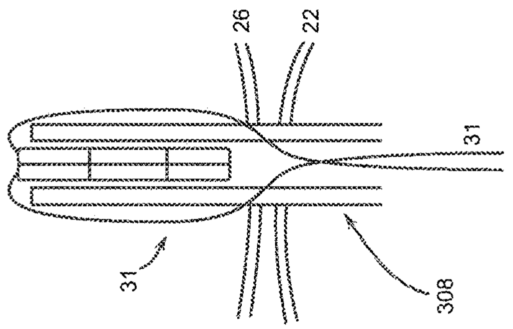

FIGS. 22A-22C illustrate a variation of the procedure and devices illustrated in FIGS. 21A-21E. FIG. 22A illustrates the magnetic anastomosis device 16*a* preloaded into a distal end of the malecot catheter 308 of the delivery device 14 with sutures 31 securing the magnet 16*a* within the delivery device 308.

FIG. 22B illustrates how a user pulls back on the sutures 31 resulting in delivery and deployment of the device 16*a* upon transitioning of the malecot end 308 into an anchored position.

FIG. 22C illustrates how pushing the delivery device 308 forwards cuts the sutures 31 in the malecot catheter's 308 windows.

Figure 23:
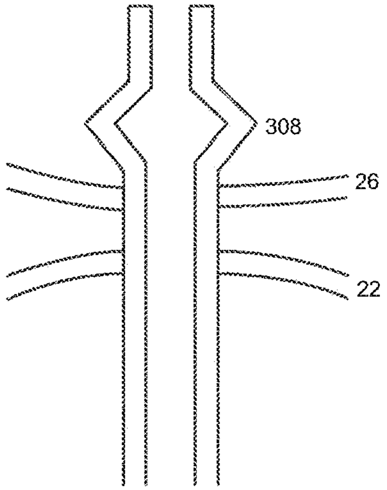
FIG. 23 illustrates a malecot catheter having a distal end that expands into the anchored position on one side of the gallbladder tissue wall.

FIG. 23 illustrates a malecot catheter 308 having a distal end that expands into the anchored position on one side of the gallbladder tissue wall 26.

Figure 24:
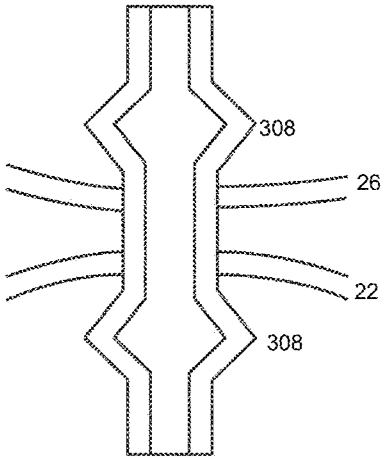
FIG. 24 illustrates a malecot catheter having a distal end that expands into the anchored position on both sides of the gallbladder tissue wall.

FIG. 24 illustrates a malecot catheter 308 having a distal end that expands into the anchored position on both sides of the gallbladder tissue wall 26. In both instances, a temporary malecot, 308 may be placed inside of the gallbladder 11 to create a temporary conduit, which allows for drainage to occur immediately and could further allow for insufflation of the gallbladder as well. It should be noted that, any of the embodiments that provide access from the GI tract into the gallbladder (malecot, hot tube, nitinol coil, balloon, etc.), specifically any of the devices that creates a channel through which the magnetic anastomosis device will pass, can also serve as a drainage channel. More specifically, after the access channel has been created, any fluid of material within the gallbladder could be evacuated (either on its own or if suction is applied) before delivery of the magnetic anastomosis device begins. The channel could also be used to push fluid into the gallbladder prior to draining out the gallbladder (potentially doing the fill/drain cycle a number of times) in order to 'clean' out the gallbladder in the event that the gallbladder has excess fluid and contents within (i.e., bile or other contents).

Figure 25A:
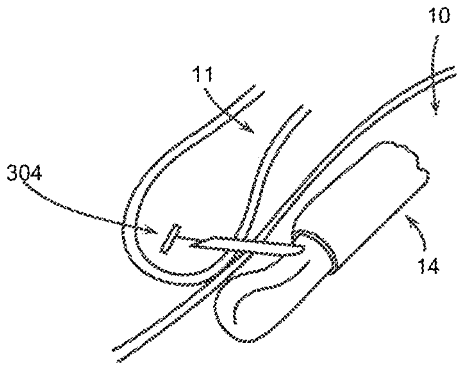
FIGS. 25A, 25B, 25C, 25D, 25E illustrate a technique of accessing the gallbladder and delivering a pair of magnetic anastomosis devices for the formation of an anastomosis between the gallbladder tissue and adjacent tissue (i.e., stomach or duodenum tissue).
Figure 25B:
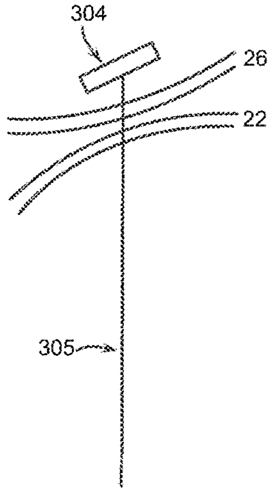

FIGS. 25A-25E illustrate a method of accessing the gallbladder 11, via endoscopic ultrasound guided access needle 14, and anchoring the delivery device 100 via the use of a T-bar assembly 304. As shown in FIG. 25B, the T-bar 304 is anchored within the formed enterotomy between the gallbladder tissue 26 and adjacent tissue 22 (i.e., stomach or duodenum tissue) and is tethered 305 to the gallbladder wall 26.

Figure 25C:
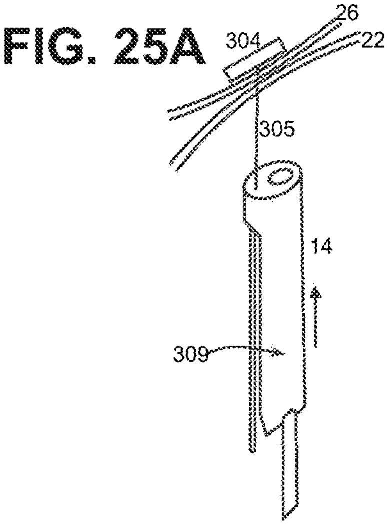

FIG. 25C illustrates the stabilizer member 309. The stabilizer member 309 is advanced to the wall of the duodenum 76 or stomach 10 for traction. The deployment sheath 21 is then advanced into the gallbladder 11 as shown in FIG. 25D, at which point the magnetic anastomosis device 16*a* can be delivered. In some embodiments, the system can rotate in order to help deploy the magnetic anastomosis devices 16.

Figure 25E:
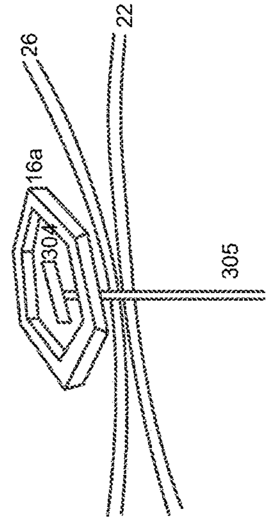
Figure 25D:
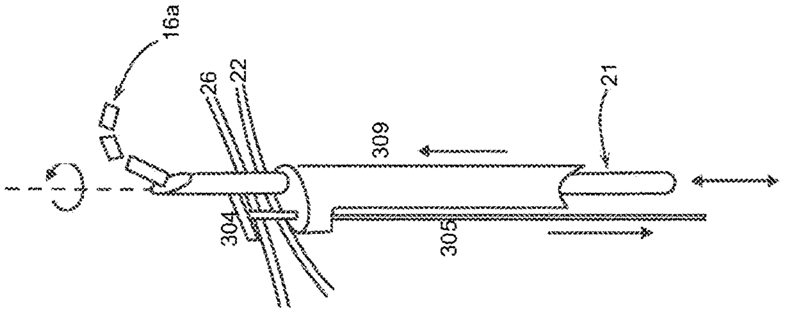

FIG. 25E illustrates the fully formed magnet anastomosis device 16*a* surrounding the T-bar 304. In some embodiments, the T-bar 304 is metallic and can be attracted to and stick to the magnet 16*a*.

Figure 26C:
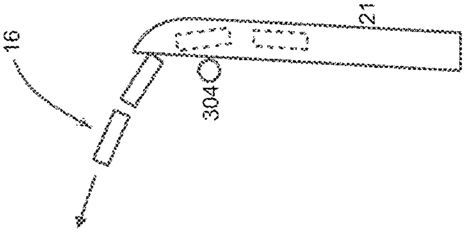
FIGS. 26A, 26B, 26C illustrate a variation of the procedure and devices illustrated in FIGS. 25A-25E in that the deployment sheath includes a notch on a distal end thereof configured to engage the T-bar upon advancement through the enterotomy, thereby pushing the T-bar to the side to allow for subsequent delivery and deployment of the magnetic anastomosis device.
Figure 26B:
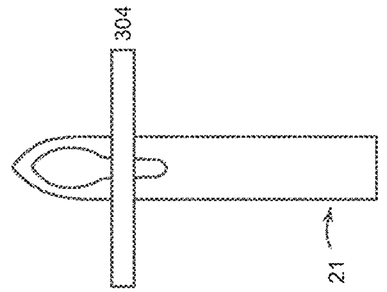
Figure 26A:
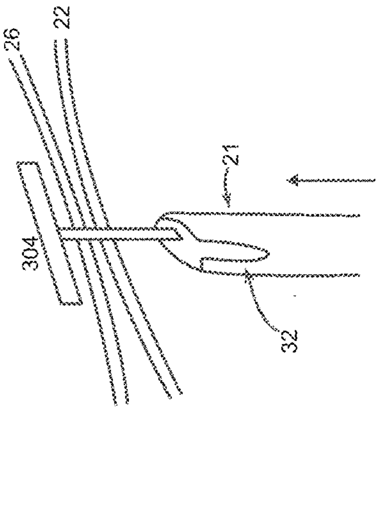

FIGS. 26A-26C illustrate a variation of the procedure and devices illustrated in FIGS. FIG. 26A illustrates that the deployment sheath 21 includes a notch 32 on a distal end thereof configured to engage the T-bar 304 upon advancement through the enterotomy. FIG. 26B illustrates the notch 32 in the deployment sheath 21 pushing the T-bar 304 to the side to allow for subsequent delivery and deployment of the magnetic anastomosis device 16. FIG. 26C illustrates the magnetic anastomosis device 16 being deployed with the T-bar 304 pushed to the side.

Figure 27A:
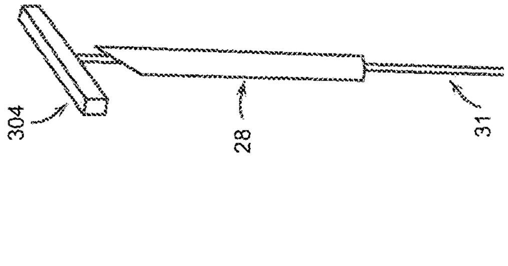
FIGS. 27A, 27B, and 27C illustrate another variation of the procedure and devices illustrated in FIGS. 25A-25E in that, rather than including a deployment sheath for delivering a self-assembling magnetic anastomosis device, as previously described herein, the assembly of FIGS. 27A-27C relies on the depositing of T-bars through an access needle, such that a grouping of T-bars are configured to self-assemble into an array and serve as the distal anastomosis device to correspondingly mate with a proximal magnetic anastomosis device positioned on the other side to subsequently compress tissue there between to form an anastomosis.
Figure 27B:
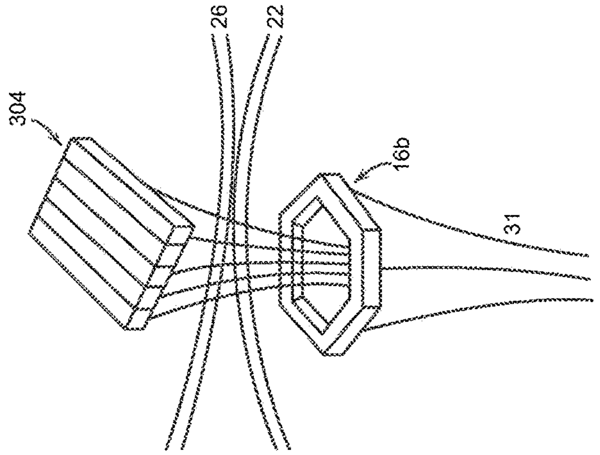
Figure 27C:
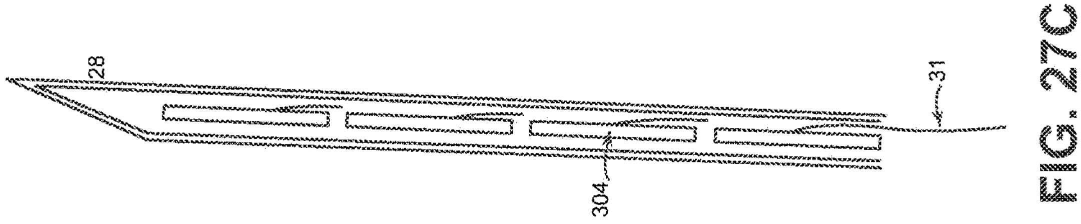

FIGS. 27A-27C illustrate another variation of the procedure and devices illustrated in FIGS. 25A-25E in that, rather than including a deployment sheath for delivering a self-assembling magnetic anastomosis device 16, as previously described herein, the assembly of FIGS. 27A-27C relies on the depositing of T-bars 304 through an access needle 28, such that a grouping of T-bars 304 are configured to self-assemble into an array and serve as the distal anastomosis device to correspondingly mate with a proximal magnetic anastomosis device 16*b* positioned on the other side to subsequently compress tissue 22, 26 there between to form an anastomosis.

FIG. 27A illustrates a T-bar 304 assembly being delivered through an access needle 28. In some embodiments, the T-bars 304 are magnetic. By pulling back on the delivery device 14, a user is able to deploy the T-bar 304 into the lumen. The T-bar 304 is secured in place by sutures 31.

FID. 27B illustrates a fully deployed array of T-bar 304 magnets. In this embodiment, the T-bars 304 are magnetic and able to attract to the proximal anastomosis device 16*b*. By pulling on the sutures 31, the user is able to bring the T-bar 304 array to the proximal anastomosis device 16*b* in order to create an anastomosis therein.

FIG. 27C illustrates the T-bar 304 array and sutures 31 loaded linearly into the access needle 28. Loading the T-bars 304 linearly allows for a minimally invasive creation of an anastomosis. Because the magnetic assemblies are loaded linearly and then self-assemble, the aspect ratio of the resulting anastomosis can be greater than 1:1 as the magnetic assemblies assemble to a size greater than the diameter of the access needle. This allows for the creation of larger anastomoses while still maintaining a minimally invasive procedure.

Figure 28A:
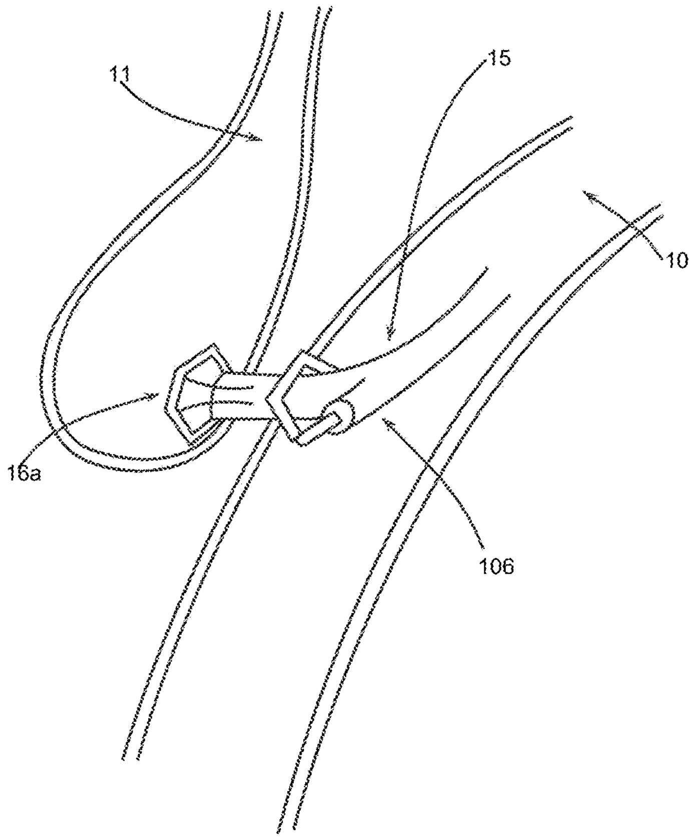
FIGS. 28A, 28B, and 28C illustrate a method of accessing the gallbladder, via endoscopic ultrasound guided access needle access, utilizing a side port deployment sheath for delivery and deployment of a pair of magnetic anastomosis devices.
Figure 28B:
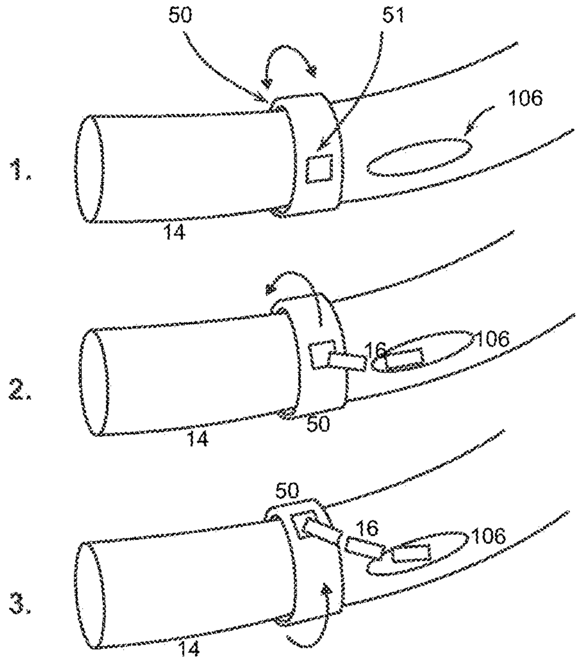
Figure 28C:
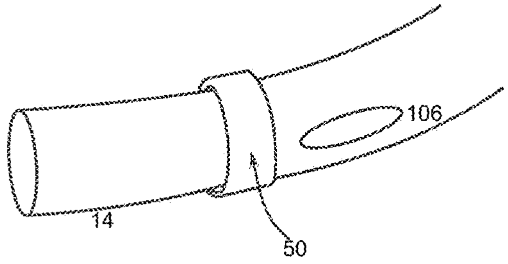

FIGS. 28A-28C illustrate a method of accessing the gallbladder 11, via endoscopic ultrasound guided access needle access 14, utilizing a side port deployment sheath 106 for delivery and deployment of a pair of magnetic anastomosis devices 16.

FIG. 28A illustrates a method of accessing the gallbladder 11 in order to deploy a distal magnetic anastomosis device 16*a*. The delivery device 15 accesses the stomach 10/duodenum 76 and pierces through the stomach tissue wall 22 into the gallbladder 11. The delivery device 15 in this embodiment has a side port 106 for deployment of the proximal magnetic anastomosis device 16*b*.

FIG. 28B illustrates a rotating ring 50 with a metal insert 51 consistent with some embodiments of the invention. The rotating ring 50 is capable of rotating around the shaft of the delivery device. As the magnetic devices 16 are deployed from the side port 106 of the delivery device 14, the metal insert 51 on the rotating ring 50 catches the magnetic devices 16 and guides the magnets 16 out of the delivery device 14 and around the shaft of the delivery device 14 in order to aid self-assembly of the magnetic anastomosis devices 16. The rotating ring 50 in some embodiments may be free spinning, or may rotate when the magnet 16 is pushed out of the delivery device 14. In some embodiments the rotating ring 50 may be actively rotated to pull the magnetic device 16 out of the delivery device 14.

FIG. 28C is a close-up view of the rotating ring 50 on the shaft of the delivery device 15. The rotating ring 50 may be made of metal in some embodiments.

Figure 29A:
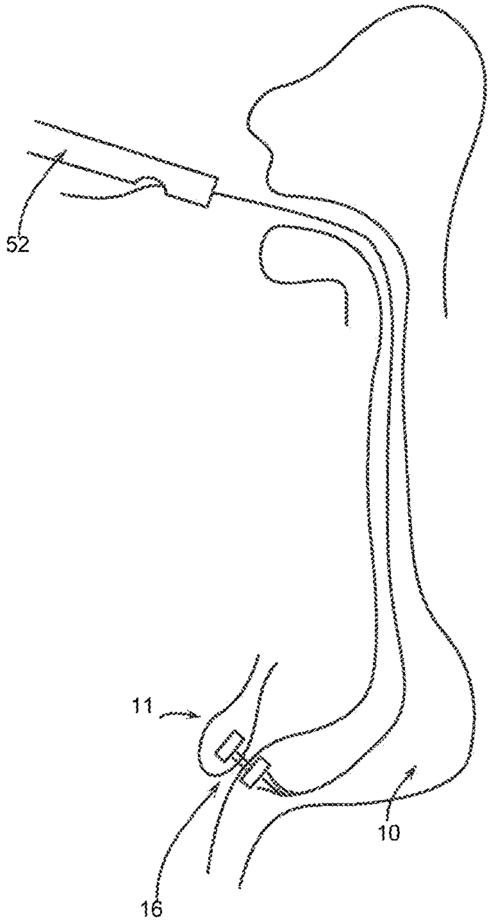
FIGS. 29A, 29B, and 29C illustrate a knotting member configured to secure already deployed and positioned magnetic anastomosis devices to the target site tissues and subsequently cut guide elements or sutures coupled thereto.
Figure 29B:
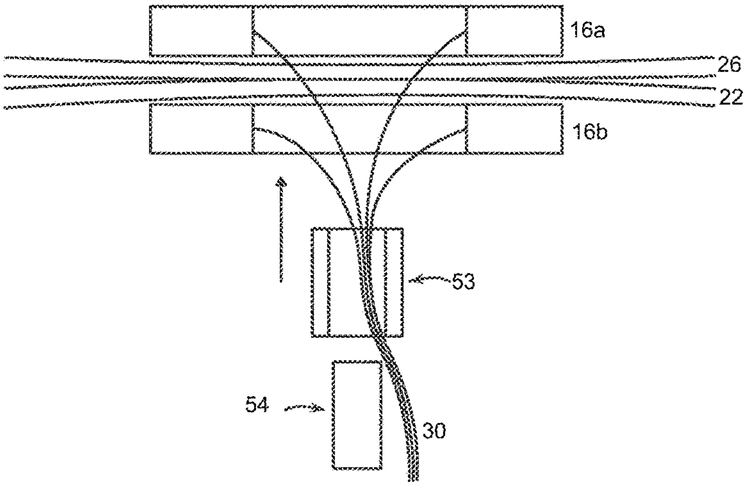
Figure 29C:
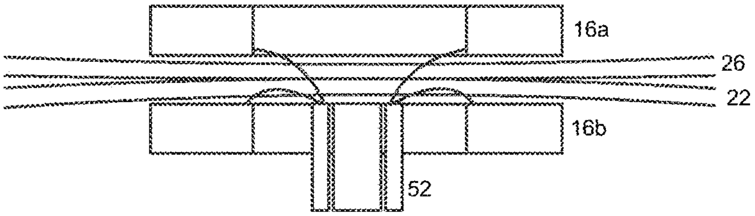

FIGS. 29A-29C illustrate a knotting member 52 configured to secure already deployed and positioned magnetic anastomosis devices 16 to the target site tissues and subsequently cut guide elements 30 or sutures 31 coupled thereto. As shown in FIG. 29A, the knotting member 52 is advanced over guide elements 30 within a working channel of a scope. The guide elements are positioned through the patient to the stomach 10 and connected to previously positioned anastomosis devices 16 in the gallbladder 11 and stomach 10.

FIG. 29B illustrates the knotting member 52 advancing towards the magnetic anastomosis devices 16, wherein the knotting member 52 generally consists of an outer tube member 53 and an inner rod member 54, such that, upon reaching the devices, the inner rod 54 member can be pressed towards a distal end of the outer tube member 53, thereby securing a portion of the guide elements 30 there between and further cutting the guide elements 30 in the process.

FIG. 29C illustrates the knotting member 52 being fully advanced to the magnetic anastomosis devices 16*a*, 16*b*, thereby securing the guide elements 30 and further cutting the guide elements 30.

FIGS. 30A-30D illustrate a method of accessing the gallbladder 11, via endoscopic ultrasound guided access needle 14 access, and delivering a magnetic coil 53 or ring configured to transition from a substantially linear shape to a substantially annular shape upon delivery into the gallbladder 11 and is configured to serve the distal anastomosis device to correspondingly mate with a proximal magnetic anastomosis device 16*b* positioned on the other side to subsequently compress tissue 22, 26 there between to form an anastomosis.

Figure 30A:
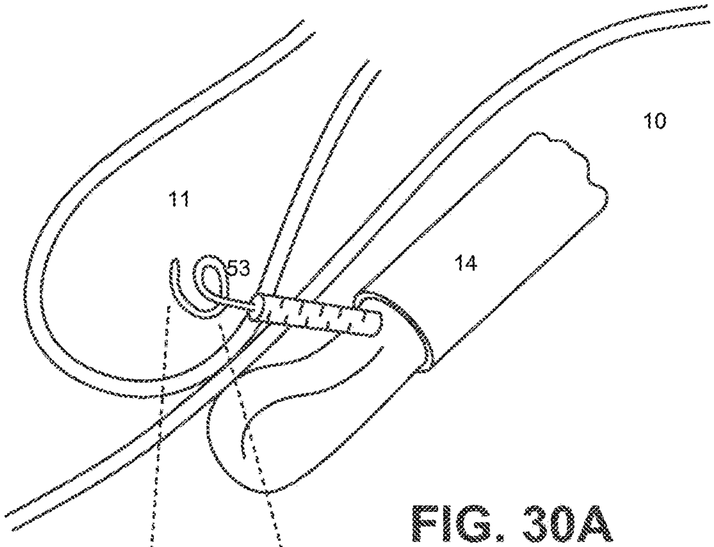
FIGS. 30A, 30B, 30C, and 30D illustrate a technique of accessing the gallbladder and delivering a pair of magnetic anastomosis devices for the formation of an anastomosis between the gallbladder tissue and adjacent tissue.

FIG. 30A illustrates a delivery device 14 accessing the stomach 10 and deploying through the stomach tissue wall 22 into the gallbladder 11 a magnetic coil 53 or ring to serve as the distal anastomosis device.

Figure 30B:
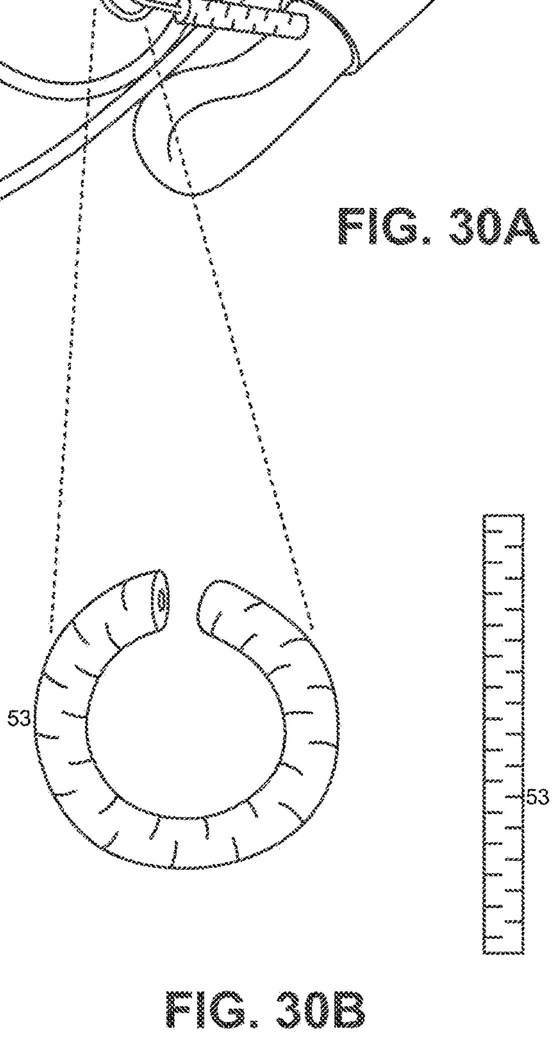

FIG. 30B illustrates a close-up view of the magnetic coil 53 or ring in the annular and straight positions. The magnetic device 53 is loaded into the delivery device 14 in the straight position. Once deployed, the magnetic device 53 self-assembles into a coil or ring shape in order to serve as the distal magnetic anastomosis device. In some embodiments, the coil is a laser cut hypotube, allowing the magnetic device 53 to flex.

Figure 30C:
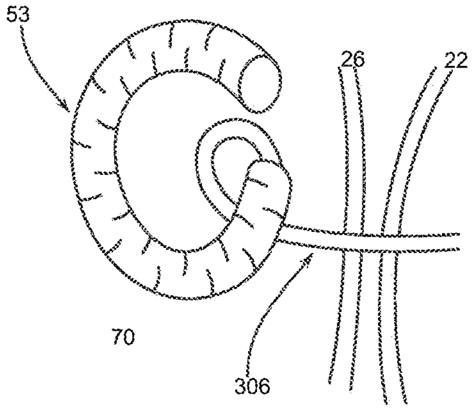

FIG. 30C illustrates a hypotube magnetic device 53 being deployed into the distal lumen by a nitinol or pig tail wire 306. The nitinol wire 306 pierces through the stomach tissue wall 22 into the gallbladder 11 to deliver the distal anastomosis device, in this embodiment a magnetic hypotube 53.

Figure 30D:
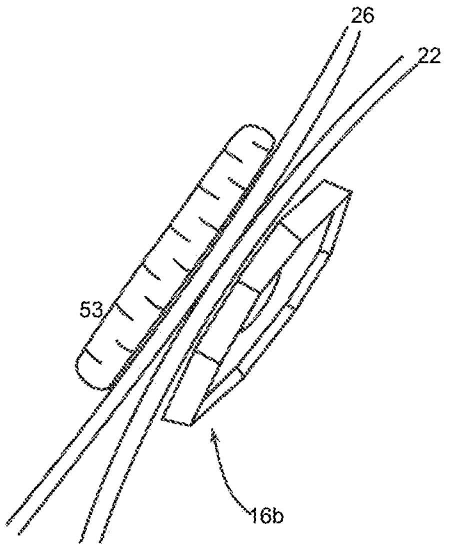

FIG. 30D illustrates the proximal magnet 16*b* mating with the magnetic hypotube anastomosis device 53. Once deployed, the hypotube 53 self-assembles into an annular shape. Due to corresponding polarities in the proximal 16*b* and distal 53 magnets, the magnets mate and compress the tissue 22, 26 therebetween, thus forming an anastomosis.

Figure 31A:
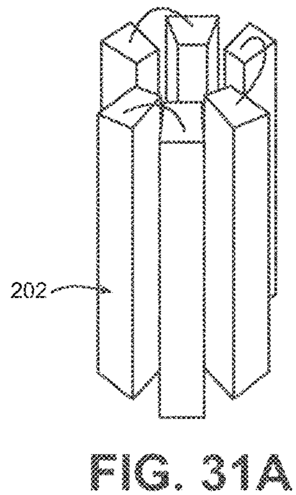
FIGS. 31A and 31B illustrate a set of magnetic segments prepackaged in an unstable polarity including a plurality of guide elements, tethers, or sutures coupling adjacent segments to one another to assist in self-assembly of the magnetic segments into a polygon deployed shape.

FIG. 31A illustrates a set of magnetic segments 202 prepackaged in an unstable polarity including a plurality of guide elements 30, tethers, or sutures coupling adjacent segments to one another to assist in self-assembly of the magnetic segments 202 into a polygon deployed shape.

Figure 31B:
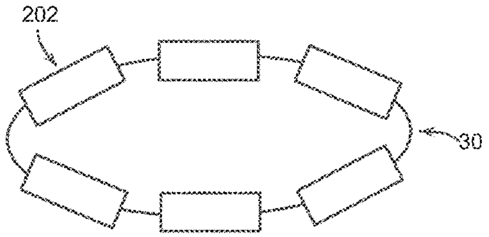

FIG. 31B illustrates a self-assembled magnetic anastomosis device. Upon deployment from the delivery device 14, the magnetic anastomosis device 16 self-assembles into a polygon shape. The magnetic segments 200 are held in a polygon deployed shape by the guide elements 30, tethers, or sutures.

Figure 32A:
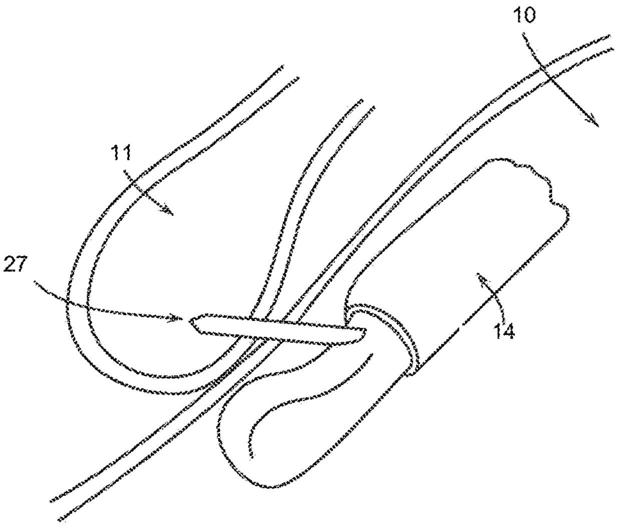
FIGS. 32A and 32B illustrate a method of accessing the gallbladder, via endoscopic ultrasound guided access and utilizing an access device having a conductor including a "hot" tip emitting monopolar energy, and subsequently delivering the prepackaged magnetic segments of FIGS. 31A and 31B into the gallbladder by way of a sheath.
Figure 32B:
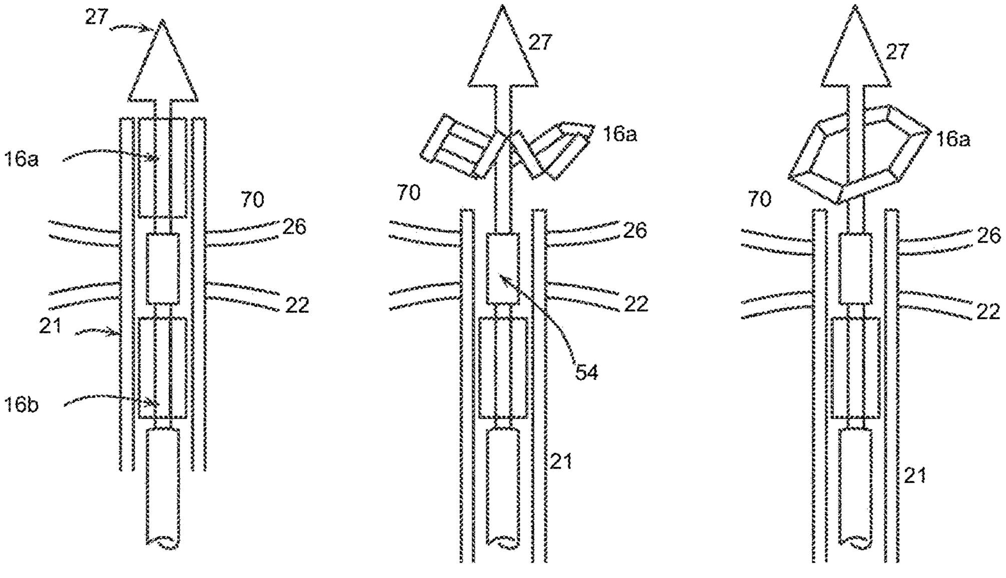

FIGS. 32A and 32B illustrate a method of accessing the gallbladder 11, via endoscopic ultrasound guided access 14 through the stomach 10/duodenum 76 and utilizing an access device having a conductor including a "hot" tip emitting monopolar energy 27, and subsequently delivering the prepackaged magnetic segments of FIGS. 31A-31B into the gallbladder 11 by way of a sheath 21.

FIG. 32A illustrates an EUS scope 14 guided into the stomach 10. The scope deploys a "hot" tip 27 that utilizes monopolar energy to pierce through the tissue 22 of the stomach 10 and into the gallbladder 11 and therein deliver a magnetic anastomosis device 16*a*.

FIG. 32B illustrates a close-up of the "hot" tip deployment mechanism. The "hot" tip utilizing monopolar energy 27 pierces the stomach tissue 22 into the gallbladder 11. The distal magnet 16*a*, a spacer 54 between the magnets, and a proximal magnet 16*b* are loaded into the sheath 21. By the user pulling back on the delivery device 14, the distal magnet 16*a* is deployed and self-assembles inside the distal lumen 70.

Figure 33A:
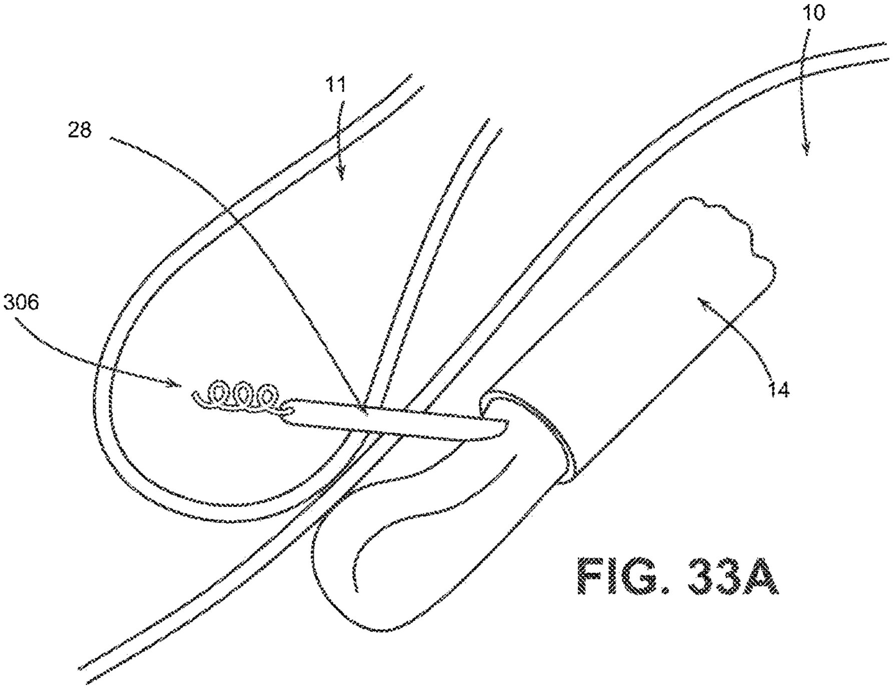
FIGS. 33A, 33B, and 33C illustrate a method of accessing the gallbladder, via endoscopic ultrasound guided access and utilizing a needle for access into the gallbladder, and subsequent delivery of a coiled stack of magnetic segments configured to serve as a distal anastomosis device to correspondingly mate with a proximal magnetic anastomosis device positioned on the other side to subsequently compress tissue there between to form an anastomosis.
Figure 33B:
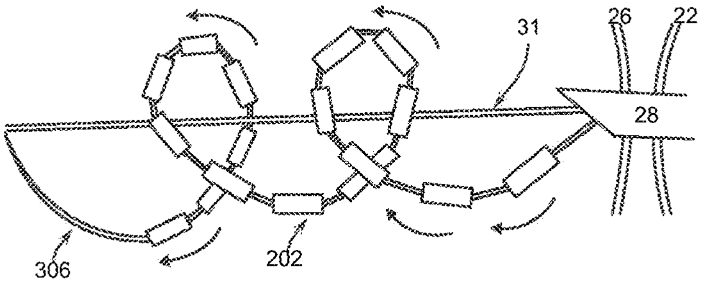
Figure 33C:
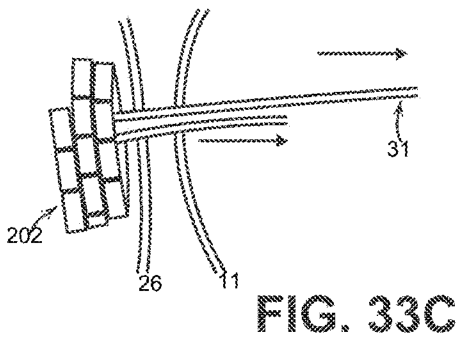

FIGS. 33A-33C illustrate a method of accessing the gallbladder 11, via endoscopic ultrasound guided access 14 and utilizing a needle 28 for access into the gallbladder 11, and subsequent delivery of a coiled stack of magnetic segments 202 configured to serve the distal anastomosis device to correspondingly mate with a proximal magnetic anastomosis device 16*b* positioned on the other side to subsequently compress tissue 22, 26 there between to form an anastomosis. As shown in FIG. 33A, the nitinol coil 306 is advanced into the gallbladder 11.

FIG. 33B illustrates how the magnetic segments 202 are then advanced around the extended nitinol coil 306.

FIG. 33C illustrates how upon pulling a suture 31, the magnetic segments 202 collapse upon one another (due to magnetic attraction forces) and form a coiled stack of magnets 202 upon removal of the nitinol coil 306.

Figure 34A:
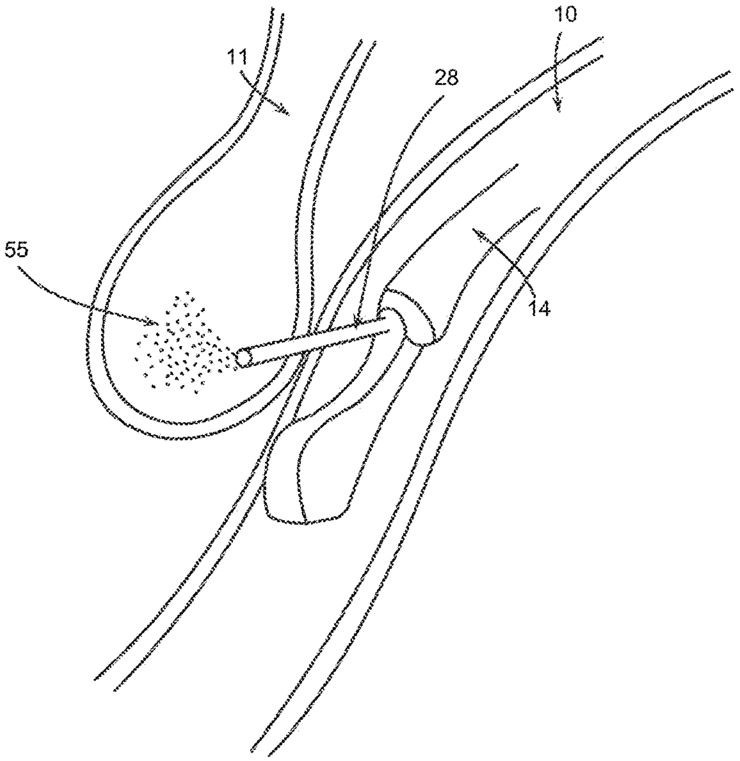
FIGS. 34A and 34B illustrate a technique of accessing the gallbladder and delivering a pair of magnetic anastomosis devices for the formation of an anastomosis between the gallbladder tissue and adjacent tissue (i.e., stomach or duodenum tissue).
Figure 34B:
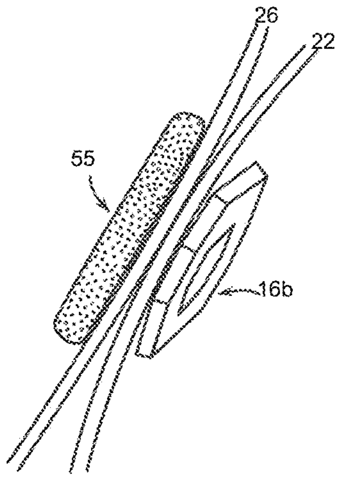

FIGS. 34A-34B illustrate a method of accessing the gallbladder 11, via endoscopic ultrasound guided access 14 and utilizing a needle for access into the gallbladder 11, and subsequent delivery of a magnetic fluid or suspension of magnetic particles 55 into the gallbladder 11 configured to serve as the distal anastomosis device to correspondingly mate with a proximal magnetic anastomosis device 16*b* positioned on the other side to subsequently compress tissue 22, 26 there between to form an anastomosis.

FIG. 34A illustrates an EUS scope 14 accessing the stomach 10. An access needle 28 having piercing capabilities pierces the stomach tissue into the gallbladder 11 to deliver magnetic fluid or particles 55 into the distal lumen.

FIG. 34B illustrates that when in proximity to the proximal magnet 16*b*, the magnetic particles 55 will attract to the proximal magnet 16*b*, compressing the tissue 22, 26 between and therein forming an anastomosis.

Figure 35:
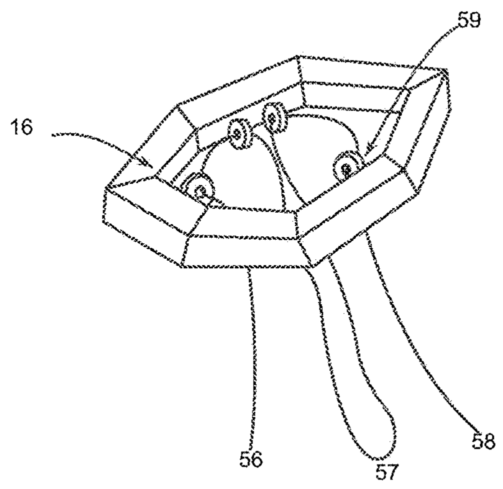
FIG. 35 illustrates a magnetic anastomosis device comprising a continuous guide element or suture that is coupled to a plurality of the magnetic segments of the device by way of eyelets positioned on each of the plurality of magnetic segments.

FIG. 35 illustrates a magnetic anastomosis device comprising a continuous guide element 30 or suture 31 that is coupled to a plurality of the magnetic segments 16 of the device by way of eyelets positioned on each of the plurality of magnetic segments. The magnets 16 have eyelets 59 on the inside circumference in order to prevent sutures from getting trapped or pinched between magnets. The sutures 31 run through the eyelets 59 and have legs 56, 57, 58 that can be pulled by the user either individually or simultaneously for manipulation of the magnet 16. Legs 56 or 58 may be pulled individually for removal of the sutures 31.

Figure 36:
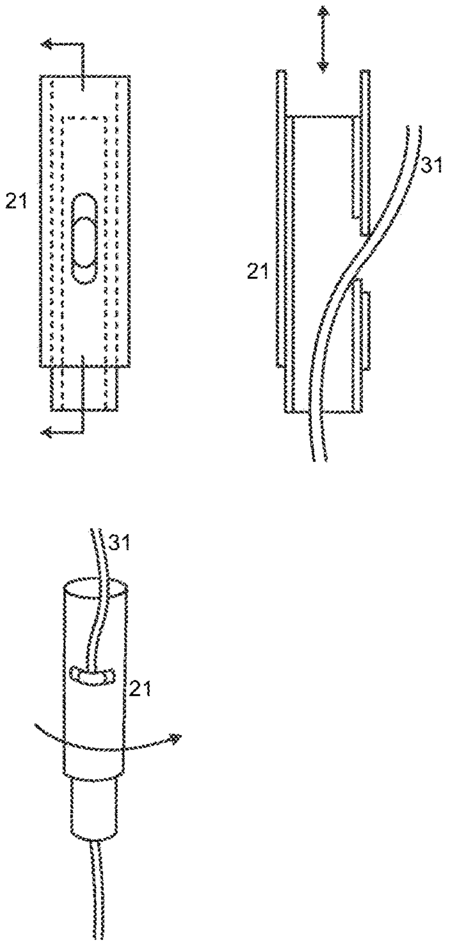
FIG. 36 illustrates one embodiment of a suture cutting arrangement within a deployment sheath of the delivery device, or a secondary device, for cutting the sutures coupled to the magnetic anastomosis devices.

FIG. 36 illustrates one embodiment of a suture cutting arrangement within a deployment sheath of the delivery device, or a secondary device, for cutting the sutures coupled to the magnetic anastomosis devices.

Figure 37A:
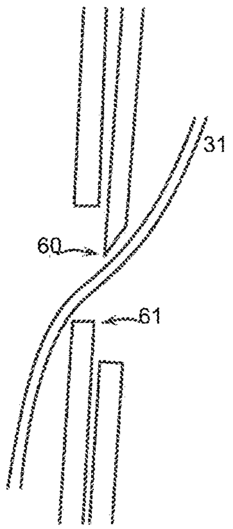
FIGS. 37A and 37B are enlarged side views illustrating an anvil/sharp (37A) arrangement and a sharp/sharp (37B) arrangement for cutting sutures.
Figure 37B:
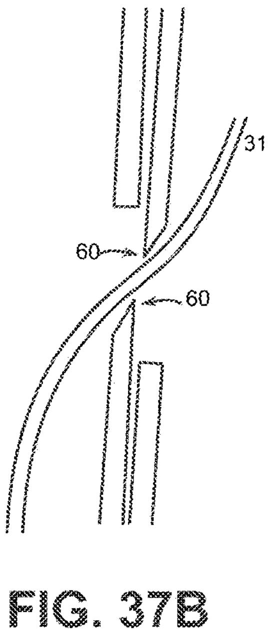

FIGS. 37A and 37B are enlarged side views illustrating an anvil/sharp arrangement and a sharp/sharp arrangement for cutting sutures.

FIG. 37A illustrates the deployment sheath utilizing a push/pull guillotine method to bring together an anvil 61/sharp 60 system to cut the sutures 31. A knife edge is exposed by pushing on the deployment sheath 21 and pulling on the sutures 31 introduces tension on the sutures 31. The tensed sutures 31 are then pulled over the sharp edges 60 and cut.

FIG. 37B illustrates a sharp 60/sharp 60 system wherein a knife edge is exposed by pushing on the deployment sheath 21 and pulling the sutures 31 introduces tension on the sutures 31. The tensed sutures 31 are then pulled over the sharp edges 60 and cut.

Figure 38:
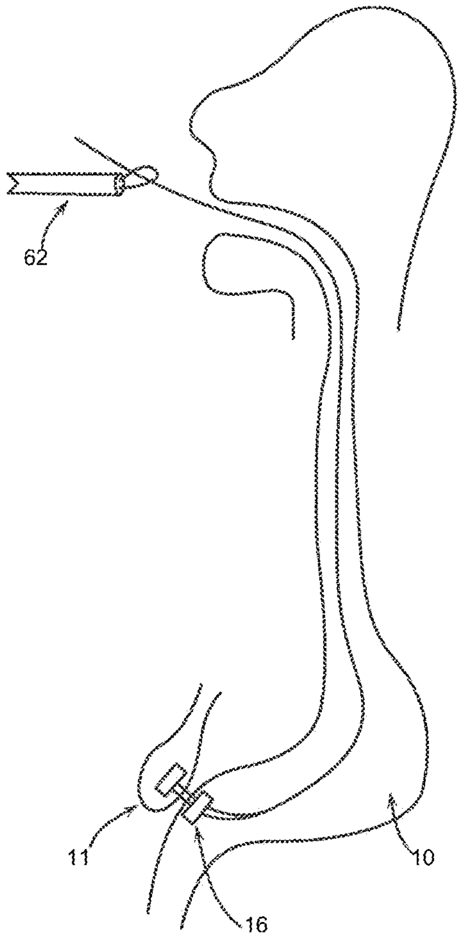
FIG. 38 illustrates a snare device (secondary device) configured to be inserted over the guide elements or sutures coupled to the magnetic anastomosis devices and configured to cut said sutures or guide elements once they have been deployed and positioned at a target site.

FIG. 38 illustrates a snare device 62 (secondary device) inserted through the working channel configured to be inserted over the guide elements 30 or sutures 31 coupled to the magnetic anastomosis devices 16 and configured to cut sutures or guide elements once they have been deployed and positioned at a target site.

Figure 39A:
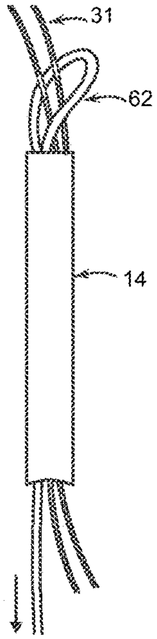
FIG. 39A illustrates a snare device comprising a resistive heating element for cutting guide elements.

FIG. 39A illustrates a snare device 62 comprising a resistive heating element for cutting guide elements. The snare device 62 is guided through the support tube of the access device 14. Once the snare 62 is in place over the sutures 31, the snare 62 is pulled back and energy is applied to cut the sutures 31. The energy applied may be low voltage from a battery or generator.

Figure 39B:
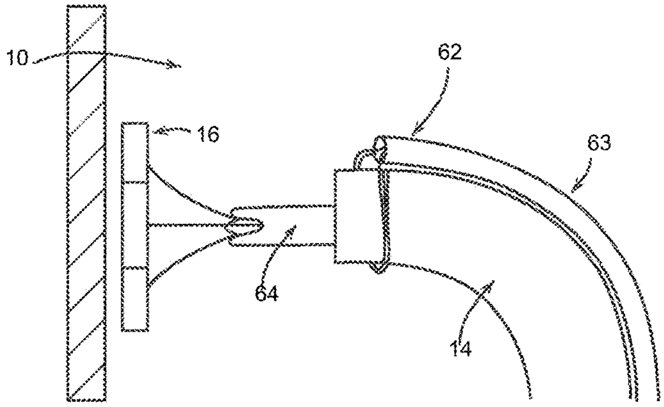
FIGS. 39B and 39C illustrate a snare device comprising a ring member having a cutting edge for cutting guide elements.

FIG. 39B illustrates the snare device 62 positioned on the outside of a scope 14 or incorporated into the cap, within a snare sleeve 63 advanced into the stomach 10. By pulling back on the scope 14, the snare device 62 is advanced onto the sutures 31 attached to a deployed magnet 16 by a deployment means 64 and cuts the sutures.

Figure 39C:
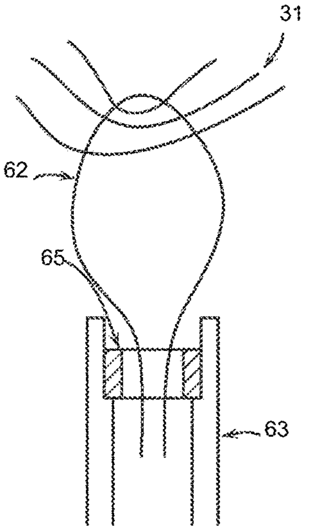

FIG. 39C illustrates a cross-section of a snare device 62 comprising a ring member having a cutting edge for cutting sutures 31. By pulling back on the snare sleeve 63, the ring 65 with the cutting edge cuts the sutures 31.

Figure 39D:
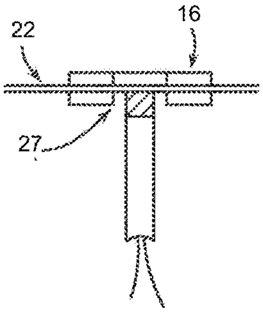
FIG. 39D illustrates a secondary device configured to provide suture or guide element cutting by way of monopolar/bipolar energy.

FIG. 39D illustrates a secondary device configured to provide suture or guide element cutting by way of monopolar/bipolar energy. A monopolar tip 27 is advanced toward the tissue 22 and cuts the sutures 31 attached to the deployed magnetic anastomosis device 16.

Figure 40:
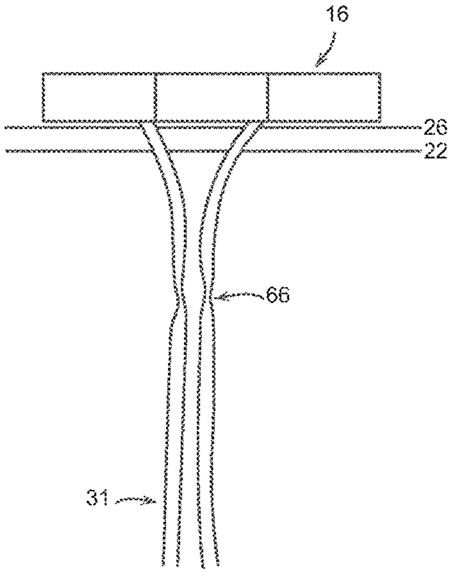
FIG. 40 illustrates breakaway guide elements or sutures.

FIG. 40 illustrates breakaway guide elements or sutures 31. In an embodiment, the sutures have a necked down or weakened area 66. By pulling back on the sutures 31, they will break away from the deployed anastomosis device 16.

Figures 41A, 41B:
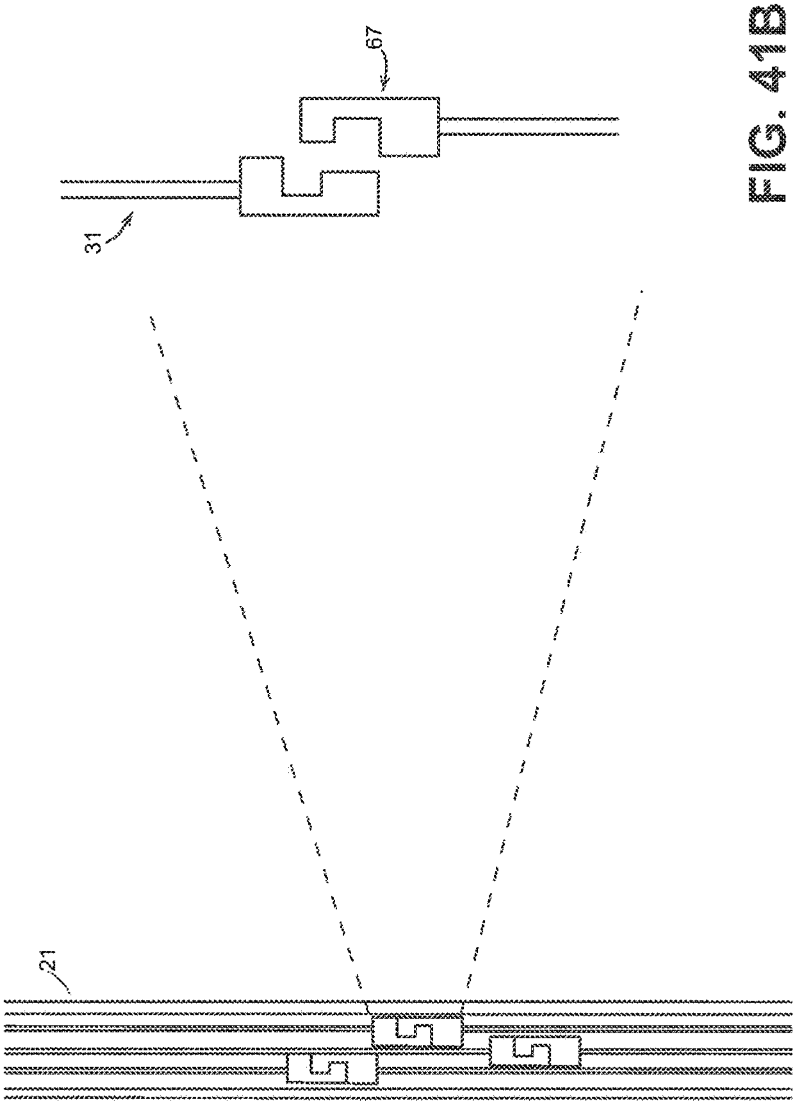
FIGS. 41A and 41B illustrate a detachable suture assembly.

FIGS. 41A and 41B illustrate a detachable suture assembly. Within the sheath 21 there are constrained overmolded drivers 67 attached to the sutures 31. The drivers 67 can be staggered to fit in the sheath 21 as shown in FIG. 41A or could be in individual lumens. By removing the sheath 21, the overmolded drivers 67 are no longer constrained and detach as seen in FIG. 41B.

Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as stomach or colon cancer. More specifically, exemplary embodiments provide various systems, devices, and methods for the delivery, deployment, and positioning of magnetic compression devices at a desired site so as to improve the accuracy of anastomoses creation between tissues, organs, or the like.

Figure 42:
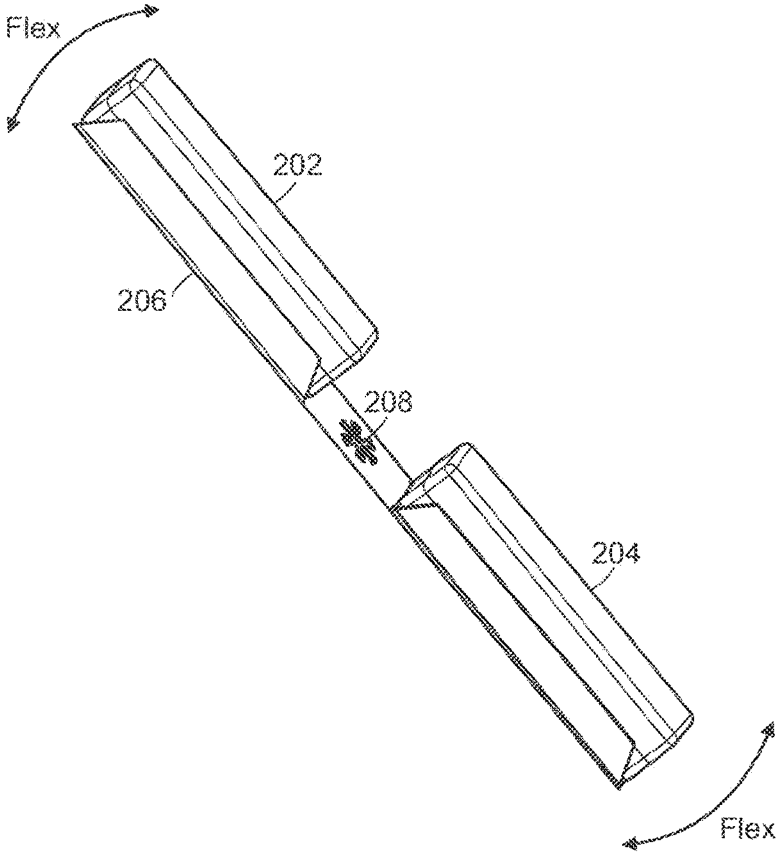
FIG. 42 illustrates a perspective view of another embodiment of a magnetic assembly consistent with the present disclosure.

FIG. 42 illustrates a perspective view of another embodiment of a magnetic assembly 200 consistent with the present disclosure. The magnetic assembly 200 comprises a pair of magnetic segments 202, 204 generally arranged in a linear alignment with one another (e.g., aligned in an end-to-end fashion) and coupled together via a flexible exoskeleton element 206. The segments 202, 204 are spaced apart via a central portion 108 of the exoskeleton 206. The central portion 208 may include a connection member for receiving a corresponding connection member of a placement device to assist in delivery of the magnetic assembly 200, as will be described in greater detail herein. The exoskeleton may be made from a resilient material that will retain its shape after deformation, such as a polymer or metal alloy. In some embodiments, the metal alloy will comprise nickel, such as nitinol. Exemplary exoskeleton embodiments are described in U.S. Pat. Nos. 8,870,898, 8,870,899, 9,763,664, the contents of each of which are incorporated by reference herein in their entirety.

The magnetic assembly 200 is configured to be delivered and deployed at a target site via a delivery device 100. As previously described, exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, exemplary embodiments provide a system including a delivery device 100 for introducing and delivering, via a minimally-invasive technique, a pair of magnetic assemblies between adjacent organs to bridge walls of tissue of each organ together to thereby form a passage therebetween (i.e., an anastomosis). The delivery device 100 is particularly useful in delivering the pair of magnetic assemblies to a target site within the gastrointestinal tract to thereby form anastomosis between gastric and gallbladder walls to provide adequate drainage from the gallbladder when blockage is occurring (due to disease or other health-related issues).

FIGS. 43A-43I illustrate various steps in deploying a pair of magnetic assemblies 200*a*, 200*b* to a target site for subsequent formation of anastomosis. In the embodiments described herein, the system generally includes a single scope 14, such as an endoscope, laparoscope, catheter, trocar, or other access device, through which a delivery device is advanced to a target site for delivering and positioning a pair of magnetic assemblies 200*a*, 200*b* for subsequent formation of anastomosis at the target site. In particular, the delivery device 100 comprises an elongate hollow body 102, such as a catheter, shaped and/or sized to fit within the scope. The delivery device includes a working channel in which a pair of magnetic assemblies 200*a*, 200*b* is loaded. The delivery device further includes a distal end 104 configured to pierce, or otherwise penetrate, through tissue.

Figure 43A:
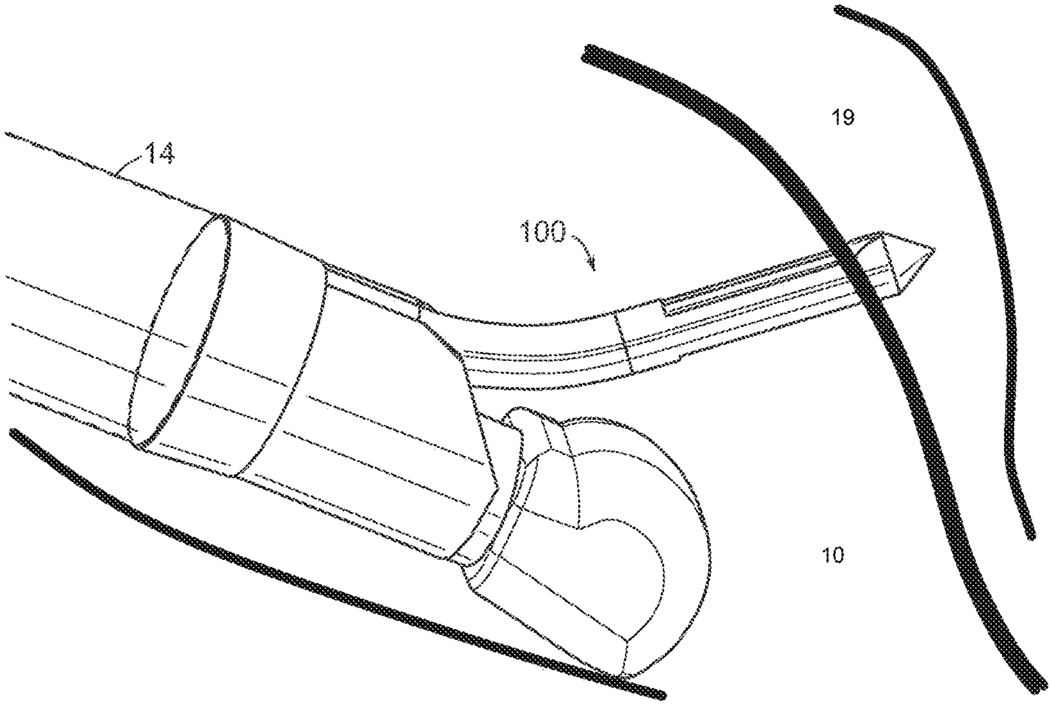
FIG. 43A illustrates advancement of a distal tip of a delivery device through respective tissue walls of adjacent organs at a target site for subsequent formation of an anastomosis therebetween.
Figure 43B:
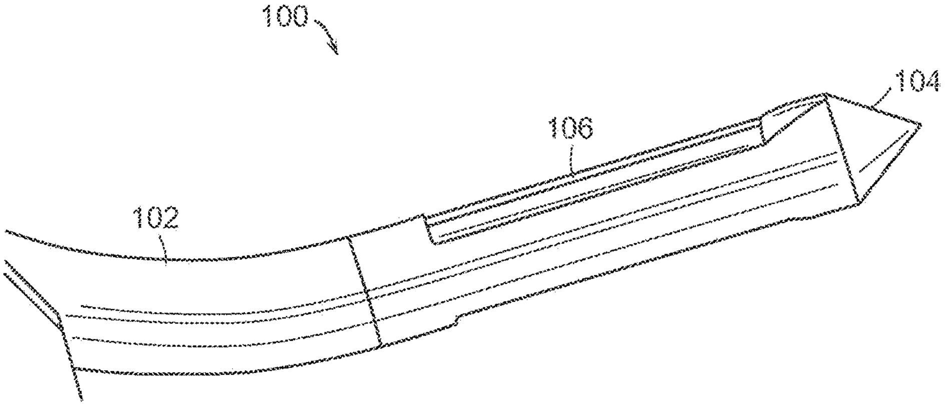
FIG. 43B is an enlarged view of a distal end of the delivery device illustrating the slot extending entirely through a side of the body of the delivery device.

For example, FIG. 43A illustrates advancement of a distal tip of a delivery device 100 through respective tissue walls of adjacent organs at a target site for subsequent formation of an anastomosis therebetween. For example, the distal end 104 may have a sharp tip for piercing tissue and/or may utilize energy to penetrate through tissue (i.e., a hot tip). The body 102 of the delivery device 100 further includes a slot or opening 106 adjacent to the distal end 104, as shown in FIG. 43B. As shown, the slot 106 extends entirely through a side of the body 102 of the delivery device 100. The slot 106 is shaped and/or sized to receive the magnetic assemblies 200*a*, 200*b* therethrough, such that the magnetic assemblies 200*a*, 200*b* pass through the working channel and exit the delivery device 100 via the slot 106. The delivery device 100 further includes a placement member 108, generally in the form of a wire or the like, that is releasably coupled to one or both of the magnetic assemblies 200*a*, 200*b* and provides a means of deploying the magnetic assemblies 200*a*, 200*b* from the distal end of the delivery device 100 via the slot 106.

Figure 43C:
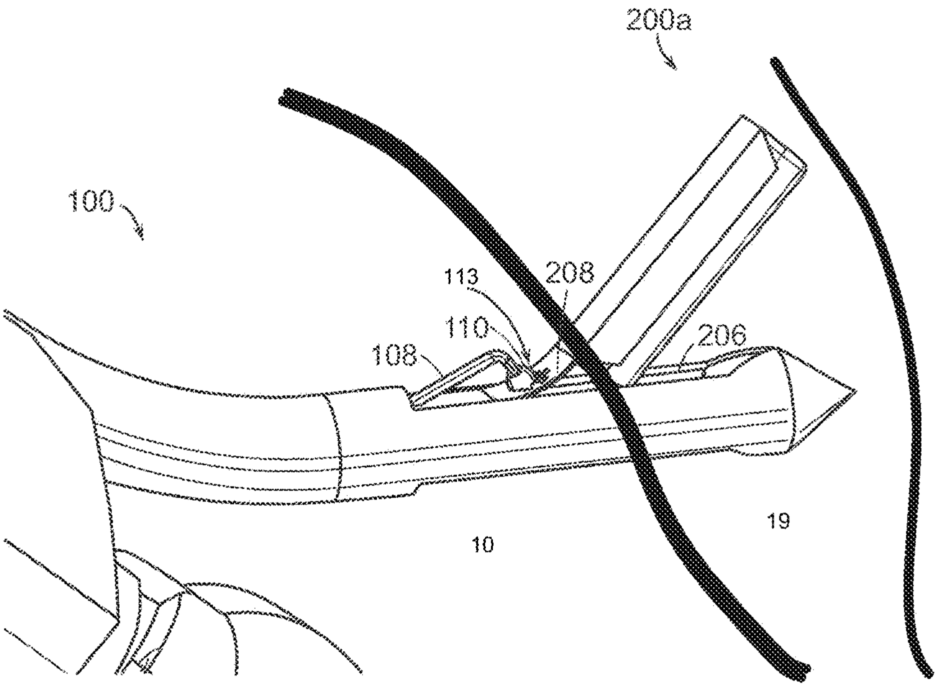
FIG. 43C illustrates delivery of a first magnetic assembly into a first organ.
Figure 43D:
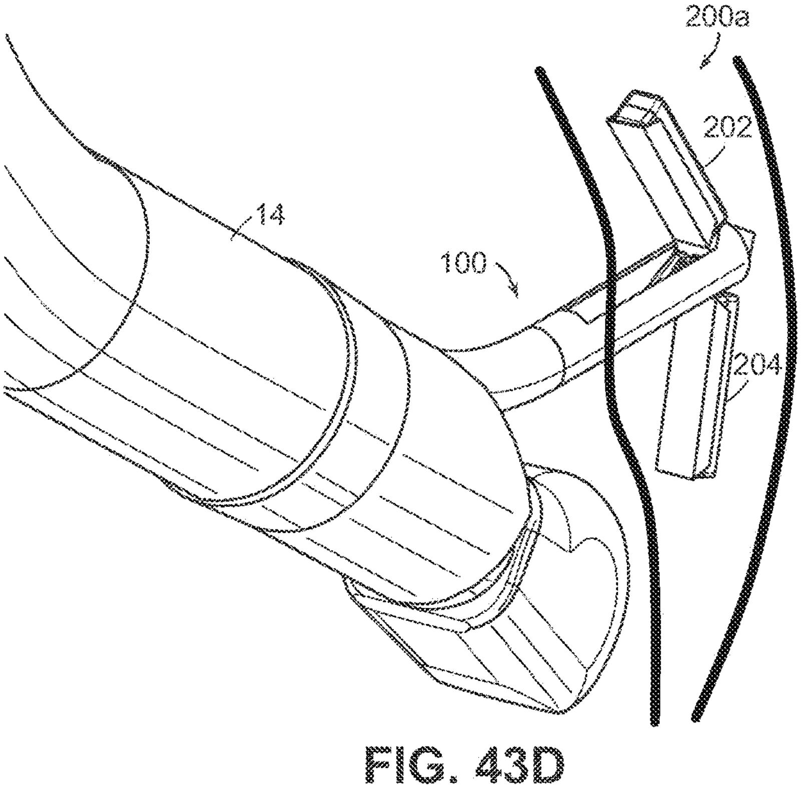
FIG. 43D illustrates deployment of the first magnetic assembly into the first organ while remaining retained within the slot of the delivery device.

During a procedure, a surgeon or other trained medical professional may advance a scope 14 (e.g., endoscope) within a hollow body of the patient and position the scope 14 at a desired anatomical location for formation of the anastomosis based on either a visual depiction of the location of the target site as provided by an imaging modality 18 providing a medical imaging procedure (e.g., ultrasound (US), wavelength detection, X-ray-based imaging, illumination, computed tomography (CT), radiography, and fluoroscopy, or a combination thereof). The surgeon may advance the distal tip 104 of the delivery device 100 through adjacent walls of a pair of organs (i.e., through a wall of the duodenum 11 and a wall of the common bile duct 19), in any manner previously described herein. Upon advancing distal end 104, including the slot 106, into the first organ (i.e., common bile duct), the surgeon may utilize the placement member 108 to manually deliver and deploy a first magnetic assembly 200*a* into the first organ via the slot. For example, FIG. 43C illustrates delivery of a first magnetic assembly 200*a* into the common bile duct. As shown, the placement member 108 include a connection member 110 at a distal end of the placement member 108, which is configured to be releasably coupled to a corresponding connection member of the central portion 208 of the exoskeleton 206 (indicated by attachment point 113). Upon advancing and extending the placement member 108 towards the distal end 104 of the delivery device 100, the first magnetic assembly 200*a* passes from the working channel of the delivery device 100 and through the slot 106 to transition into a deployed state, as illustrated in FIG. 43D. As shown, deployment of the first magnetic assembly 200*a* results in the pair of magnetic segments 202, 204 to exit the slot 106 on opposite respective sides of the body 102 of the delivery device 100 while the central portion 208 of the exoskeleton 206 remains within the slot 106. In other words, the slot 106 extends entirely through the body 102 of the delivery device 100, from one side to the other. Accordingly, when in a deployed state, the first magnetic assembly 200*a* is positioned into the first organ while remaining retained within the slot 106 of the delivery device 100.

Figure 43E:
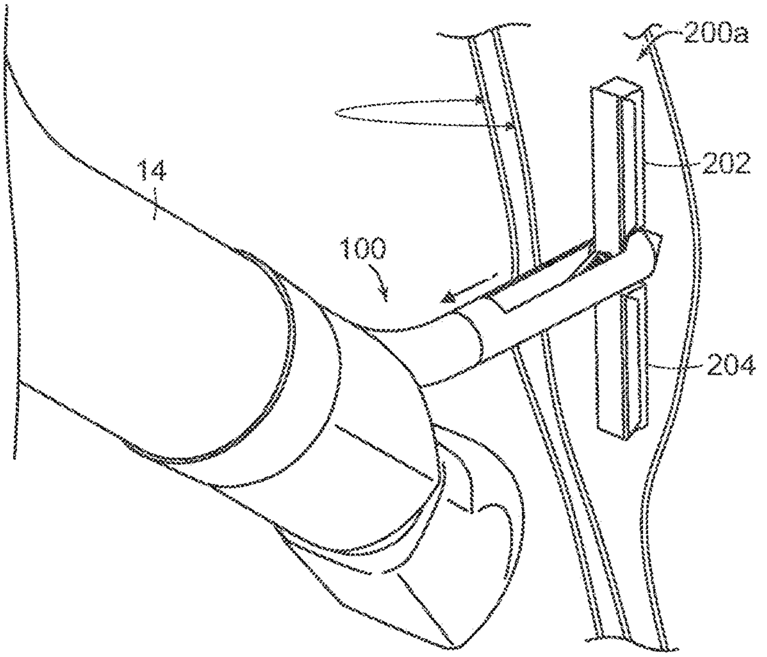
FIG. 43E illustrates a fully deployed first magnetic assembly within the first organ and pulling back of the delivery device to thereby draw the first magnetic assembly against a wall of the first organ in preparation for delivery and deployment of the second magnetic assembly in the second organ.

At this point, the surgeon need only pull back upon the delivery device 100 until the first magnetic assembly 200*a* engages the tissue of the first organ and the majority of the slot 106 is positioned within the second organ. The surgeon is able to then deliver and deploy the second magnetic assembly 200*b* into the second organ (i.e., the duodenum). FIG. 43E illustrates a fully deployed first magnetic assembly 200*a* within the first organ and pulling back of the delivery device 100 to thereby draw the first magnetic assembly 200*a* against a wall of the common bile duct in preparation for delivery and deployment of the second magnetic assembly 200*b* in the duodenum.

Figure 43F:
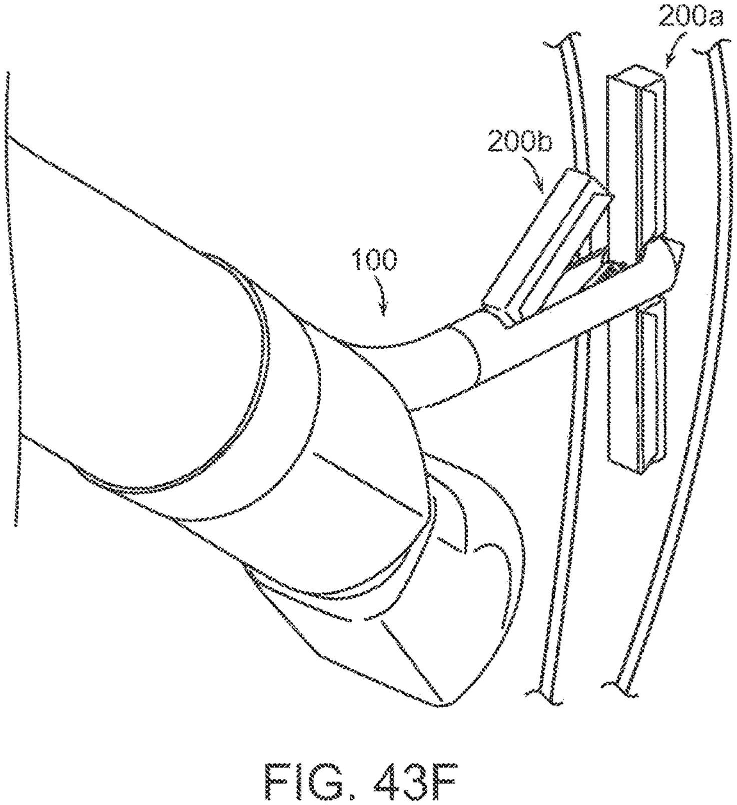
FIG. 43F illustrates delivery of the second magnetic assembly into the second organ.
Figure 43G:
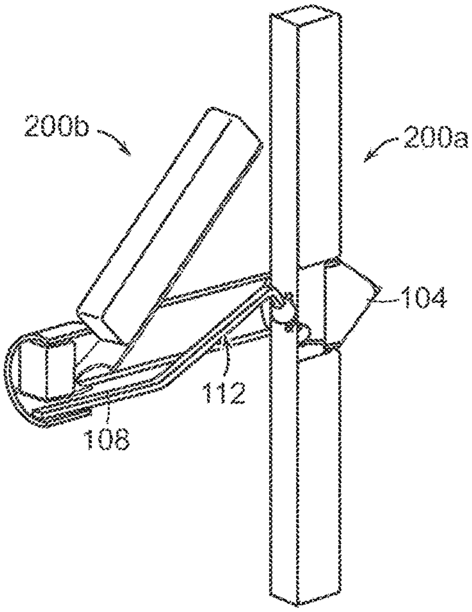
FIG. 43G is an enlarged view, partly in section, of the second magnetic assembly advancing to a deployed state.
Figure 43H:
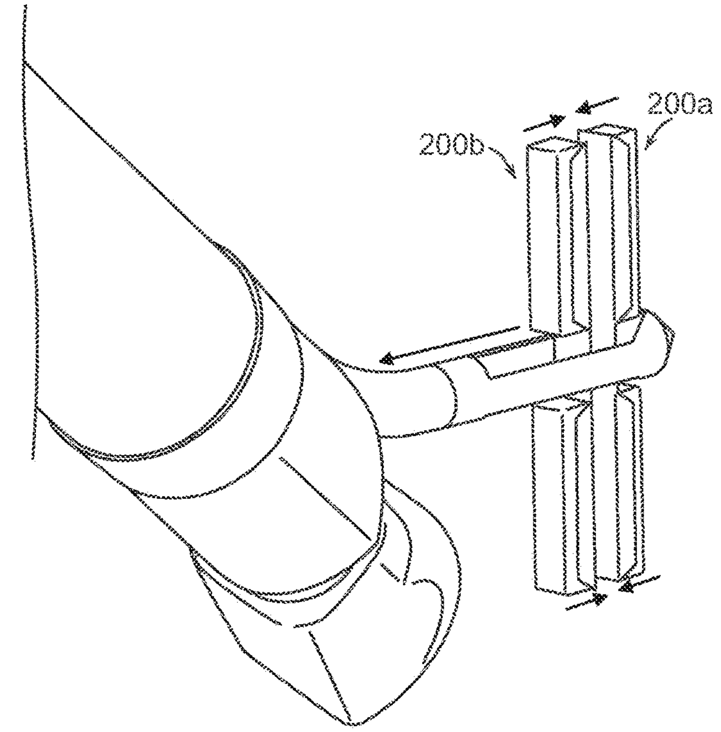
FIG. 43H illustrates the first and second magnetic assemblies in fully deployed states and coupled to one another as a result of attractive magnetic forces therebetween.

The second magnetic assembly 200*b* deploys in a similar fashion as the first magnetic assembly 200*a*, in that magnetic segments 202, 204 of the second magnetic assembly 200*b* exit the slot 106 on opposite respective sides of the body 102 of the delivery device 100 while a central portion 208 of an exoskeleton 206 remains retained within the slot 106. FIG. 43F illustrates delivery of the second magnetic assembly 200*b* into the duodenum. FIG. 43G is an enlarged view, partly in section, of the second magnetic assembly 200*b* advancing to a deployed state. As shown, as the second magnetic assembly 200*b* is advanced through the working channel and towards the slot 106, the assembly 200*b* is configured to engage a ramped section 112 of the placement member which assisted in directing at least one of the segments of the assembly 200*b* into place, as shown. FIG. 43H illustrates the first and second magnetic assemblies 200*a*, 200*b* in fully deployed states. The first and second magnetic assemblies 200*a*, 200*b* are substantially aligned with one another and, due to attractive magnetic forces, the first and second magnetic assemblies 200*a*, 200*b* will couple to one another.

Figure 43I:
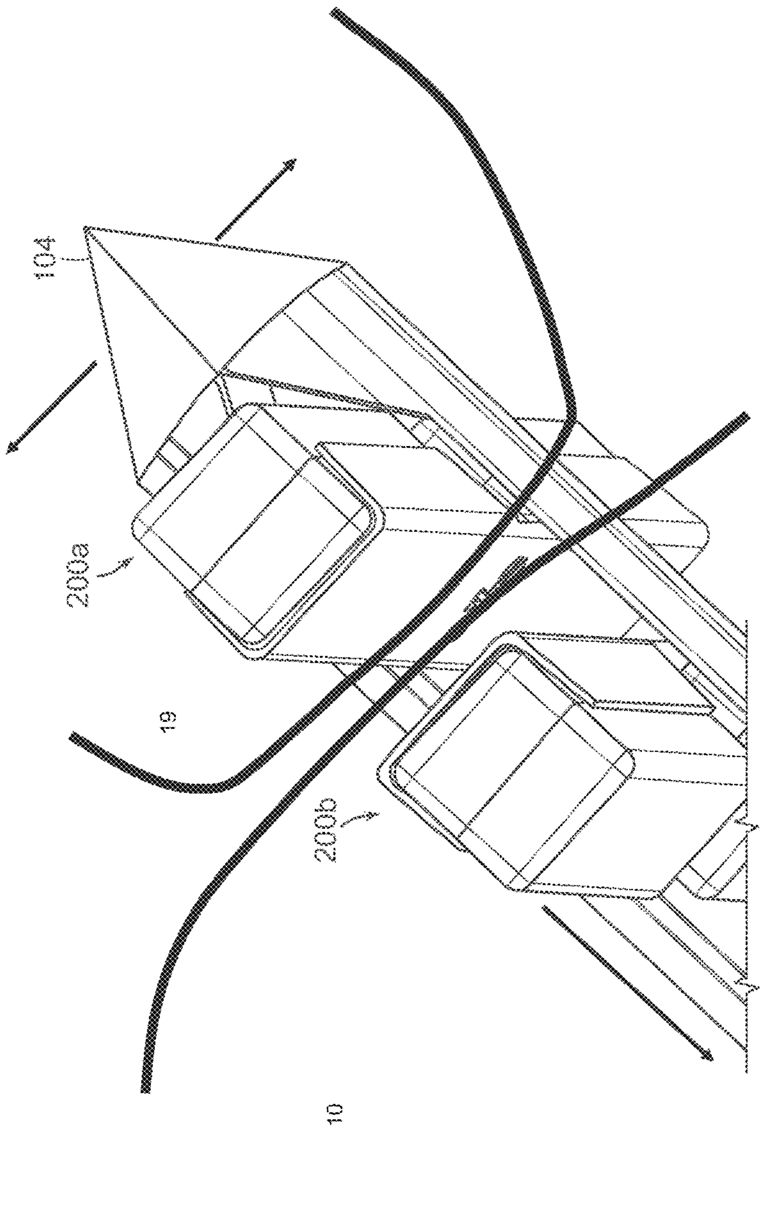
FIG. 43I illustrates the distal end of the delivery device constructed from two halves and configured to split apart to allow the delivery device to be removed from the target site while the pair of magnetic assemblies remain coupled to one another to form anastomosis at the target site.
Figure 44A:
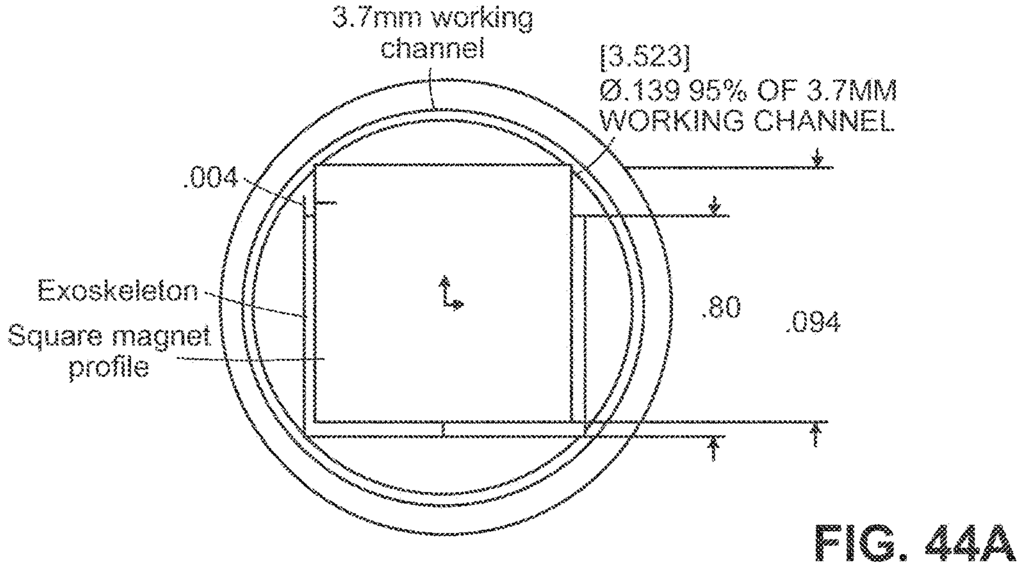
FIGS. 44A, 44B, 44C, and 44D are cross-sectional views of various profiles of magnet segments of magnetic assemblies within a working channel of a standard scope.
Figure 44B:
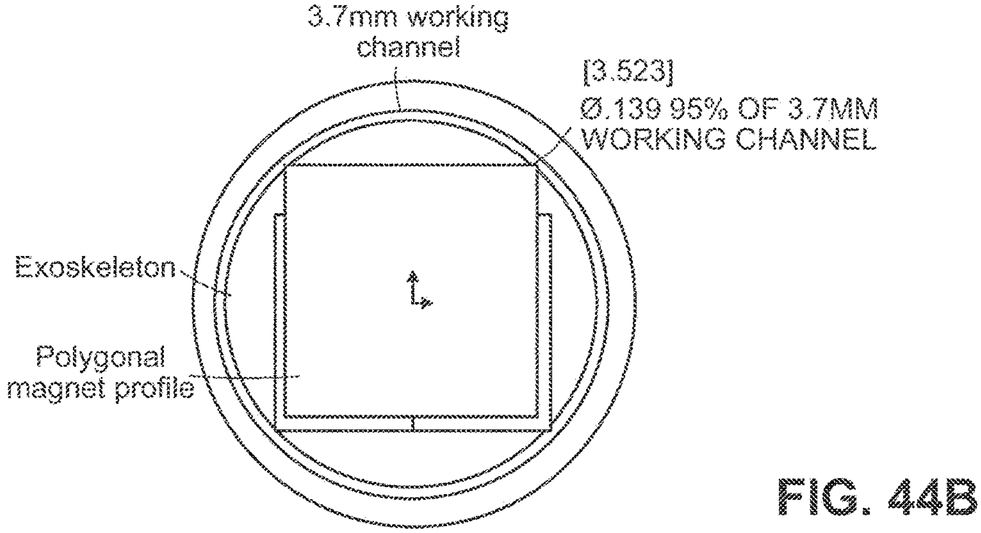
Figure 44C:
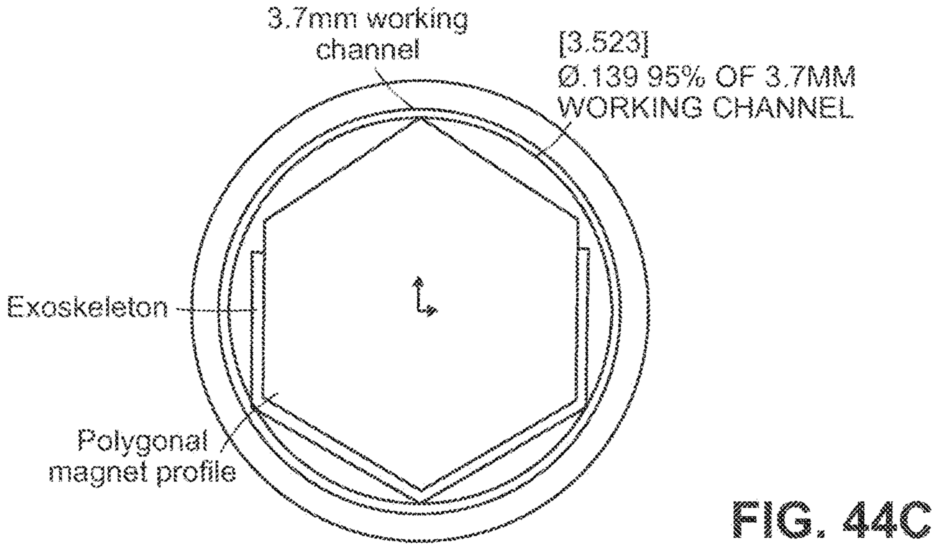
Figure 44D:
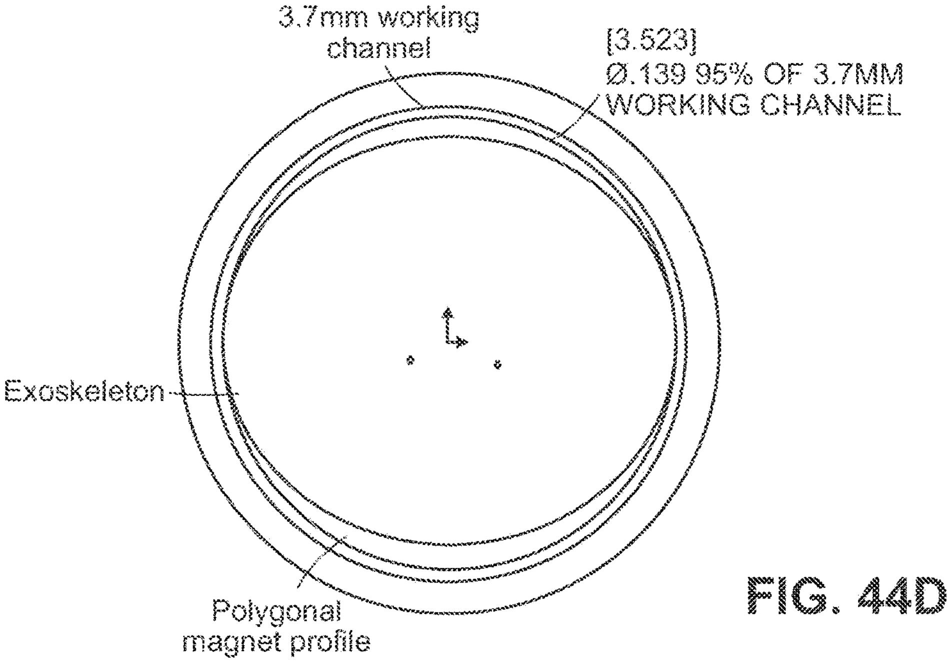

As shown in FIG. 43I, the distal end 104 of the delivery device 100 is comprised of two halves that, when in a default state, form a relatively uniform tip shape. However, the distal end comprises a deformable material (i.e., shape memory material), such that, upon application of sufficient force, the two halves will split apart. As such, once both the first and second magnetic assemblies 200*a*, 200*b* have been delivered and are effectively coupled to one another (but are still retained within the slot 106), the surgeon need only pull back on the delivery device 100 which then causes the magnetic assemblies 200*a*, 200*b* to make contact with the distal end 104 and force the two halves of the distal end 104 to split apart, allowing the distal end of the delivery device to be withdrawn from the target site while the pair of magnetic assemblies 200*a*, 200*b* remain in place. The pair of magnetic assemblies 200*a*, 200*b* compress the walls of each respective organ therebetween, subsequently forming an anastomosis between the organs (i.e., anastomosis between the duodenum and the common bile duct).

Upon deployment, each magnetic assembly has a width and a length generally corresponding to a width of a respective segment and a length that is approximately twice the length of each segment. As a result, the pair of magnetic assemblies, when coupled to one another, generally form a substantially linear package and the resulting anastomosis formed may generally be rectangular in shape, but may naturally form a round or oval shape. The resulting anastomosis may have a 1:1 aspect ratio relative to the dimensions of the magnetic assemblies. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. The magnetic assembly design overcomes such limitations.

For example, the design of the magnetic assembly, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater.

FIGS. 44A-44D are cross-sectional views of various profiles of magnet segments of magnetic assemblies within a working channel of a standard scope. The cross-sectional areas of magnets are illustrated, showing polygons as well as ellipses and circles taking between 10 and 95 percent of the annular space of the working channel. With the guidelines for the magnetic profile being in place, the next constraint for the device is the axial ratio of a minimum of 6:1 and a maximum of 50:1. This segmented length once assembled in the body can have either a regular or irregular shape.

FIG. 45 provides a listing of some exemplary working channel sizes considered usable/feasible to deploy a magnetic array with a cage to produce an anastomosis. These sizes do not limit future capabilities as scope channel sizes increase/decrease with market and device changes. The summary of sizing can be summarized into: 1.0 mm-6.0 mm (including a bleed scope called the "clot buster") with one particular sized device designed around the 3.7 mm.

Accordingly, the delivery device of the present disclosure produces a low-profile linear anastomosis that would allow certain complications, particularly those associated with blockage of the common bile duct, to be mitigated. In particular, patients experiencing a blockage of the common bile duct often undergo some sort of procedure to either remove the blockage or allow drainage to provide relief of jaundice/infection and hepatic portal complications. A common procedure is a sphincterotomy, or some sort of draining stent placement procedure. There are procedures which present decompression of the bile duct in a traditional way, but are not possible in a minimally noninvasive manner. Such procedures include, for example, a sphincterotomy, which is not possible due to inability to cannulate the common bile duct, inability to account for anatomical alterations, particularly during heavily diseased states. Utilizing the magnetic closure force profile as described herein would allow minimal bleeding and create a semi-permanent slit profile. This slit profile would help to resist "sump syndrome" and help to create a drainage point which would remain effectively infection free.

Another concept includes a medical device designed for a user, who requires a more effective means of creating an opening between a circular stapler or compression anastomosis device, therefore creating or expanding an enterotomy. Certain embodiments will fit down the existing channel of an endoscope or other delivery device such as a laparoscope or catheter and provide effective tissue desecration, allowing either nutrient passage or tissue desecration. Current methods are time-consuming, ineffective, and often life-threatening. This device offers an efficient alternative that makes the procedure quicker, safer, easier, and more cost-effective. The product offers a simple solution to a potential life-threatening problem, including the ability to decompress an organ or allow nutrient bypass immediately.

This concept covers different embodiments of a mechanism/tool for creating an enterotomy between magnetic compression devices (e.g., via cutting, dissecting, dilating, cauterizing, or the like). The mechanism/tool is deliverable to the target site via an existing channel of an endoscope or delivery device used for the delivery or deployment of the magnetic compression devices. Embodiments include deployable cutting mechanisms including a mechanism for physically shearing tissue or utilizing energy to cauterize and desecrate tissue (i.e., hot needle or electrode). Certain exemplary embodiments include a corkscrew member (e.g., needle) attached to end of a rotatable catheter and either a coring needle or a hot needle to be used in conjunction with the corkscrew member. In particular, the corkscrew member can be rotated while piercing the tissue, thereby drawing the catheter towards the tissue wall. Once the catheter's tip is at an adequate depth, the coring needle or hot needle can be engaged and advanced into the tissue to create an enterotomy.

Exemplary embodiments include an apparatus that has capabilities to cut, dissect, dilate and cauterize tissue, individually or used in conjunction with other methods, between one or more mating devices (e.g., compression anastomosis devices) creating and/or capturing an open conduit for compression or decompression or nutrient bypass, e.g., while maintaining concentricity with a deployment channel.

Exemplary embodiments also include an apparatus that has ability to be delivered into an adjacent wall which then can act as a conduit to deliver a compression anastomosis device.

Exemplary embodiments also include an apparatus that allows tissue to be sheared, dilated or excised between one or more compression devices.

Exemplary embodiments also include an apparatus with a retractable sharp tip or energy to provide tissue desecration.

In some embodiments there can be two exemplary cutting mechanisms, specifically a cap configured to "guillotine" tissue (e.g., including edging or grooves to mechanically cut on using energy to excise the tissue) and a compression device with cutting mechanism that can be used with or without a cap to capture and cut tissue.

Figure 46:
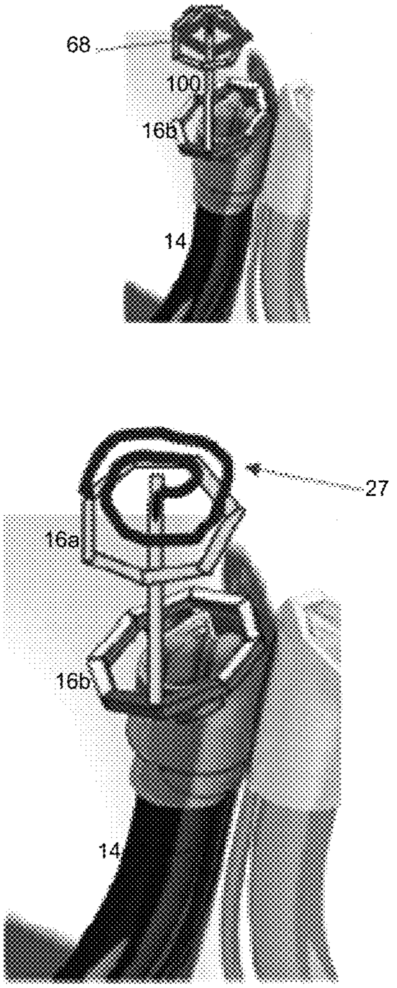
FIG. 46 is a schematic diagram showing two exemplary cutting mechanisms, specifically a mechanical cutting mechanism and an electronic cutting mechanism (e.g., using RF or electrode/heat for tissue desecration between one or more desecration devices.

FIG. 46 is a schematic diagram showing two exemplary cutting mechanisms, specifically a mechanical cutting mechanism 68 and an electronic cutting mechanism 27 (e.g., using RF or electrode/heat for tissue desecration between one or more desecration devices).

Certain exemplary embodiments use a corkscrew needle at the end of a torqueable/rotatable catheter, the catheter could be advanced to a lumen wall and then corkscrewed into the wall to a certain depth. Because of the corkscrew action, the user would have much more control on how deep into the tissue the end of the catheter would advance. Once the catheter's tip is at an adequate depth, the second member could be engaged and advanced. This could be either a coring needle (FIG. 47) or a hot needle (FIG. 48). When engaged, the second member would drive into the tissue captured within the corkscrew member and the overall distance the second member could travel would be limited such that the second member could not advance further than the distal end of the corkscrew member. The embedded corkscrew member would provide counter force to driving forward of the second member and the corkscrew member could shroud the second member from doing damage to any tissue beyond the depth the corkscrew member was engaged with (i.e. the opposite wall of the distal lumen).

Figure 47:
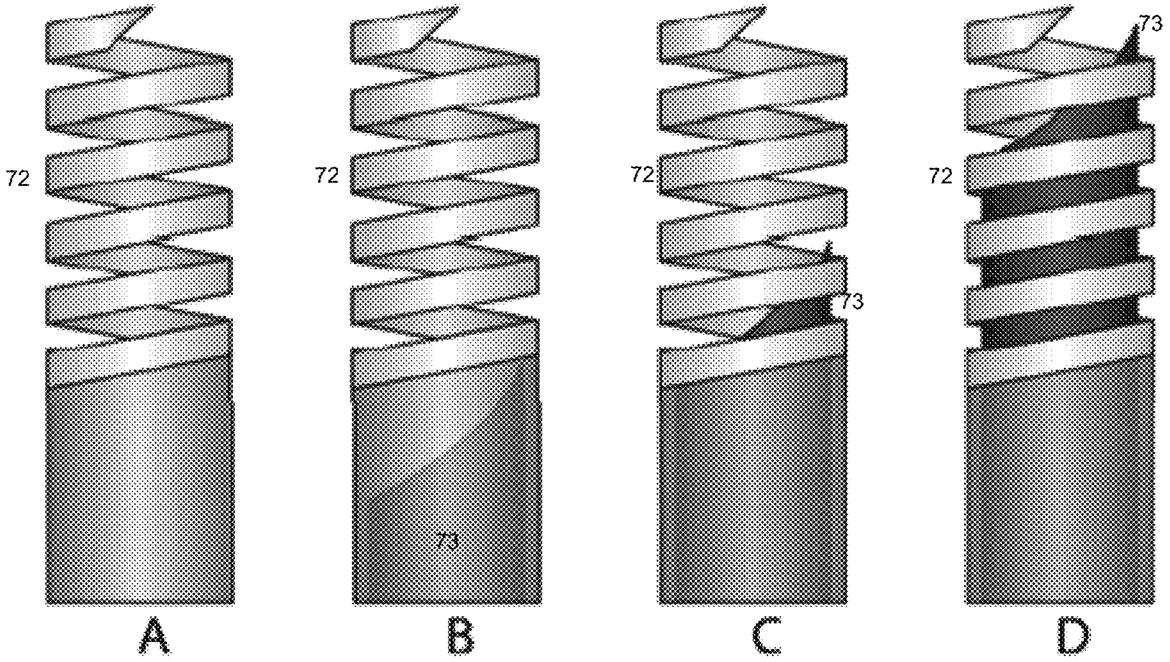
FIG. 47 is a schematic diagram showing a coring needle device, in accordance with one exemplary embodiment.
Figure 48:
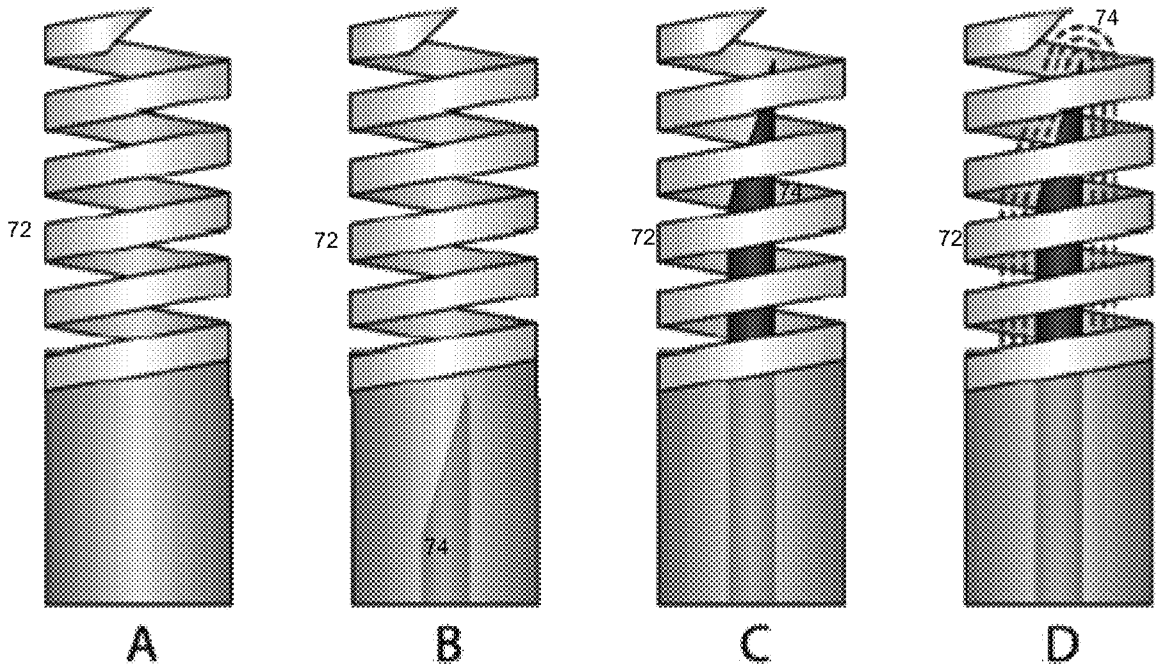
FIG. 48 is a schematic diagram showing a hot needle device, in accordance with one exemplary embodiment.

FIG. 47 is a schematic diagram showing a coring needle device, in accordance with one exemplary embodiment. FIG. 47(A) shows a corkscrew member rigidly attached to the end of a rotatable catheter. The distal tip of the corkscrew member is a needle point so that it can be 'screwed' into the tissue. FIG. 47(B) shows a coring needle residing within the catheter until it is advanced. FIG. 47(C) shows a coring needle advancing through tissue encapsulated within the corkscrew. The corkscrew member provides counterforce to push against so the tissue doesn't back away. In certain exemplary embodiments, the coring needle is limited to advance no further than the distal end of the corkscrew to keep the needle tip shrouded, as depicted in FIG. 47(D).

FIG. 48 is a schematic diagram showing a hot needle device, in accordance with one exemplary embodiment. FIG. 48(A) shows a corkscrew member rigidly attached to the end of a rotatable catheter. The distal tip of the corkscrew member is a needle point so that it can be 'screwed' into the tissue. FIG. 48(B) shows a hot needle residing within the catheter until it is advanced. FIG. 48(C) shows a hot needle advanced into the tissue encapsulated within the corkscrew but limited not to be able to advance beyond the distal edge of the corkscrew. FIG. 48(D) shows electro-surgical energy being applied through the needle, thereby desiccating and destroying the targeted tissue. In both cases, once the second member has been advanced, it can then be retracted and the corkscrew member can be pulled free (since the tissue has either been cored out or desiccated).

Control Members

FIGS. 49, 50, 54A, 54B, 55A, 55B, 56A, 56B, 57A, 57B and 58 show various exemplary embodiments of mechanisms/tools used to create an enterotomy between compression anastomosis devices. The mechanisms/tools are deployed though a channel of an endoscope or delivery device then capture and center a compression anastomosis device in the proximal lumen. The devices utilize a penetrating tip to create an enterotomy between lumens that is axially aligned with the delivery channel. The penetrating tip's support serves as a guide for transluminal deployment of a compression anastomosis device and a control member into the distal lumen. The control member can include an array of at least one arm/member which manipulate connecting members (i.e. sutures) connected to the distally deployed compression device. The control member can be compressed to less than the diameter of the enterotomy, deployed into the distal lumen, and expanded to a diameter greater than the enterotomy to increase the control of the connecting members and dilate the enterotomy. The connecting members can be used to pull the compression device against the control members, align its mating axis with the deployment channel through rotational movement, and mate it with the compression device in the proximal lumen through translational movement; capturing the enterotomy. After mating the compression devices, the control member can be compressed to less than the diameter of the enterotomy and retracted back into the working channel along with the penetrating tip, releasing the connecting members and leaving the mated compression anastomosis devices in place. Among other things, such devices can use a monopolar or bipolar energized hot tip, a piercing tip (which may be heated), or a cutting mechanism (e.g., a mechanical cutting mechanism, an RF/ultrasonic cutting mechanism, a heated cutting mechanism, etc.). A coring needle or other delivery mechanism may be used to aid in positioning and securing the piercing or cutting mechanism to the tissue.

Thus, certain exemplary embodiments include an apparatus that has ability to deliver a control mechanism consisting of an array of at least one articulating member into an adjacent lumen that expands to a diameter greater than the created enterotomy in order to increase the mechanical advantage used to control connecting members attached to a distally deployed compression anastomosis device. The control mechanism's increased diameter can also serve as a tool to dilate and/or expand the created enterotomy.

Additional exemplary embodiments include an apparatus that allows for control and manipulation of a compression device in a distal lumen using connecting members, creating alignment within 15° between the deployment channel axis and the compression device's mating axis. The control mechanism allows movement in distal, proximal, and rotational directions and can couple and decouple mated compression anastomosis devices.

Additional exemplary embodiments include an apparatus with a biased sharp cutting tip or monopolar or bipolar energized tip to provide tissue desecration that creates an enterotomy centered coaxially with a delivery device's working channel. The tip's support serves as a guide for deployment of a control member and a compression anastomosis device into the distal lumen, wrapping it in a prescribed manner around the support to orient and present the compression device upon deployment. In certain configurations, the tip may also act as a control member (i.e. an energized basket) and/or be used to dilate the created enterotomy.

Another concept includes an expandable/contractible mechanism configured to help control and manipulate the distal anastomosis device within the distal lumen, e.g., as the delivery device is retracted into the proximal lumen for deployment of the proximal anastomosis device, and also to help position/align the distal anastomosis device for proper coupling with the proximal anastomosis device as the two anastomosis devices are brought into proximity with one another.

Figure 49:
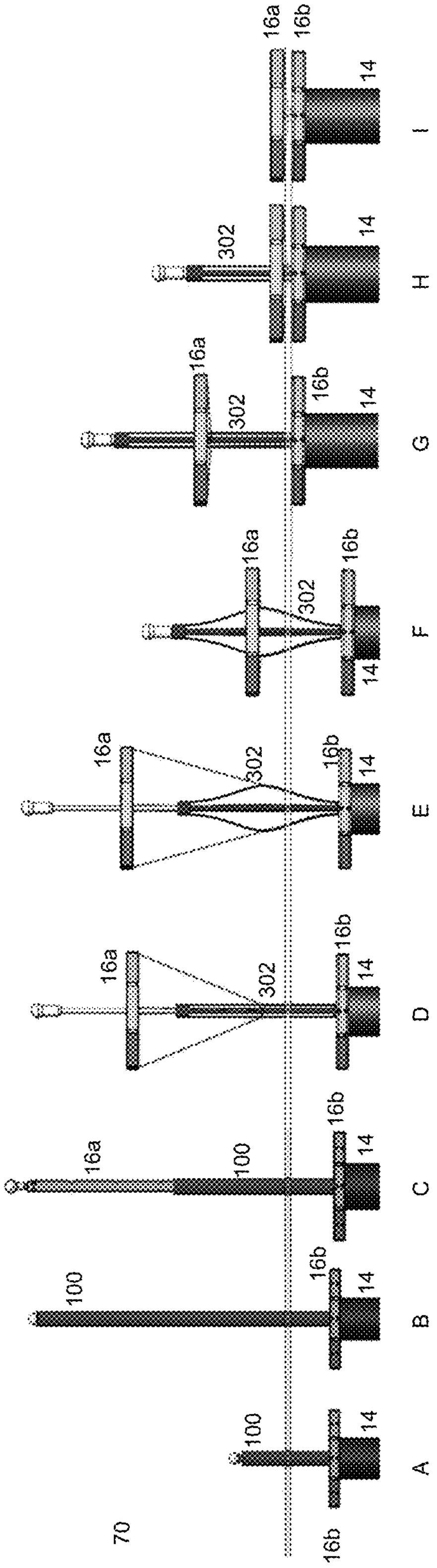
FIGS. 49 and 50 show various exemplary embodiments of mechanisms/tools used to create an enterotomy between compression anastomosis devices.

FIG. 49 illustrates the deployment of an anastomosis device. After the proximal magnet 16*b* is deployed (FIG. 49(A)), the piercing tip of the delivery device 100 pierces through the lumen walls into the distal lumen 70, creating an enterotomy (FIG. 49(B)). By pulling back on the delivery device 100, the distal magnet 16*a* is deployed (FIG. 49(C)) and self-assembles (FIG. 49(D)). By continuing to pull back on the delivery device 100, a control member 302 is deployed (FIG. 49(D)) in the space between the lumens in the created enterotomy. In some embodiments and as pictured in FIG. 59, the control member is a basket shape. The control member 302 expands to a diameter greater than that of the enterotomy, thus expanding the enterotomy (FIG. 49(E)). The control member engages with the distal magnet 16*a*, and assists alignment with the proximal magnet 16*b* (FIG. 49(F)). The control member 302 also adds additional mechanical advantage to the distal magnet 16*a* to bring the two anastomosis devices 16*a*, 16*b* together. The two magnets 16*a*, 16*b* are brought together by attractive magnetic forces and extra force by the control member 302. The user further pulls back on the delivery device 100, and the control member 302 contracts to a diameter less than that of the enterotomy (FIG. (G)) and is retracted into the delivery device 100 (FIGS. (H), (I)). The delivery device 100 and control member 302 may then be removed from the enterotomy and from the patient.

Figure 50:
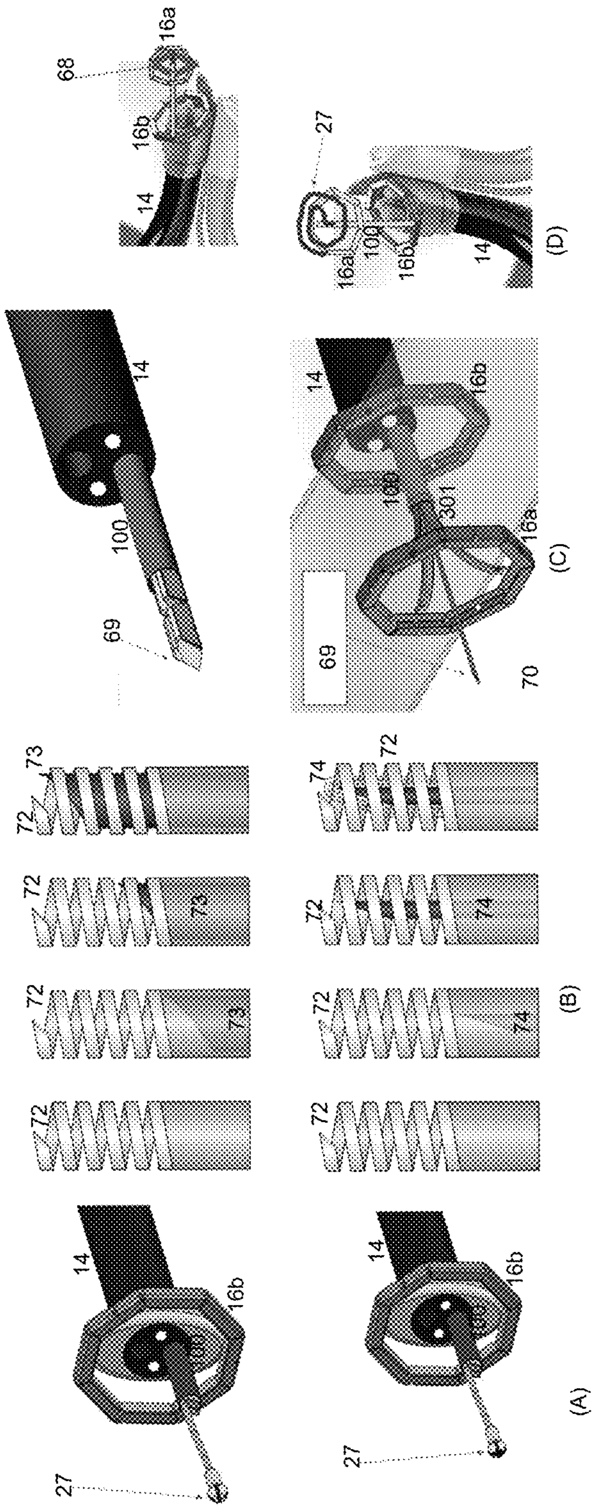

FIG. 50 illustrates various embodiments of piercing tips on the distal end of the delivery device used to create an enterotomy. FIG. 50(A) illustrates a monopolar or bipolar energy hot tip 27 used to desecrate tissue and thus create an enterotomy. Once the proximal magnet 16*b* is deployed, the user may advance the delivery device against the target tissue wall. Activating the energy of the distal tip of the delivery device 100 allows monopolar or bipolar energy to desecrate the tissue, forming an enterotomy between the lumens. The tip 27 is further advanced into the distal lumen, and by pulling back on the delivery device 100 the distal magnet is deployed. Once deployed, the distal magnet aligns with and mates with the proximal magnet due to attractive magnetic forces. By pulling back further on the delivery device, the magnets are left in place, creating an anastomosis, and the delivery device is removed from the enterotomy and the patient.

FIG. 50(B) illustrates a schematic diagram showing a coring needle device, in accordance with one exemplary embodiment. The top row of FIG. 50(B) shows a corkscrew member 72 is rigidly attached to the end of a rotatable catheter. The distal tip of the corkscrew member 72 is a needle point so that it can be 'screwed' into the tissue. A coring needle 73 residing within the catheter until it is advanced. A coring needle 73 advancing through tissue is encapsulated within the corkscrew 72. The corkscrew member 72 provides counterforce to push against so the tissue doesn't back away. In certain exemplary embodiments, the coring needle 73 is limited to advance no further than the distal end of the corkscrew to keep the needle tip shrouded. FIG. 50(B) also shows a schematic diagram showing a hot needle device in the bottom row of FIG. 50(B), in accordance with one exemplary embodiment. A corkscrew member 72 is rigidly attached to the end of a rotatable catheter. The distal tip of the corkscrew member 72 is a needle point so that it can be 'screwed' into the tissue. A hot needle 74 resides within the catheter until it is advanced. FIG. 50(B) shows a hot needle 74 advanced into the tissue encapsulated within the corkscrew 72 but limited not to be able to advance beyond the distal edge of the corkscrew 72. Electro-surgical energy is applied through the needle 74, thereby desiccating and destroying the targeted tissue. In both cases, once the second member has been advanced, it can then be retracted and the corkscrew member 72 can be pulled free (since the tissue has either been cored out or desiccated).

FIG. 50(C) illustrates a piercing tip 69 used to create an enterotomy. The piercing tip 69 is housed within the delivery device 100, and is advance through the tissue wall, desecrating the tissue and creating an enterotomy. Once the enterotomy is created, the distal tip of the delivery device 100 is advanced through the enterotomy into the distal lumen. Once the delivery device 100 is in the distal lumen 70, the user pulls back on the delivery device 100, thus deploying the distal magnet 16*a*. FIG. 50(C) also depicts a wire jaw control member 301. After the distal magnet 16*a* is deployed, the user pulls back on the delivery device 100 and deploys the control member 301 into the enterotomy. The control member 301 expands to a diameter greater than that of the enterotomy, thus expanding the enterotomy. The control member 301 engages with the distal magnet 16*a*, and assists alignment with the proximal magnet 16*b*. The control member 301 also adds additional mechanical advantage to the distal magnet 16*a* to bring the two anastomosis devices 16*a*, 16*b* together. The two magnets 16*a*, 16*b* are brought together by attractive magnetic forces and extra force by the control member. The user further pulls back on the delivery device 100, and the control member 301 contracts to a diameter less than that of the enterotomy and is retracted into the delivery device 100 along with the piercing tip. The delivery device 100 and control member 301 may then be removed from the enterotomy and subsequently from the patient.

FIG. 50(D) illustrates an RF or electrode 27 for tissue desecration between one or more desecration devices as a cutting mechanism. FIG. 50(D) illustrates an exemplary cutting mechanism, specifically a mechanical cutting mechanism and an electronic cutting mechanism 68 (e.g., using RF or electrode/heat for tissue desecration between one or more desecration devices).

Figure 51:
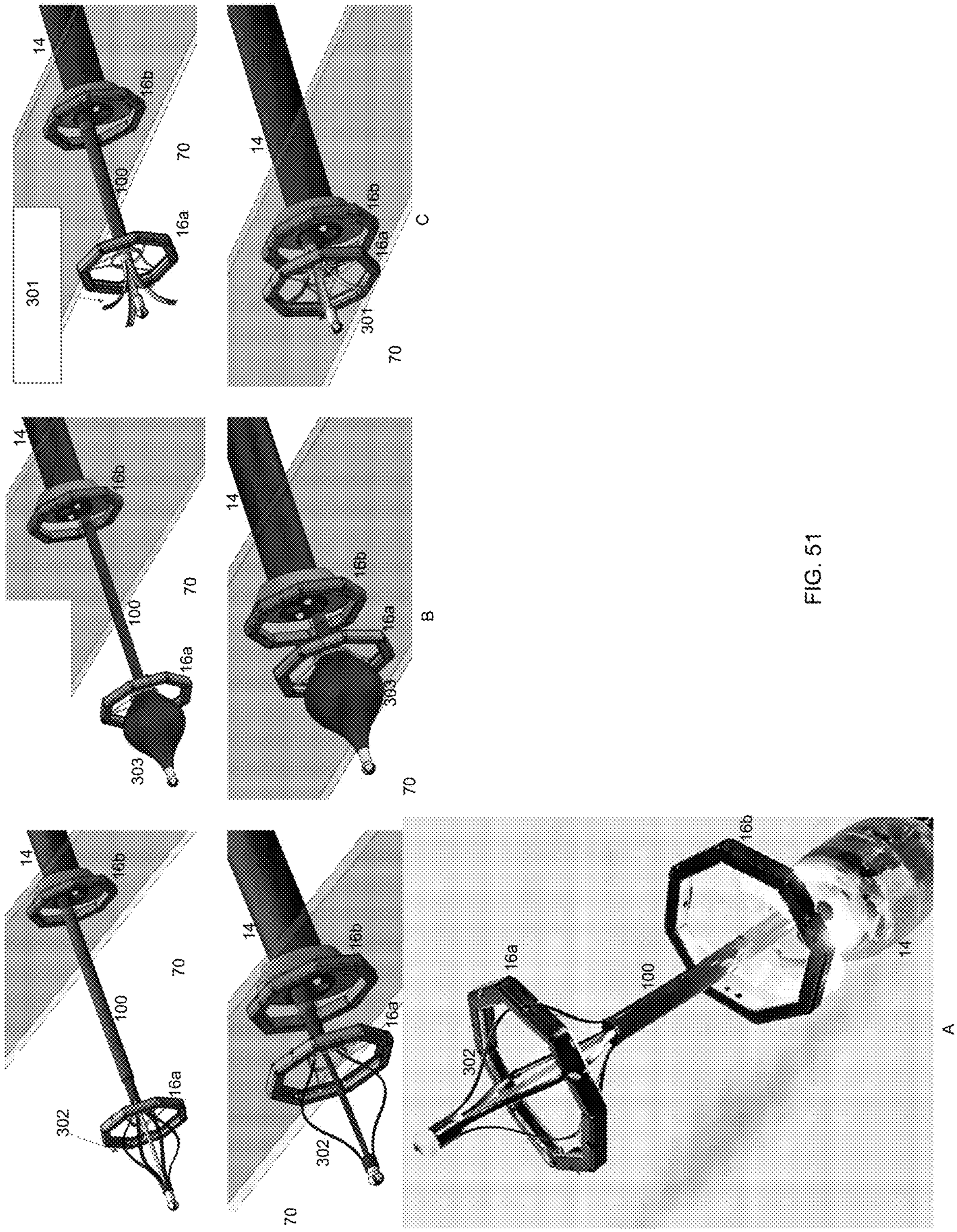
FIG. 51 shows three expandable/contractible configurations providing for backstop control and manipulation of an anastomosis device, in accordance with various exemplary embodiments.

FIG. 51 shows three expandable/contractible control members providing for backstop control and manipulation of an anastomosis device, in accordance with various exemplary embodiments. The configurations in A show a basket backstop control member 302. Once the proximal 16*b* and distal magnets 16*a* are deployed, the delivery device 100 is further advanced past the distal magnet 16*a* into the distal lumen 70. By pulling back on the delivery device 100, the control member 302 is deployed in a contracted position from the delivery device 100. The user pulls back on the delivery device 100, and the basket backstop control member 302 expands to a diameter greater than that of the distal magnet assembly 16*a*. The control member 302 engages with the distal magnet 16*a* as shown in FIG. 51A, so as to assist with alignment of the magnetic assemblies and provide additional mechanical advantage to the distal magnet 16*a* in order to pair the assemblies through the tissue walls. Once the magnetic assemblies 16*a*, 16*b* are mated, the control member 302 contracts to a diameter less than that of the magnetic devices and is retracted into the delivery device 100 for removal from the patient.

The B configurations of FIG. 51 show a balloon backstop 303 control member. Once the proximal 16*b* and distal magnets 16*a* are deployed, the delivery device 100 is further advanced past the distal magnet 16*a* into the distal lumen 70. By pulling back on the delivery device 100, the balloon backstop control member 303 is deployed in a contracted position having been stored in the delivery device 100. The user pulls back on the delivery device 100, and the balloon backstop control member 303 is inflated to a diameter greater than that of the distal magnet assembly 16*a*. The control member 303 engages with the distal magnet 16*a* as shown in FIG. 51B, so as to assist with alignment of the magnetic assemblies 16*a*, 16*b* and provide additional mechanical advantage to the distal magnet 16*a* in order to pair the assemblies through the tissue walls. Once the magnetic assemblies are mated, the control member 303 contracts to a diameter less than that of the magnetic device, and is retracted into the delivery device 100 for removal from the patient.

The C configurations of FIG. 51 show a "flower petal" backstop control member 301. The "flower petal" backstop 301 works similarly to the other backstops, in that once the proximal 16*b* and distal magnets 16*a* are deployed, the delivery device 100 is further advanced past the distal magnet 16*a* into the distal lumen 70. By pulling back on the delivery device 100, the control member 301 is deployed in a contracted position from having been stored in the delivery device 100. The user pulls back on the delivery device 100, and the "flower petal" backstop control member 301 expands to a diameter greater than that of the distal magnet assembly 16*a*. The control member 301 engages with the distal magnet 16*a* as shown in FIG. 51C, so as to assist with alignment of the magnetic assemblies 16*a*, 16*b* and provide additional mechanical advantage to the distal magnet 16*a* in order to pair the assemblies through the tissue walls. Once the magnetic assemblies 16*a*, 16*b* are mated, the control member 301 contracts to a diameter less than that of the magnetic device, and is retracted into the delivery device 100 for removal from the patient.

Of course, other control member configurations are possible based on the concept of an expandable/contractible backstop.

Figure 52:
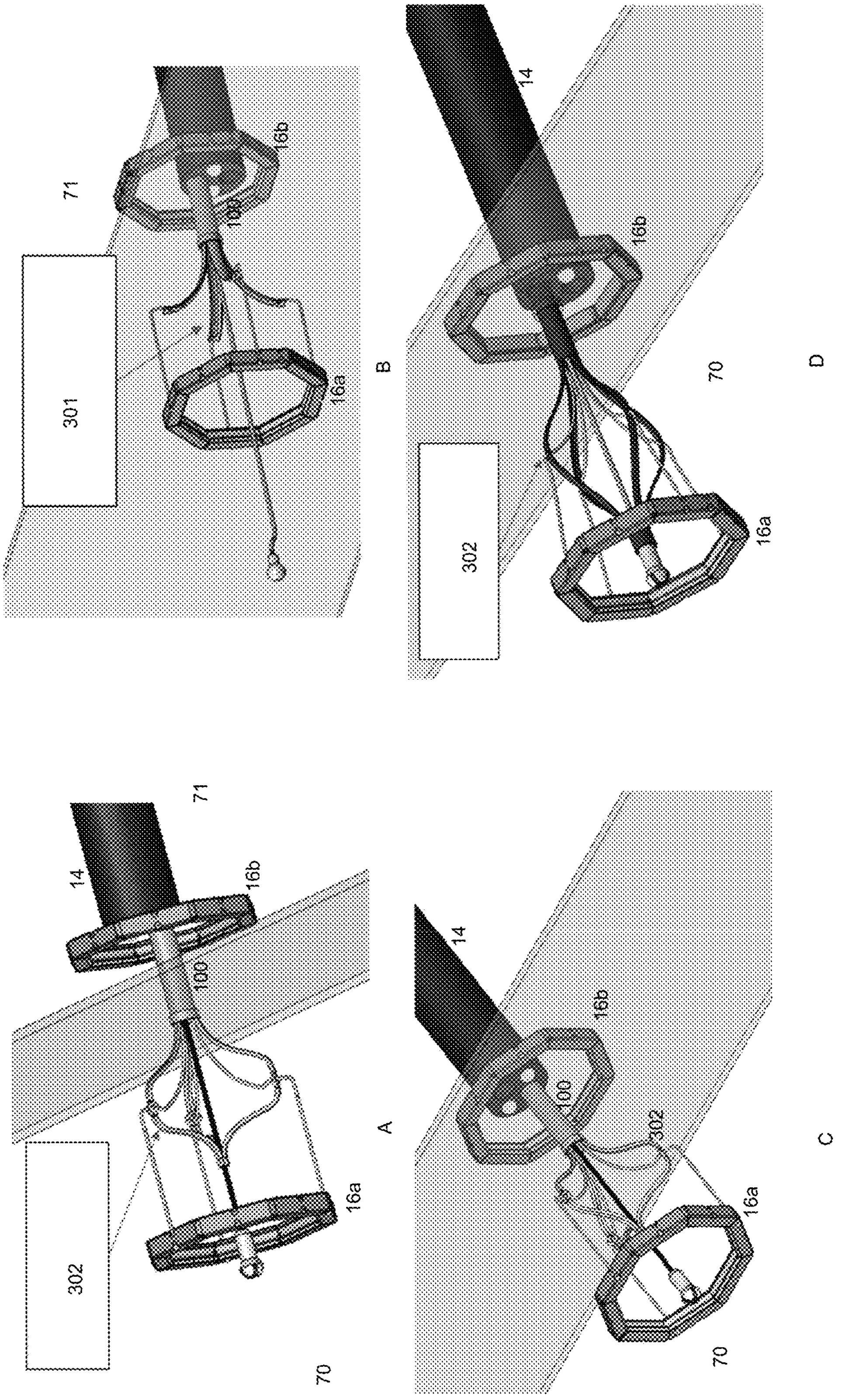
FIG. 52 shows three expandable/contractible configurations providing for affirmative control and manipulation of an anastomosis device, in accordance with various exemplary embodiments.

FIG. 52 shows three expandable/contractible mechanisms providing for affirmative control and manipulation of an anastomosis device, in accordance with various exemplary embodiments. A and C configurations show a wire basket control member 302. The B configuration shows a "flower petal" control member 301. The D configuration shows a tubing basket control member 302. Of course, other configurations are possible based on the concept of such a control/manipulation and alignment mechanism, as shown in but not limited to FIGS. 54A, 54B, 55A, 55B, 56A, 56B, 57A, 57B, and 58. Once the magnetic assemblies are deployed, the user pulls back on the delivery device 100 to deploy the control member 302 into the enterotomy between the lumens 70, 71 in a contracted position having been stored in the delivery device 100. By pulling back on the delivery device 100, the user can expand the control member 302 to a diameter greater than that of the enterotomy thus expanding the enterotomy. The control member 302 then engages the distal magnet 16*a*, manipulating it so as to align the two magnetic devices 16*a*, 16*b*. Once the devices 16*a*, 16*b* are aligned, the control member 302 may be used to add additional force to the distal magnet 16*a* in order to mate the two anastomosis devices across the tissue wall. Once the magnets are paired, the user pulls back the delivery device, and the control member contracts to a diameter less than that of the enterotomy and is retracted into the delivery device 100 for removal from the patient.

Mechanisms of the types shown in FIGS. 51, 52, 54A, 54B, 55A, 55B, 56A, 56B, 57A, 57B, and 58 are configured for creating alignment within 15° between the deployment channel axis and the compression device's mating axis.

Figure 54A:
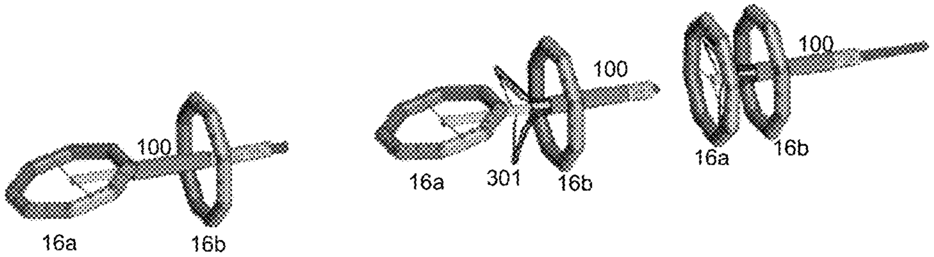
FIG. 54A shows when the proximal magnet deployed in the proximal lumen, the device extends into the distal lumen and the distal magnet is deployed (A). The jaw control mechanism is deployed (B). The distal magnet is manipulated with the jaw acting as a support (C).

FIGS. 54A, 54B, 55A, and 55B show another concept of an expandable/contractible mechanism configured to control and manipulate the distal anastomosis device 16*a* within the distal lumen 70 configured as a wire jaw shape. FIG. 54A illustrates a front view of a wire jaw control member 301 being deployed. After the proximal 16*b* and distal 16*a* magnets are deployed, the user pulls back on the delivery device 100 to deploy the wire jaw control member 301. The control member 301, having been in a contracted position while stored in the delivery device 100, expands to a diameter greater than that of the enterotomy. The wire jaw control member 301 engages with the distal magnet 16*a* to manipulate and align the distal magnet 16*a* with the proximal magnet 16*b*. Once the magnets 16*a*, 16*b* are aligned and paired, the user pulls back on the delivery device 100 to contract the wire jaw control member to a diameter less than that of the enterotomy, and retract the control member 301 into the delivery device 100 for removal from the patient.

Figure 54B:
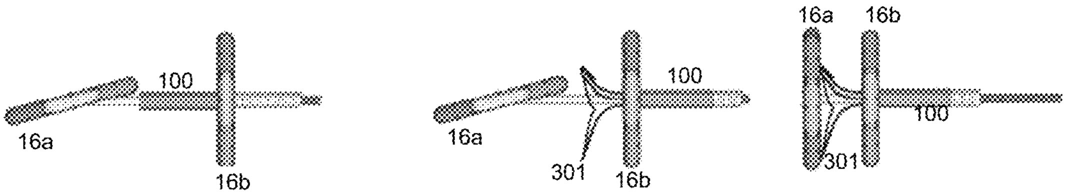
FIG. 54B shows a side view of when the proximal magnet deployed in the proximal lumen, the device extends into the distal lumen and the distal magnet is deployed. The wire jaw control member is deployed. The distal magnet is manipulated with the wire jaw control member acting as a support.

FIG. 54B illustrates a side view of the control member deployment of FIG. 54A.

Figure 55A:
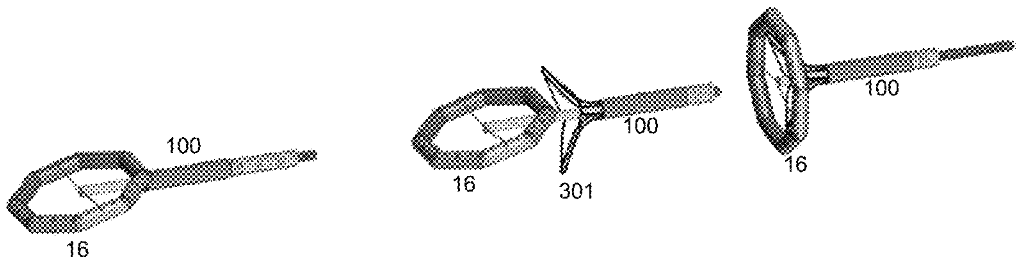
FIG. 55A shows a singular magnet being deployed, the wire jaw control member being deployed, and the singular magnet being manipulated with the jaw acting as a support.

FIG. 55A illustrates the wire jaw control member 301 manipulating a single magnet. In this embodiment, a magnetic anastomosis device 16 is deployed into a lumen. Once deployed, the user pulls back on the delivery device 100 to deploy the wire jaw control member 301. The control member, having been in a contracted position while stored in the delivery device 100, expands to a diameter greater than that of the magnet 16. The control member 301 engages the singular magnetic device 16 in order to orient and position the magnet in the target area to form an anastomosis. Once the magnet is in the proper position, the user pulls back on the delivery device 100 to contract the control member 301 to a diameter smaller than that of the magnet 16, and retract the control member 301 into the delivery device 100 for removal from the patient.

Figure 55B:
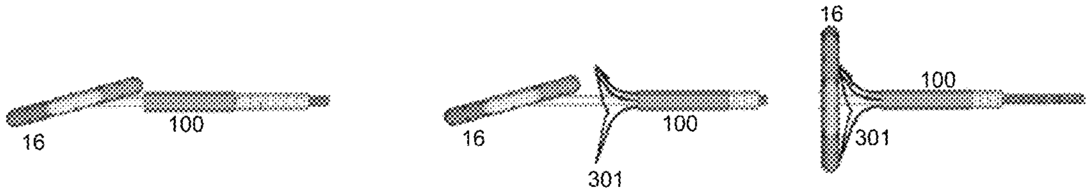
FIG. 55B shows a side view of a singular magnet being deployed, the wire jaw control member being deployed, and the singular magnet being manipulated with the wire jaw control member acting as a support.

FIG. 55B depicts a side view of the control member deployment of FIG. 55A. FIGS. 56A, 56B, 57A, and 57B show another concept of an expandable/contractible mechanism configured to control and manipulate the distal anastomosis device within the distal lumen configured as a basket array.

Figure 56A:
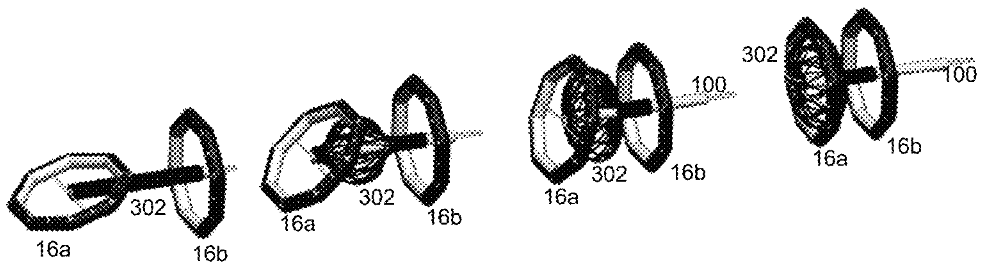
FIG. 56A shows when a proximal magnet is deployed in the proximal lumen, the device extends into the distal lumen and the distal magnet is deployed. The basket control member is extended and expands up to the diameter of the magnet. The distal magnet is manipulated with the basket control member acting as a support.

FIG. 56A illustrates the deployment of a basket array control member 302. The basket array control member 302 is deployed with the distal anastomosis device 16*a*, the control member 302 having its distal end connected to the distal anastomosis device 16*a*, and the proximal end attached to the proximal anastomosis device 16*b*. The user pulls back on the delivery device 100, bringing the distal magnet 16*a* closer to the proximal magnet 16*b*. As the distal magnet 16*a* is brought toward the proximal magnet 16*b*, the basket array control member 302 expands to a diameter greater than that of the magnet and engages the distal magnet 16*a*. Once engaged, the control member 302 can rotate the distal magnet 16*a* to align it with the proximal magnet 16*b*. The control member 302 can also exert additional force on the distal magnet 16*a* in order to pair it with the proximal magnet 16*b*. Once the magnets are aligned and paired, the user pulls back on the delivery device 100 to contract the basket array control member to a diameter less than that of the enterotomy, and retract the control member 302 into the delivery device 100 for removal from the patient.

Figure 56B:
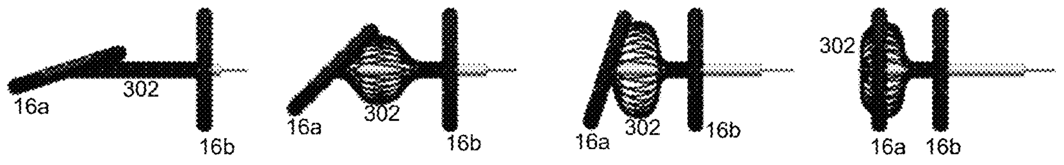
FIG. 56B shows a side view of when a proximal magnet is deployed in the proximal lumen, the device extends into the distal lumen and the distal magnet is deployed. The basket control member is extended and expands up to the diameter of the magnet. The distal magnet is manipulated with the basket control member acting as a support.

FIG. 56B displays a side view of the basket array system and method of FIG. 56A.

Figure 57A:
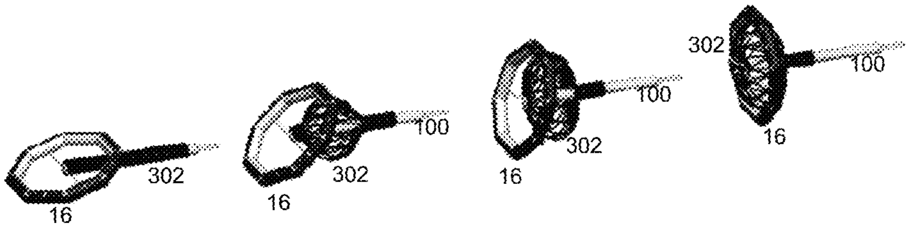
FIG. 57A shows a singular magnet being deployed, the basket control member being deployed, the basket control member expanding up to the diameter of the magnet, and the singular magnet being manipulated with the basket control member acting as a support.

FIG. 57A illustrates the basket array control member manipulating a single magnet. In this embodiment, a magnetic anastomosis device 16 is deployed into a lumen. The distal end of the control member 302 is attached to the magnet 16 and by pulling back on the delivery device the user expands the basket array control member 302 to a diameter greater than that of the magnet 16. The control member 302 engages the magnet 16 in order to align and position the magnet 16 at the target site to form an anastomosis. Once the magnet 16 is in the proper position, the user pulls back on the delivery device 100 to contract the control member 302 to a diameter smaller than that of the magnet, and retract the control member 302 into the delivery device 100 for removal from the patient.

Figure 57B:
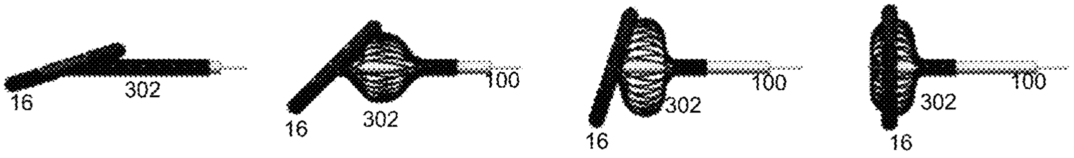
FIG. 57B shows a side view of a singular magnet being deployed, the basket control member being deployed, the basket control member expanding up to the diameter of the magnet, and the singular magnet being manipulated with the basket control member acting as a support.

FIG. 57B depicts a side view of the control member deployment of FIG. 57A.

Figure 58:
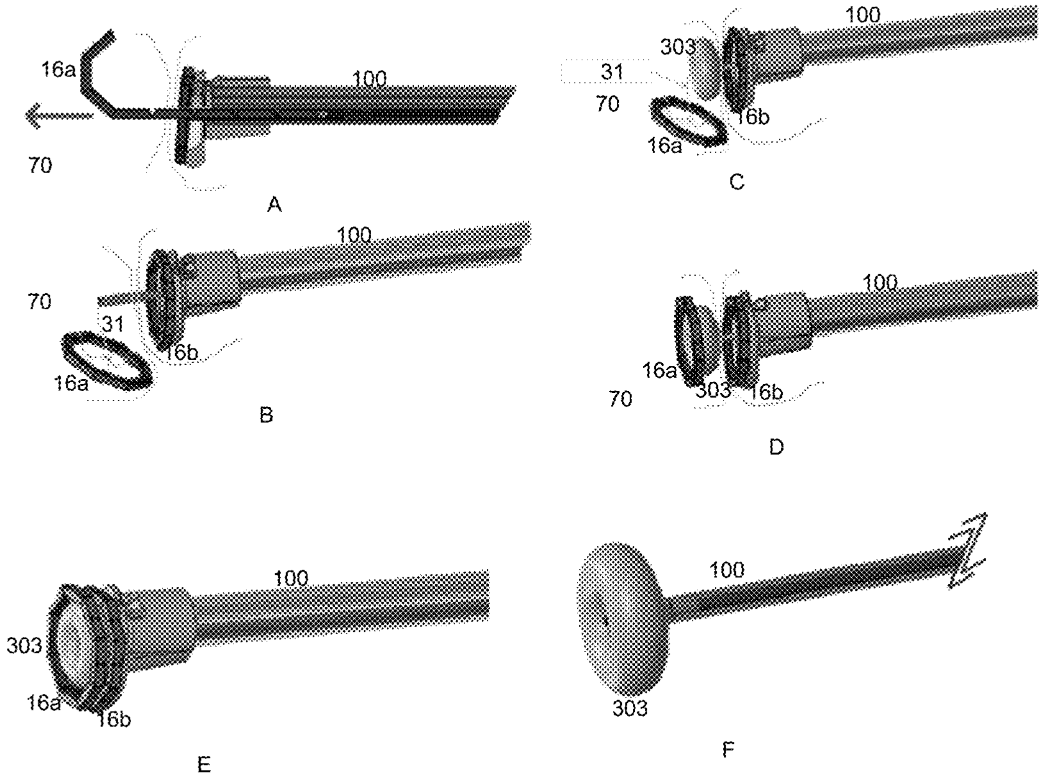
FIG. 58 shows a side view of the proximal magnet having been deployed in the proximal lumen, the catheter is pushed out releasing a balloon control member and the distal magnet into the distal lumen. The balloon is then inflated in the distal lumen and the catheter is pulled until the distal magnet is manipulated by the balloon control member and the distal magnet is attached to the proximal magnet.

FIG. 58 shows another concept of an expandable/contractible mechanism configured to control and manipulate the distal anastomosis device within the distal lumen configured as a balloon. After the proximal magnet 16*b* is deployed in the proximal lumen 71, the distal magnet 16*a* is deployed into the distal lumen 70 where it self-assembles from a linear formation to a polygonal shape (FIG. 58(A)). With the distal magnet 16*a* deployed (FIG. 58(B)), the user pulls back on the delivery device 100 to deploy the balloon cuff control member 303 (FIG. 58(C)). The balloon cuff control member 303 is inflated in the distal lumen 70 to a diameter greater than that of the distal magnet 16*a*. By pulling on the central sutures 31, the user can control the distal magnet 16*a*. The balloon cuff 303 engages with the distal magnet 16*a* in order to align it with the proximal magnet 16*b* (FIG. 58(D)). In some embodiments, the control member 303 may exert additional force on the distal magnet 16*a* to pair it with the proximal magnet 16*b*. Once the magnetic anastomosis devices 16*a*, 16*b* are aligned and paired, the balloon cuff control member 303 is deflated to a diameter less than that of the magnetic assembly and retracted into the delivery device 100 for subsequent removal from the patient.

Figure 53:
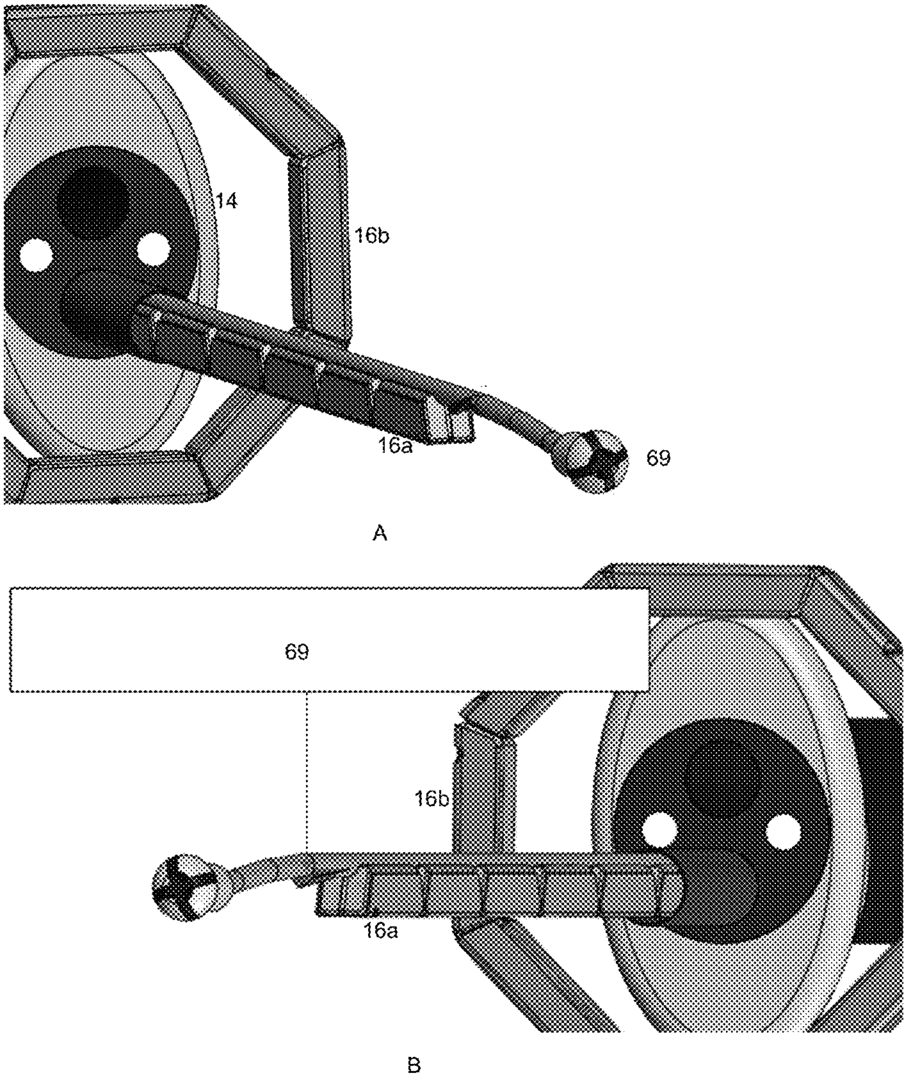
FIG. 53 shows two tip configurations, in accordance with various exemplary embodiments.

Another concept includes a piercing tip 69 configuration that is configured to help orient the magnetic segments during deployment of the magnetic compression anastomosis device. FIG. 53 shows two tip configurations, in accordance with various exemplary embodiments. The A configuration includes a piercing tip 69 with a spiral support that helps to orient the magnetic segments 16*a* during deployment of the magnetic compression anastomosis device. The B configuration includes a piercing tip 69 with a wedge support that helps to orient the magnetic segments 16*a* during deployment of the magnetic compression device. Of course, other configurations are possible based on the concept of tip configurations to help with orientation.

Potential Claims

Various embodiments of the present invention may be characterized by the potential claims listed in the paragraphs following this paragraph (and before the actual claims provided at the end of the application). These potential claims form a part of the written description of the application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public. Nor are these potential claims intended to limit various pursued claims.

Without limitation, potential subject matter that may be claimed (prefaced with the letter "P" so as to avoid confusion with the actual claims presented below) includes:

P1. An apparatus that has capabilities to cut, dissect, dilate and cauterize tissue, individually or used in conjunction with other methods, between one or more mating devices (e.g., compression anastomosis devices) creating and/or capturing an open conduit for compression or decompression or nutrient bypass, e.g., while maintaining concentricity with a deployment channel.

P2. An apparatus that has ability to be delivered into an adjacent wall which then can act as a conduit to deliver a compression anastomosis device.

P3. An apparatus that allows tissue to be sheared, dilated or excised between one or more compression devices.

P4. An apparatus with a retractable sharp tip or energy to provide tissue desecration.

P5. An apparatus that has ability to deliver a control mechanism consisting of an array of at least one articulating member into an adjacent lumen that expands to a diameter greater than the created enterotomy in order to increase the mechanical advantage used to control connecting members attached to a distally deployed compression anastomosis device. The control mechanism's increased diameter can also serve as a tool to dilate and/or expand the created enterotomy.

P6. An apparatus that allows for control and manipulation of a compression device in a distal lumen using connecting members, creating alignment within 15° between the deployment channel axis and the compression device's mating axis. The control mechanism allows movement in distal and proximal directions and can couple and decouple mated compression anastomosis devices.

P7. An apparatus with a biased sharp cutting tip or monopolar or bipolar energized tip to provide tissue desecration that creates an enterotomy centered coaxially with a delivery device's working channel. The tip's support serves as a guide for deployment of a control member and a compression anastomosis device into the distal lumen, wrapping it in a prescribed manner around the support to orient and present the compression device upon deployment. In certain configurations, the tip may also act as a control member (i.e. an energized basket) and/or be used to dilate the created enterotomy.

P8. An expandable/retractable control mechanism comprising an articulating member that expands to a diameter greater than the enterotomy in order to dilate/expand the enterotomy, align the compression devices and increase the mechanical advantage used to control the compression anastomosis device.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for positioning compression anastomosis devices, the method comprising:

deploying a first compression anastomosis device from a distal end of a delivery device into a proximal lumen;

positioning the anastomosis device against a tissue wall;

piercing the tissue wall to create an enterotomy between adjacent lumens;

deploying a second anastomosis device through the enterotomy into a distal lumen;

independently deploying an expandable and contractible control member into the enterotomy;

expanding the control member to dilate the enterotomy;

engaging the control member with the second anastomosis device;

manipulating the control member rotationally and laterally with the distal anastomosis device so as to align the two anastomosis devices;

bringing the anastomosis devices together so as to capture the enterotomy;

contracting the control member to a diameter equal to or less than that of the delivery device; and retracting the control member into the delivery device.

2. The method as described in claim 1, wherein the control member is deployed on the distal side of the distal anastomosis device as a backstop.

3. The method as described in claim 1, wherein the control member is deployed between the anastomosis devices to capture the created enterotomy.

4. The method as described in claim 1, wherein the control member is a basket.

5. The method as described in claim 1, wherein the control member is a balloon cuff.

6. The method as described in claim 1, wherein the control member is a wire jaw.

7. The method as described in claim 1, wherein piercing the tissue wall to create the enterotomy between the adjacent lumens comprises use of a piercing device configured to cut, dissect, and/or dilate tissue.

8. The method as described in claim 7, wherein the piercing device is a hot needle.

9. The method as described in claim 7, wherein the piercing device is a hot tip emitting monopolar energy.

10. The method as described in claim 7, wherein the piercing device is a coring needle.

11. The method as described in claim 7, wherein the piercing device is a corkscrew.

12. The method as described in claim 7, wherein the piercing device is deployed from the distal end of the delivery device.

13. The method as described in claim 1, wherein deploying the second anastomosis device through the enterotomy into the distal lumen comprises deploying the second anastomosis device from the distal end of the delivery device.

14. The method as described in claim 1, wherein engaging the control member with the second anastomosis device comprises using the control member as a backstop for the second anastomosis device.

15. The method as described in claim 1, wherein independently deploying the expandable and contractible control member into the enterotomy comprises deploying the control member from the distal end of the delivery device.

16. The method as described in claim 1, wherein the distal end of the delivery device comprises a corkscrew, and wherein the method further comprises:

using the corkscrew to secure the distal end of the delivery device to the tissue wall prior to piercing the tissue wall to create the enterotomy.

17. The method as described in claim 16, wherein a distal end of the corkscrew comprises a needle point.

18. The method as described in claim 16, wherein using the corkscrew to secure the distal end of the delivery device to the tissue wall prior to piercing the tissue wall to create the enterotomy comprises rotating the delivery device to screw the corkscrew into the tissue wall.

* * * * *